United States Patent
Kuduk et al.

(10) Patent No.: US 9,353,104 B2
(45) Date of Patent: May 31, 2016

(54) SUBSTITUTED PYRIDIZINONE DERIVATIVES AS PDE10 INHIBITORS

(71) Applicant: MERCK SHARP & DOHME CORP., Rahway, NJ (US)

(72) Inventors: Scott D. Kuduk, Harleysville, PA (US); Casey C. McComas, Phoenixville, PA (US); Thomas S. Reger, Lansdale, PA (US); Changhe Qi, Shanghai (CN)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 14/769,829

(22) PCT Filed: Mar. 10, 2014

(86) PCT No.: PCT/US2014/022266
§ 371 (c)(1),
(2) Date: Aug. 24, 2015

(87) PCT Pub. No.: WO2014/150114
PCT Pub. Date: Sep. 25, 2014

(65) Prior Publication Data
US 2016/0016947 A1    Jan. 21, 2016

(30) Foreign Application Priority Data
Mar. 15, 2013 (WO) ................ PCT/CN2013/072709

(51) Int. Cl.
| | | |
|---|---|---|
| *A61K 31/501* | (2006.01) | |
| *C07D 417/14* | (2006.01) | |
| *C07D 403/14* | (2006.01) | |
| *C07D 401/14* | (2006.01) | |
| *C07D 413/14* | (2006.01) | |
| *C07D 401/12* | (2006.01) | |
| *C07D 471/04* | (2006.01) | |
| *A61K 31/50* | (2006.01) | |
| *C07D 403/12* | (2006.01) | |

(52) U.S. Cl.
CPC ............. *C07D 417/14* (2013.01); *A61K 31/50* (2013.01); *A61K 31/501* (2013.01); *C07D 401/12* (2013.01); *C07D 401/14* (2013.01); *C07D 403/12* (2013.01); *C07D 403/14* (2013.01); *C07D 413/14* (2013.01); *C07D 471/04* (2013.01)

(58) Field of Classification Search
CPC .. C07D 417/14; C07D 401/12; C07D 401/14; C07D 403/12; C07D 403/14; C07D 413/14; C07D 471/04
See application file for complete search history.

(56) References Cited

U.S. PATENT DOCUMENTS

| 2010/0204241 A9 | 8/2010 | Dal Piaz et al. |
| 2011/0166135 A1 | 7/2011 | Morimoto et al. |
| 2015/0291561 A1* | 10/2015 | Kuduk ................ C07D 401/14 514/252.02 |

FOREIGN PATENT DOCUMENTS

| WO | WO2009032277 | 3/2009 |
| WO | WO2010063610 | 6/2010 |
| WO | WO2012162213 | 11/2012 |
| WO | WO2013028590 | 2/2013 |

OTHER PUBLICATIONS

S-W Yang et al., 22 Bioorganic & Medicinal Chemistry Letters, 235-239 (2012).*
J.A. Siuciak et al., 22 CNS Drugs, 983-993 (2008).*
Becker et al., Phosphodiesterase Inhibitors—Are They Potential Neuroleptic Drugs?, Behavioural Brain research, 2008, pp. 155-160, 186.
Fujishige et al., Cloning and Characterization of a Novel Human Phosphodiesterase that Hydrolyzes Both cAMP and cGMP (PDE10A), J. Bilogical Chemical, 1999, pp. 18438-18445, 274.
Huang et al., A Fluroescence Polarization Assay for Cyclic Nucleotide Phosphodiesterases, J. of Biomolecular Screening, 2002, pp. 215-222, 7.
Kehler, The Potential Therapeutic Use of Phosphodiesterase 10 Inhibitors, Expert Opinion, 2007, pp. 147-158, 17.
Lieberman et al., Effectiveness of Antipsychotic Drugs in Patients with Chronic Schizophrenia, New England J. of Medicine, Sep. 22, 2005, pp. 1209-1223, 353, US.
Loughney et al., Isolation and Characterization of PDE10A, a Novel Human 3', 5'-Cyclic Nucleotide Phosphodiesterase, Gene, 1999, pp. 109-117, 234.

(Continued)

*Primary Examiner* — Alexander R Pagano
(74) *Attorney, Agent, or Firm* — Sylvia A. Ayler; John C. Todaro

(57) ABSTRACT

The present invention is directed to substituted pyridizinone compounds of formula I which are useful as therapeutic agents for the treatment of central nervous system disorders associated with phosphodiesterase 10 (PDE10). The present invention also relates to the use of such compounds for treating neurological and psychiatric disorders, such as schizophrenia, psychosis or Huntington's disease, and those associated with striatal hypofunction or basal ganglia dysfunction.

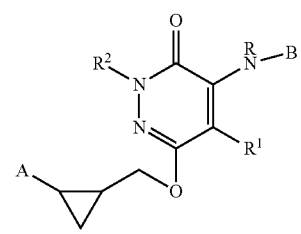

(I)

16 Claims, No Drawings

(56) References Cited

OTHER PUBLICATIONS

Mosser et al., Automation of In Vitro Dose-Inhibition Assays Utlizing the Tecan Genesis and an Integratd Software Package to Support the Drug Discovery Process, JALA, 2003, pp. 54-63, 8, Sage Publications.

Schmidt et al., Pre-clincal Characterization of Selective PHosphodiesterease 10A Inhibitors: A New Therapeutic Approach to the Treatment of Schizophrenia, J. of Pharmacology and Experimental Thereapeutics, 2008, pp. 690-690, 325.

Siuciak et al., Inhibiton of the Striatum-Enriched Phosphodiesterease PDE10A: A novel Approach to the Treament of Psychosis, Neuropharmacology, 2006, pp. 386-396, 51.

Soderling et al., Isolation and Characterization of a Dual-Substrate Phosphodiesterase Gene Family: PDE10A, Proc. Natl. Acad. Sci. USA, Jun. 1999, pp. 7071-7076, 96.

Threlfell et al., Inhibition of Phosphodiesterase 10A Increases the Responsiveness of Striatal Projection Neurons to the Cortical Stimulation, J. of Pharmacology and Experimental Therapeutics, J. of Pharmacology and Experimental Therapeutics, 2009, pp. 785-795, 328.

\* cited by examiner

SUBSTITUTED PYRIDIZINONE DERIVATIVES AS PDE10 INHIBITORS

CROSS REFERENCE TO RELATED APPLICATIONS

This application is the National Stage of International Application No. PCT/US2014/022266 filed on Mar. 10, 2014, which claims the benefit under International No. PCT/CN2013/072709 filed on Mar. 15, 2013.

FIELD OF THE INVENTION

The invention relates generally to compounds which act as inhibitors of the phosphodiesterase (PDE) 10 enzyme, compositions and therapeutic uses thereof.

BACKGROUND OF THE INVENTION

Schizophrenia is a debilitating disorder affecting the psychic and motor functions of the brain. It is typically diagnosed in individuals in their early to mid-twenties and symptoms include hallucinations and delusions or at the other extreme, anhedonia or social withdrawal. Across the spectrum, the symptoms are indicative of cognitive impairment and functional disabilities. Notwithstanding improvements in antipsychotic treatments, current therapies, including typical (haloperidol) and atypical (clozapine or olanzapine) antipsychotics, have been less than acceptable and result in an extremely high rate of noncompliance or discontinuation of medication. Dissatisfaction with therapy is attributed to lack of efficacy or intolerable and unacceptable side affects. The side effects have been associated with significant metabolic, extrapyramidal, prolactic and cardiac adverse events. See, Lieberman et al., N. Engl. J. Med. (2005) 353:1209-1223.

While multiple pathways are believed to be involved with the pathogenesis of schizophrenia leading to psychosis and cognition deficits, much attention has focused on the role of glutamate/NMDA dysfunction associated with cyclic guanosine monophosphate (cGMP) levels and the dopaminergic D2 receptor associated with cyclic adenosine monophosphate (cAMP). These ubiquitous second messengers are responsible for altering the function of many intracellular proteins. Cyclic AMP is thought to regulate the activity of cAMP-dependent protein kinase (PKA), which in turns phosphorylates and regulates many types of proteins including ion channels, enzymes and transcription factors. Similarly, cGMP is also responsible for downstream regulation of kinases and ion channels.

One pathway for affecting the levels of cyclic nucleotides, such as cAMP and cGMP, is to alter or regulate the enzymes that degrade these enzymes, known as 3',5'-cyclic nucleotide specific phosphodiesterases (PDEs). The PDE superfamily includes twenty one genes that encode for eleven families of PDEs. These families are further subdivided based on catalytic domain homology and substrate specificity and include the 1) cAMP specific, PDE4A-D, 7A and 7B, and 8A and 8B, 2) cGMP specific, PDE 5A, 6A-C, and 9A, and 3) those that are dual substrate, PDE 1A-C, 2A, 3A and 3B, 10A, and 11A. The homology between the families, ranging from 20% to 45% suggests that it may be possible to develop selective inhibitors for each of these subtypes.

The identification of PDE10 was reported by three groups independently and was distinguished from other PDEs on the basis of its amino acid sequence, functional properties, and tissue distribution (Fujishige et al., J. Biol. Chem. (1999) 274:18438-18445; Loughney et al., Gene (1999) 234: 109-117; Soderling et al., PNAS, USA (1999) 96: 7071-7076). The PDE10 subtype at present consists of a sole member, PDE10A, having alternative splice variants at both the N-terminus (three variants) and C-terminus (two variants), but that does not affect the GAF domain in the N-terminus or the catalytic site in C-terminus. The N-terminus splice variants, PDE10A1 and PDE10A2, differ in that the A2 variant has a PKA phosphorylation site that upon activation, i.e. PKA phosphorylation in response to elevated cAMP levels, results in intracellular changes to the localization of the enzyme. PDE10A is unique relative to other PDE families also having the conserved GAF domain in that its ligand is cAMP, while for the other GAF-domain PDEs the ligand is cGMP (Kehler et al., Expert Opin. Ther. Patents (2007) 17(2): 147-158). PDE10A has limited but high expression in the brain and testes. The high expression in the brain and, in particular, the neurons of the striatum, unique to PDE10, suggests that inhibitors thereto may be well suited from treating neurological and psychiatric disorders and conditions. See PCT applications PCT/US12/051522 filed Aug. 20, 2012 (Provisional U.S. Ser. No. 61/527,392) and PCT/US12/038759 filed May 21, 2012 (Provisional U.S. Ser. No. 61/489,457) for background discussion.

Inhibition of PDE10 is believed to be useful in the treatment of schizophrenia and a wide variety of conditions or disorders that would benefit from increasing levels of cAMP and/or cGMP within neurons, including a variety neurological, psychotic, anxiety and/or movement disorders. Accordingly, agents that inhibit PDE10 and especially PDE10A would be desirable as therapeutics for neurological and psychiatric disorders.

SUMMARY OF THE INVENTION

The present invention is directed to substituted pyridazinone compounds and the like which may be useful as therapeutic agents for the treatment of central nervous system disorders associated with phosphodiesterase 10 (PDE10). The present invention also relates to the use of such compounds for treating neurological and psychiatric disorders, such as schizophrenia, psychosis or Huntington's disease, and those associated with striatal hypofunction or basal ganglia dysfunction.

DETAILED DESCRIPTION OF THE INVENTION

The present invention is directed to compounds of the formula I:

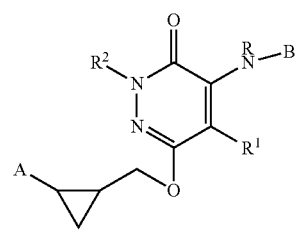

wherein:
R is hydrogen, $C_{1-6}$alkyl, $C_{2-4}$alkenyl, $C_{2-4}$ alkynyl, or $(CH_2)_nC_{5-10}$ heteroaryl said heteroaryl optionally substituted with 1 to 3 groups of $R^a$;
$R^1$ is hydrogen, $C_{1-6}$alkyl or halogen, said alkyl optionally substituted with 1 to 3 groups of $R^a$;

$R^2$ is $C_{1-6}$alkyl, or $(CH_2)_nC_{6-10}$aryl, said aryl optionally substituted with 1 to 3 groups of $R^a$;

A is $C_{5-10}$heteroaryl optionally substituted with 1 to 3 groups of $R^a$;

B is $(CH_2)_nC_{6-10}$aryl, $(CH_2)_nC_{5-10}$heteroaryl, —C(O)$(CH_2)_nC_{6-10}$aryl, or —C(O)$(CH_2)_nC_{5-10}$heteroaryl, said aryl and heteroaryl optionally substituted with 1 to 3 groups of $R^a$;

$R^a$ selected from the group consisting of:
(1) $(CH_2)_nO_{0-1}C_{1-4}$ haloalkyl,
(2) halogen,
(3) $(CH_2)_n$OR,
(4) $C_{1-6}$alkyl,
(5) $(CH_2)_nC_{3-6}$cycloalkyl,
(6) $(CH_2)_nC_{6-10}$aryl, said aryl optionally substituted with one or more of OR, or $C_{1-6}$alkyl;
(7) —$(CH_2)_nCO_2R$,
(8) —$(CH_2)_nCN$,
(9) $S(O)_pR$,
(10) $C_{2-6}$ alkenyl,
(11) —$N(R)_2$,
n is 0, 1, 2, 3, or 4,
p is 0, 1, or 2,
or a pharmaceutically acceptable salt thereof.

An embodiment of the invention of formula I is realized when R is hydrogen.

Another embodiment of the invention of formula I is realized when R is $C_{1-6}$ alkyl.

Still another embodiment of the invention of formula I is realized when R is $C_{2-4}$ alkenyl.

Still another embodiment of the invention of formula I is realized when R is $C_{2-4}$ alkynyl.

Still another embodiment of the invention of formula I is realized when R is $(CH_2)_nC_{5-10}$heteroaryl, said heteroaryl optionally substituted with 1 to 3 groups of $R^a$.

Another embodiment of the invention of formula I is realized when $R^1$ is hydrogen.

Another embodiment of the invention of formula I is realized when $R^1$ is optionally substituted $C_{1-6}$ alkyl.

Another embodiment of the invention of formula I is realized when $R^1$ is halogen.

Another embodiment of the invention of formula I is realized when the n in B is 0, 1, or 2. A subembodiment of this aspect of the invention of formula I is realized when the n in B is 1. Another subembodiment of this aspect the invention of formula I is realized when the n in B is 2.

An embodiment of the invention of formula I is realized when A is selected from the group consisting of pyridyl, quinolinyl, pyrazolyl, indazolyl, and cyclopentapyridinyl said of pyridyl, quinolinyl, pyrazolyl, indazolyl, and cyclopentapyridinyl optionally substituted with 1 to 3 groups of $R^a$.

Another embodiment of the invention of formula I is realized when B is selected from the group consisting of $(CH_2)_n$ $C_{6-10}$aryl and $(CH_2)_nC_{5-10}$ heteroaryl and the aryl or heteroaryl is isoxazolyl, pyrimidinyl, pyradizinyl, pyrazolopyridinyl, triazolyl thiazolyl, thiadiazolyl, phenyl, pyridyl, or pyrazolyl, said isoxazolyl, pyrimidinyl, pyradizinyl, pyrazolopyridinyl, triazolyl thiazolyl, thiadiazolyl, phenyl, pyridyl, and pyrazolyl are optionally substituted with 1 to 3 groups of $R^a$.

Another embodiment of the invention of formula I is realized when B is selected from the group consisting of —C(O) $C_{6-10}$aryl and —(CO)$C_{5-10}$ heteroaryl and the aryl or heteroaryl is isoxazolyl, pyrimidinyl, pyradizinyl, pyrazolopyridinyl, triazolyl thiazolyl, thiadiazolyl, phenyl, pyridyl, or pyrazolyl, said isoxazolyl, pyrimidinyl, pyradiz-inyl, pyrazolopyridinyl, triazolyl thiazolyl, thiadiazolyl, phenyl, pyridyl, and pyrazolyl are optionally substituted with 1 to 3 groups of $R^a$.

An embodiment of the present invention includes compounds wherein $R^a$ is selected from the group consisting of $(CH_2)_n(O)_{0-1}C_{1-4}$ haloalkyl, halogen, $(CH_2)_n$OR, and $C_{1-6}$alkyl. A subembodiment of this aspect of the invention is realized when $R^a$ is selected from the group consisting of OH, $(CH_2)_2OCH_3$, $(CH_2)_{1-2}$OH, $OCH(CH_3)_2$, halogen, $CF_2$, $CF_3$, $OCF_2$, $OCF_3$, $CH_2CF_3$, $CH_2CHF_2$, $OCH_3$, $CHCH_3OH$, $OCH_2CH_3$, $C(CH_3)OH$, $CH(CF_2)OH$, $OCH(CH_2)_2OH$, $CH(CF_3)OH$, methyl, ethyl, propyl, and propylene. Another subembodiment of this aspect of the invention is realized when $R^a$ is selected from the group consisting of fluorine, chlorine, bromine, $CF_2$, $CF_3$, $OCF_2$, $OCF_3$, $OCH_3$, $OCH_2CH_3$, methyl, ethyl, and propyl.

An embodiment of the present invention includes compounds wherein A is optionally substituted pyridyl. A subembodiment of this invention is realized when the pyridyl is substituted with 1 to 3 groups selected from $(CH_2)_n(O)_{0-1}C_{1-4}$ haloalkyl, halogen, $C_{1-6}$alkyl and $(CH_2)_n$OR. Another subembodiment of this invention is realized when the pyridyl is substituted with 1 to 3 groups selected from $R^a$ is selected from the group consisting of fluorine, chlorine, $CF_2$, $CF_3$, $OCF_2$, $OCF_3$, $OCH_3$, $OCH_2CH_3$, methyl, ethyl, and propyl.

An embodiment of the present invention includes compounds wherein A is optionally substituted quinolinyl. A subembodiment of this invention is realized when the quinolinyl is optionally substituted with 1 to 3 groups selected from $(CH_2)_n(O)_{0-1}C_{1-4}$ haloalkyl, halogen, $C_{1-6}$alkyl and $(CH_2)_n$ OR. Another subembodiment of this invention is realized when the quinolinyl is substituted with 1 to 3 groups selected from $R^a$ is selected from the group consisting of fluorine, chlorine, $CF_2$, $CF_3$, $OCF_2$, $OCF_3$, $OCH_3$, $OCH_2CH_3$, methyl, ethyl, and propyl.

An embodiment of the present invention includes compounds wherein A is optionally substituted pyrazolyl. A subembodiment of this invention is realized when the pyrazolyl is optionally substituted with 1 to 3 groups selected from $(CH_2)_n(O)_{0-1}C_{1-4}$ haloalkyl, halogen, $C_{1-6}$alkyl and $(CH_2)_n$ OR. Another subembodiment of this invention is realized when the pyrazolyl is substituted with 1 to 3 groups selected from $R^a$ is selected from the group consisting of fluorine, chlorine, $CF_2$, $CF_3$, $OCF_2$, $OCF_3$, $OCH_3$, $OCH_2CH_3$, methyl, ethyl, and propyl.

An embodiment of the present invention includes compounds wherein A is optionally substituted indazolyl. A subembodiment of this invention is realized when the indazolyl is optionally substituted with 1 to 3 groups selected from $(CH_2)_n(O)_{0-1}C_{1-4}$ haloalkyl, halogen, $C_{1-6}$alkyl and $(CH_2)_n$ OR. Another subembodiment of this invention is realized when the indazolyl is substituted with 1 to 3 groups selected from $R^a$ is selected from the group consisting of fluorine, chlorine, $CF_2$, $CF_3$, $OCF_2$, $OCF_3$, $OCH_3$, $OCH_2CH_3$, methyl, ethyl, and propyl.

An embodiment of the present invention includes compounds wherein A is optionally substituted cyclopentapyridinyl. A subembodiment of this invention is realized when the cyclopentapyridinyl is optionally substituted with 1 to 3 groups selected from $(CH_2)_n(O)_{0-1}C_{1-4}$ haloalkyl, halogen, $C_{1-6}$alkyl and $(CH_2)_n$OR. Another subembodiment of this invention is realized when the cyclopentapyridinyl is substituted with 1 to 3 groups selected from $R^a$ is selected from the group consisting of fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein B is optionally substituted $CH_2$thiazolyl.

A subembodiment of this invention is realized when the thiazolyl substituent is optionally substituted with 1 to 3 groups selected from $(CH_2)_n(O)_{0-1}C_{1-4}$ haloalkyl, halogen, $C_{1-6}$alkyl and $(CH_2)_n OR$. Another subembodiment of this invention is realized when the thiazolyl substituent is substituted with 1 to 3 groups selected from $R^a$ is selected from the group consisting of fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein B is optionally substituted $CH_2$thiadiazolyl. A subembodiment of this invention is realized when the thiadiazolyl substituent is optionally substituted with 1 to 3 groups selected from $(CH_2)_n(O)_{0-1}C_{1-4}$ haloalkyl, halogen, $C_{1-6}$alkyl and $(CH_2)_n OR$. Another subembodiment of this invention is realized when the thiadiazolyl substituent is substituted with 1 to 3 groups selected from $R^a$ is selected from the group consisting of fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein B is optionally substituted $CH_2$phenyl. A subembodiment of this invention is realized when the phenyl substituent is optionally substituted with 1 to 3 groups selected from $(CH_2)_n(O)_{0-1}C_{1-4}$ haloalkyl, halogen, $C_{1-6}$alkyl and $(CH_2)_n OR$. Another subembodiment of this invention is realized when the phenyl substituent is substituted with 1 to 3 groups selected from $R^a$ is selected from the group consisting of fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein B is optionally substituted $CH_2$pyridyl. A subembodiment of this invention is realized when the pyridyl substituent is optionally substituted with 1 to 3 groups selected from $(CH_2)_n(O)_{0-1}C_{1-4}$ haloalkyl, halogen, $C_{1-6}$alkyl and $(CH_2)_n OR$. Another subembodiment of this invention is realized when the pyridyl substituent is substituted with 1 to 3 groups selected from $R^a$ is selected from the group consisting of fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein B is optionally substituted $CH_2$pyrazolyl. A subembodiment of this invention is realized when the pyrazolyl substituent is optionally substituted with 1 to 3 groups selected from $(CH_2)_n(O)_{0-1}C_{1-4}$ haloalkyl 1, halogen, $C_{1-6}$alkyl and $(CH_2)_n OR$. Another subembodiment of this invention is realized when the pyrazolyl substituent is substituted with 1 to 3 groups selected from $R^a$ is selected from the group consisting of fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein B is optionally substituted $CH_2$isoxazolyl. A subembodiment of this invention is realized when the isoxazolyl substituent is optionally substituted with 1 to 3 groups selected from $(CH_2)_n(O)_{0-1}C_{1-4}$ haloalkyl, halogen, $C_{1-6}$alkyl and $—CH_2)_n OR$. Another subembodiment of this invention is realized when the isoxazolyl substituent is substituted with 1 to 3 groups selected from $R^a$ is selected from the group consisting of fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein B is optionally substituted $CH_2$pyrimidinyl. A subembodiment of this invention is realized when the pyrimidinyl substituent is optionally substituted with 1 to 3 groups selected from $(CH_2)_n(O)_{0-1}C_{1-4}$ haloalkyl, halogen, $C_{1-6}$alkyl and $(CH_2)_n OR$. Another subembodiment of this invention is realized when the pyrimidinyl substituent is substituted with 1 to 3 groups selected from $R^a$ is selected from the group consisting of fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein B is optionally substituted $CH_2$pyridazinyl. A subembodiment of this invention is realized when the pyridazinyl substituent is optionally substituted with 1 to 3 groups selected from $(CH_2)_n(O)_{0-1}C_{1-4}$ haloalkyl, halogen, $C_{1-6}$alkyl and $(CH_2)_n OR$. Another subembodiment of this invention is realized when the pyridazinyl substituent is substituted with 1 to 3 groups selected from $R^a$ is selected from the group consisting of fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein B is optionally substituted $CH_2$pyrazolopyridinyl. A subembodiment of this invention is realized when the pyrazolopyridinyl substituent is optionally substituted with 1 to 3 groups selected from $(CH_2)_n(O)_{0-1}C_{1-4}$ haloalkyl, halogen, $C_{1-6}$alkyl and $(CH_2)_n OR$. Another subembodiment of this invention is realized when the pyrazolopyridinyl substituent is substituted with 1 to 3 groups selected from $R^a$ is selected from the group consisting of fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein B is optionally substituted $CH_2$triazolyl. A subembodiment of this invention is realized when the triazolyl substituent is optionally substituted with 1 to 3 groups selected from $(CH_2)_n(O)_{0-1}C_{1-4}$ haloalkyl, halogen, $C_{1-6}$alkyl and $(CH_2)_n OR$. Another subembodiment of this invention is realized when the triazolyl substituent is substituted with 1 to 3 groups selected from $R^a$ is selected from the group consisting of fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein A is optionally substituted pyridyl and B is optionally substituted $CH_2$thiazoly. A subembodiment of this aspect of the invention is realized A and B are optionally substituted with 1 to 3 groups selected from $(CH_2)_n(O)_{0-1}C_{1-4}$ haloalkyl, halogen, $C_{1-6}$alkyl and $(CH_2)_n OR$, such as fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein A is optionally substituted pyridyl and B is optionally substituted $CH_2$thiadiazoly. A subembodiment of this aspect of the invention is realized A and B are optionally substituted with 1 to 3 groups selected from $(CH_2)_n(O)_{0-1}C_{1-4}$ haloalkyl, halogen, $C_{1-6}$alkyl and $(CH_2)_n OR$, such as fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein A is optionally substituted pyridyl and B is optionally substituted $CH_2$pyrazolyl. A subembodiment of this aspect of the invention is realized A and B are optionally substituted with 1 to 3 groups selected from $(CH_2)_n(O)_{0-1}C_{1-4}$ haloalkyl, halogen, $C_{1-6}$alkyl and $(CH_2)_n OR$, such as fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein A is optionally substituted pyridyl and B is optionally substituted $CH_2$pyridyl. A subembodiment of this aspect of the invention is realized A and B are optionally substituted with 1 to 3 groups selected from $(CH_2)_n(O)_{0-1}C_{1-4}$ haloalkyl, halogen, $C_{1-6}$alkyl and $(CH_2)_nOR$, such as fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein A is optionally substituted pyridyl and B is optionally substituted $CH_2$phenyl. A subembodiment of this aspect of the invention is realized A and B are optionally substituted with 1 to 3 groups selected from $(CH_2)_n(O)_{0-1}C_{1-4}$ haloalkyl, halogen, $C_{1-6}$alkyl and $(CH_2)_nOR$, such as fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein A is optionally substituted pyrazolyl and B is optionally substituted $CH_2$thiazolyl. A subembodiment of this aspect of the invention is realized A and B are optionally substituted with 1 to 3 groups selected from $(CH_2)_n(O)_{0-1}C_{1-4}$ haloalkyl, halogen, $C_{1-6}$alkyl and $(CH_2)_nOR$, such as fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein A is optionally substituted pyrazolyl and B is optionally substituted $CH_2$thiadiazolyl. A subembodiment of this aspect of the invention is realized A and B are optionally substituted with 1 to 3 groups selected from $(CH_2)_n(O)_{0-1}C_{1-4}$ haloalkyl, halogen, $C_{1-6}$alkyl and $(CH_2)_n$OR, such as fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein A is optionally substituted pyrazolyl and B is optionally substituted $CH_2$pyridyl. A subembodiment of this aspect of the invention is realized A and B are optionally substituted with 1 to 3 groups selected from $(CH_2)_n(O)_{0-1}C_{1-4}$ haloalkyl, halogen, $C_{1-6}$alkyl and $(CH_2)_nOR$, such as fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein A is optionally substituted pyrazolyl and B is optionally substituted $CH_2$pyrazolyl. A subembodiment of this aspect of the invention is realized A and B are optionally substituted with 1 to 3 groups selected from $(CH_2)_n(O)_{0-1}C_{1-4}$ haloalkyl, halogen, $C_{1-6}$alkyl and $(CH_2)_nOR$, such as fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein A is optionally substituted pyrazolyl and B is optionally substituted $CH_2$phenyl. A subembodiment of this aspect of the invention is realized A and B are optionally substituted with 1 to 3 groups selected from $(CH_2)_n(O)_{0-1}C_{1-4}$ haloalkyl, halogen, $C_{1-6}$alkyl and $(CH_2)_nOR$, such as fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein A is optionally substituted quinolinyl and B is optionally substituted $CH_2$thiadiazolyl, $CH_2$thiazolyl, $CH_2$pyridyl or $CH_2$pyrazolyl. A subembodiment of this aspect of the invention is realized A and B are optionally substituted with 1 to 3 groups selected from $(CH_2)_n(O)_{0-1}C_{1-4}$ haloalkyl, halogen, $C_{1-6}$alkyl and $(CH_2)_n$OR, such as fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein A is optionally substituted indazolyl and B is optionally substituted $CH_2$thiadiazolyl, $CH_2$thiazolyl, $CH_2$pyridyl or $CH_2$pyrazolyl. A subembodiment of this aspect of the invention is realized A and B are optionally substituted with 1 to 3 groups selected from $(CH_2)_n(O)_{0-1}C_{1-4}$ haloalkyl, halogen, $C_{1-6}$alkyl and $(CH_2)_n$OR, such as fluorine, chlorine, $CF_2$, $CF_3$, $OCF_2$, $OCF_3$, $OCH_3$, $OCH_2CH_3$, methyl, ethyl, and propyl.

Another embodiment of the present invention includes compounds wherein A is optionally substituted cyclopentapyridinyl and B is optionally substituted $CH_2$thiadiazolyl, $CH_2$thiazolyl, $CH_2$pyridyl or $CH_2$pyrazolyl. A subembodiment of this aspect of the invention is realized A and B are optionally substituted with 1 to 3 groups selected from $(CH_2)_n(O)_{0-1}C_{1-4}$ haloalkyl, halogen, $C_{1-6}$alkyl and $(CH_2)_n$OR, such as fluorine, chlorine, $CF_2$, $CF_3$, $OCF_2$, $OCF_3$, $OCH_3$, $OCH_2CH_3$, methyl, ethyl, and propyl.

Another embodiment of the invention of formula I is realized when A is optionally substituted quinolinyl, pyridyl, pyrazolyl or indazolyl and B is selected from the group consisting of —C(O)$C_{6-10}$aryl and —(CO)$C_{5-10}$ heteroaryl and the aryl or heteroaryl is isoxazolyl, pyrimidinyl, pyradizinyl, pyrazolopyridinyl, triazolyl thiazolyl, thiadiazolyl, phenyl, pyridyl, or pyrazolyl, said isoxazolyl, pyrimidinyl, pyradizinyl, pyrazolopyridinyl, triazolyl thiazolyl, thiadiazolyl, phenyl, pyridyl, and pyrazolyl are optionally substituted with 1 to 3 groups of $R^a$. A subembodiment of this invention is realized when A is optionally substituted pyridyl, pyrazolyl or indazolyl and B is selected from the group consisting of —(CO)$C_{5-10}$ heteroaryl and heteroaryl is thiazolyl, thiadiazolyl, pyridyl, or pyrazolyl, said thiazolyl, thiadiazolyl, pyridyl, or pyrazolyl optionally substituted with 1 to 3 groups of $R^a$.

An embodiment of the invention of formula I is represented by formula Ia and Iaa:

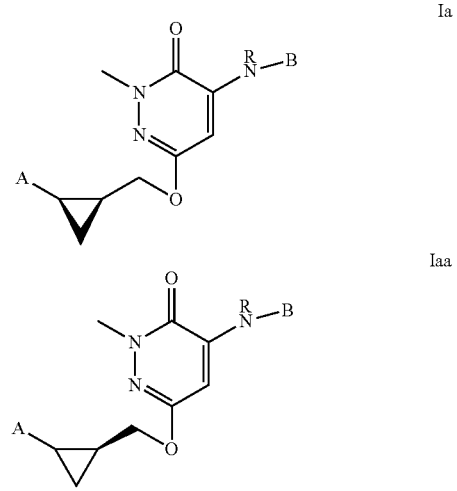

wherein R, A, and B are as defined herein; or a pharmaceutically acceptable salt thereof.

Another embodiment of the invention of formula I is represented by structural formula Ib:

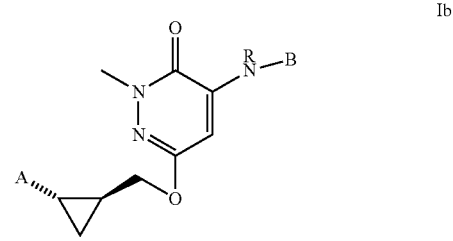

wherein R, A, and B are as defined herein; or a pharmaceutically acceptable salt thereof.

Still another embodiment of the invention of formula I is represented by structural formula Ic:

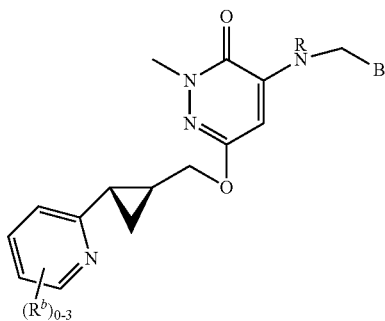

wherein R, and B are as defined herein and $R^b$ is $R^a$; or a pharmaceutically acceptable salt thereof.

Still another embodiment of the invention of formula I is represented by structural formula Id:

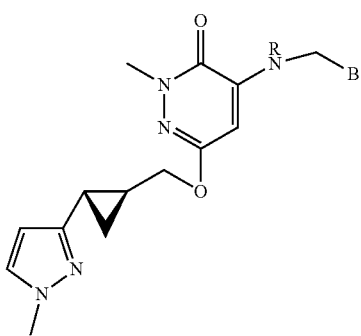

wherein R, and B are as defined herein, or a pharmaceutically acceptable salt thereof.

Specific embodiments of the present invention include a compound which is selected from the group consisting of the subject compounds of the Examples herein and pharmaceutically acceptable salts thereof and individual enantiomers and diastereomers thereof.

When any variable (e.g. aryl, heterocycle, $R^1$, $R^5$ etc.) occurs more than one time in any constituent, its definition on each occurrence is independent at every other occurrence. Also, combinations of substituents/or variables are permissible only if such combinations result in stable compounds.

As used herein, "alkyl" encompasses groups having the prefix "alk" such as, for example, alkoxy, alkanoyl, alkenyl, and alkynyl and means carbon chains which may be linear or branched or combinations thereof. Examples of alkyl groups include methyl, ethyl, propyl, isopropyl, butyl, sec- and tert-butyl, pentyl, hexyl, and heptyl. "Alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl. Preferably, alkenyl is $C_2$-$C_6$ alkenyl. Preferred alkynyls are $C_2$-$C_6$ alkynyl.

"Alkenyl," "alkynyl" and other like terms include carbon chains containing at least one unsaturated C—C bond.

As used herein, "haloalkyl" refers to an alkyl substituent as described herein containing at least one halogen substituent.

The term "cycloalkyl" refers to a saturated hydrocarbon containing one ring having a specified number of carbon atoms. Examples of cycloalkyl include cyclopropyl, cyclobutyl, cyclopentyl, and cyclohexyl.

The term "$C_{1-6}$" includes alkyls containing 6, 5, 4, 3, 2, or 1 carbon atoms The term "alkoxy", OR (where R is an alkyl), or "O-alkyl" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term heterocycle, heterocyclyl, or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "heteroatom" means O, S or N, selected on an independent basis.

A moiety that is substituted is one in which one or more hydrogens have been independently replaced with another chemical substituent. As a non-limiting example, substituted phenyls include 2-flurophenyl, 3,4-dichlorophenyl, 3-chloro-4-fluoro-phenyl, 2,4 fluor-3-propylphenyl. As another non-limiting example, substituted n-octyls include 2,4 dimethyl-5-ethyl-octyl and 3-cyclopentyloctyl. Included within this definition are methylenes (—$CH_2$—) substituted with oxygen to form carbonyl (—CO—).

Unless otherwise stated, as employed herein, when a moiety (e.g., cycloalkyl, hydrocarbyl, aryl, alkyl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, and (b) $C_1$-$C_6$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $SO_2CF_3$, $CF_3$, $SO_2Me$, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$alkylsulfinyl, arylalkylsulfnyl, arylsulfnyl, $C_1$-$C_8$ alkylsulfonyl, aralkylsulfonyl, arylsulfonyl, $C_0$-$C_6$ N-alkylcarbamoyl, $C_2$-$C_{15}$ N,N dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, or any of these rings fused or spiro-fused to a cycloalkyl, heterocyclyl, or aryl, wherein each of the foregoing is further optionally substituted with one more moieties listed in (a), above.

"Halogen" or "halo" refer to fluorine, chlorine, bromine and iodine.

The term "mammal" "mammalian" or "mammals" includes humans, as well as animals, such as dogs, cats, horses, pigs and cattle.

All patents, patent applications and publications cited herein, whether supra or infra, are hereby incorporated by reference in their entirety and are deemed representative of the prevailing state of the art.

As used in this specification and the appended claims, the singular forms "a," "an" and "the" include plural references unless the content clearly dictates otherwise. Thus, for example, reference to "a primer" includes two or more such primers, reference to "an amino acid" includes more than one such amino acid, and the like.

Compounds described herein may contain one or more double bonds and may thus give rise to cis/trans isomers as well as other conformational isomers. The present invention includes all such possible isomers as well as mixtures of such isomers unless specifically stated otherwise.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

In the compounds of generic Formula I, Ia, Iaa, Ib, Ic and Id the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of present invention are meant to also include the pharmaceutically acceptable salts, and also salts that are not pharmaceutically acceptable when they are used as precursors to the free compounds or in other synthetic manipulations. The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, cupric, cuprous, ferric, ferrous, lithium, magnesium, manganic, manganous, potassium, sodium, zinc and the like salts. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention are the specific compounds disclosed in the Examples and herein. The subject compounds may be useful in a method of treating a neurological or psychiatric disorder associated with PDE10 dysfunction in a patient such as a mammal in need of such inhibition comprising the administration of an effective amount of the compound. In addition to primates, especially humans, a variety of other mammals can be treated according to the method of the present invention. The subject compounds may be useful in a method of inhibiting PDE10 activity in a patient such as a mammal in need of such inhibition comprising the administration of an effective amount of the compound. The subject compounds may also be useful for treating a neurological or psychiatric disorder associated with striatal hypofunction or basal ganglia dysfunction in a mammalian patient in need thereof. In addition to primates, especially humans, a variety of other mammals may be treated according to the method of the present invention.

The present invention is directed to a compound of the present invention or a pharmaceutically acceptable salt thereof for use in medicine. The present invention is further directed to use of a compound of the present invention or a pharmaceutically acceptable salt thereof for the manufacture of a medicament for treating a neurological or psychiatric disorder associated with PDE10 dysfunction in a mammalian patient in need thereof. The present invention is further directed to a use of a compound of the present invention or a pharmaceutically acceptable salt thereof for the manufacture of a medicament for treating a neurological or psychiatric disorder associated with striatal hypofunction or basal ganglia dysfunction in a mammalian patient in need thereof.

"Treating" or "treatment of" a disease state includes: 1) preventing the disease state, i.e. causing the clinical symptoms of the disease state not to develop in a subject that may be exposed to or predisposed to the disease state, but does not yet experience or display symptoms of the disease state; 2) inhibiting the disease state, i.e., arresting the development of the disease state or its clinical symptoms; 3) or relieving the disease state, i.e., causing temporary or permanent regression of the disease state or its clinical symptoms.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy to retard the progression or reduce the risk of the noted conditions, particularly in a patient who is predisposed to such disease or disorder.

Applicants propose that inhibitors of PDE10 and, in particular inhibitors of PDE10A, may provide therapeutic benefit to those individuals suffering from psychiatric and cognitive disorders. The unique and exclusive distribution of PDE10A in the medium spiny projection neurons of the striatum, which form the principle site for cortical and dopaminergic input within basal ganglia, suggests that it may be possible and desirable to identify inhibitors of PDE10 to ameliorate or eliminate unwanted cellular signaling within this site. Without wishing to be bound by any theory, Applicants believe that inhibition of PDE10A in the striatum may result in increased cAMP/cGMP signaling and striatal output, which has the potential to restore behavioral inhibition that is impaired in cognitive disease such as schizophrenia. Regulation and integration of glutamatergic and dopaminergic inputs may enhance cognitive behavior, while suppressing or reducing unwanted behavior. Thus, in one embodiment, compounds of the invention may provide a method for treating or ameliorating diseases or conditions in which striatal hypofunction is a prominent feature or ones in which basal ganglia dysfunction plays a role, such as, Parkinson's disease, Huntington's disease, schizophrenia, obsessive-compulsive disorders, addiction and psychosis. Other conditions for which the inhibitors described herein may have a desirable and useful effect include those requiring a reduction in activity and reduced response to psychomotor stimulants or where it would be desirable to reduce conditional avoidance responses, which is often predictive of clinical antipsychotic activity.

As used herein, the term "'selective PDE10 inhibitor" refers to an organic molecule that effectively inhibits an enzyme from the PDE10 family to a greater extent than enzymes from the PDE 1-9 or PDE11 families. In one embodiment, a selective PDE10 inhibitor is an organic molecule having a Ki for inhibition of PDE10 that is less than or about one-tenth that for a substance that is an inhibitor for another PDE enzyme. In other words, the organic molecule inhibits PDE10 activity to the same degree at a concentration of about one-tenth or less than the concentration required for any other PDE enzyme. Preferably, a selective PDE10 inhibitor is an organic molecule, having a Ki for inhibition of PDE10 that is less than or about one-hundredth that for a substance that is an inhibitor for another PDE enzyme. In other words, the organic molecule inhibits PDE10 activity to the same degree at a concentration of about one-hundredth or less than the concentration required for any other PDE enzyme. A "selective PDE10 inhibitor" can be identified, for example, by comparing the ability of an organic molecule to inhibit PDE10 activity to its ability to inhibit PDE enzymes from the other PDE families. For example, an organic molecule may be assayed for its ability to inhibit PDE10 activity, as well as PDE1A, PDE1B, PDE1C, PDE2A, PDE3A, PDE3B, PDE4A, PDE4B, PDE4C, PDE4D, PDE5A, PDE6A, PDE6B, PDE6C, PDE7A, PDE7B, PDE8B, PDE9A, and/or PDE11A.

Phosphodiesterase enzymes including PDE10 have been implicated in a wide range of biological functions. This has suggested a potential role for these enzymes in a variety of disease processes in humans or other species. The compounds of the present invention have utility in treating a variety of neurological and psychiatric disorders.

In a specific embodiment, compounds of the present invention may provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention may provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temporal dementia, delirium, amnestic disorders or age related cognitive decline.

In another specific embodiment, compounds of the present invention may provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention may provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention may provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-10 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention may provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with post-partum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder (PDD), mood disorders due to a general medical condition, and substance-induced mood disorders.

In another specific embodiment, compounds of the present invention may provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, compounds of the invention may provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy. Of the disorders above, the treatment of schizophrenia, bipolar disorder, depression, including unipolar depression, seasonal depression and post-partum depression, premenstrual syndrome (PMS) and premenstrual dysphoric disorder (PDD), learning disorders, pervasive developmental disorders, including autistic disorder, attention disorders including Attention-Deficit/Hyperactivity Disorder, autism, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

The activity of the compounds in accordance with the present invention as PDE10 inhibitors may be readily determined without undue experimentation using a fluorescence polarization (FP) methodology that is well known in the art (Huang, W., et al., J. Biomol Screen, 2002, 7: 215). In particular, the compounds of the following examples had activity in reference assays by exhibiting the ability to inhibit the hydrolysis of the phosphosphate ester bond of a cyclic nucleotide. Any compound exhibiting a Ki (inhibitory constant) below 1 µM would be considered a PDE10 inhibitor as defined herein.

In a typical experiment the PDE10 inhibitory activity of the compounds of the present invention was determined in accordance with the following experimental method. PDE10A2 was amplified from human fetal brain cDNA (Clontech, Mountain View, Calif.) using a forward primer corresponding to nucleotides 56-77 of human PDE10A2 (Accession No. AF127480, Genbank Identifier 4894716), containing a Kozak consensus sequence, and a reverse primer corresponding to nucleotides 2406-2413 of human PDE10A2 (Accession No. AF127480, Genbank Identifier 4894716). Amplification with Easy-A polymerase (Stratagene, La Jolla, Calif.) was 95° C. for 2 minutes followed by thirty three cycles of 95° C. for 40 seconds, 55° C. for 30 seconds, and 72° C. for 2 minutes 48 seconds. Final extension was 72° C. for 7 minutes. The PCR product was TA cloned into pcDNA3.2-TOPO (Invitrogen, Carlsbad, Calif.) according to standard protocol. AD293 cells with 70-80% confluency were transiently transfected with human PDE10A2/pcDNA3.2-TOPO using Lipofectamine 2000 according to manufacturer specifications (Invitrogen, Carlsbad, Calif.). Cells were harvested 48 hours post-transfection and lysed by sonication (setting 3, 10×5 sec pulses) in a buffer containing 20 mM HEPES, 1 mM EDTA and protease inhibitor cocktail (Roche). Lysate was collected by centrifugation at 75,000×g for 20 minutes. Supernatant containing the cytoplasmic fraction was used for evaluation of PDE10A2 activity. The fluorescence polarization assay for cyclic nucleotide phosphodiesterases was performed using an IMAP® FP kit supplied by Molecular Devices, Sunnyvale, Calif. (product #R8139). IMAP® technology has been applied previously to phosphodiesterase assays (Huang, W., et al., J. Biomol Screen, 2002, 7: 215). Assays were performed at room temperature in 384-well microtiter plates with an incubation volume of 20.2 µL. Solutions of test compounds were prepared in DMSO and serially diluted with DMSO to yield 8 µL of each of 10 solutions differing by 3-fold in concentration, at 32 serial dilutions per plate. 100% inhibition is determined using a known PDE10 inhibitor, which can be any compound that is present at 5,000 times its Ki value in the assay described as follows, such as papaverine (see Siuciak, et al. Neuropharmacology (2006) 51:386-396; Becker, et al. Behav Brain Res (2008) 186(2):155-60; Threlfell, et al., J Pharmacol Exp Ther (2009) 328(3):785-795), 2-{4-[pyridin-4-yl-1-(2,2,2-trifluoroethyl)-1H-pyrazol-3-yl]phenoxymethyl}quinoline succinic acid or 2-[4-(1-methyl-4-pyridin-4-yl-1H-pyrazol-3-yl)-phenoxymethyl] quinoline succinic acid (see Schmidt, et al. J Pharmacol Exp Ther (2008) 325:681-690; Threlfell, et al., J Pharmacol Exp Ther (2009) 328(3): 785-795). 0% of inhibition is determined by using DMSO (1% final concentrations).

A Labcyte Echo 555 (Labcyte, Sunnyvale, Calif.) is used to dispense 200 nL from each well of the titration plate to the 384 well assay plate. A solution of enzyme (1/1600 dilution from aliquots; sufficient to produce 20% substrate conversion) and a separate solution of FAM-labeled cAMP PDE from Molecular Devices (product #R7506), at a final concentration of 50 nM are made in the assay buffer (10 mM Tris HCl, pH 7.2, 10 mM $MgCl_2$, 0.05% $NaN_3$ 0.01% Tween-20, and 1 mM DTT). The enzyme and the substrate are then added to the assay plates in two consecutive additions of 10 µL, and then shaken to mix. The reaction is allowed to proceed at room temperature for 30 minutes. A binding solution is then made from the kit components, comprised of 80% Solution A, 20% Solution B and binding reagent at a volume of 1/600 the total binding solution. The enzymatic reaction is stopped by addition of 60 µL of the binding solution to each well of the assay plates and the plates are sealed and shaken for 10 seconds. The plate was incubated at room temperature for at least one hour prior to determining the fluorescence polarization (FP). The parallel and perpendicular fluorescence of each well of the plate was measured using a Perkin Elmer EnVision™ plate reader (Waltham, Mass.).

Fluorescence polarization (mP) was calculated from the parallel (S) and perpendicular (P) fluorescence of each sample well and the analogous values for the median control well, containing only substrate (So and Po), using the following equation:

Polarization (mP)=1000*(S/So−P/Po)/(S/So+P/Po).

Dose-inhibition profiles for each compound were characterized by fitting the mP data to a four-parameter equation given below. The apparent inhibition constant ($K_I$), the maximum inhibition at the low plateau relative to "100% Inhibition Control" (Imax; e.g. 1=>same as this control), the minimum inhibition at the high plateau relative to the "0% Inhibition Control" (Imin, e.g. 0=>same as the no drug control) and the Hill slope (nH) are determined by a non-linear least squares fitting of the mP values as a function of dose of the compound using an in-house software based on the procedures described by Mosser et al., JALA, 2003, 8: 54-63, using the following equation:

$$mP = \frac{(0\% \ mP - 100\% \ mP)(Imax - Imin)}{1 + \left[\frac{[Drug]}{\left(10^{-pK_I}\left(1 + \frac{[Substrate]}{K_M}\right)\right)}\right]^{nH}} +$$

$$100\% \ mP + (0\% \ mP - 100\% \ mP)(1 - Imax)$$

The median signal of the "0% inhibition controls" (0% mP) and the median signal of the "100% inhibition controls" (100% mP) are constants determined from the controls located in columns 1-2 and 23-24 of each assay plate. An apparent ($K_m$) for FAM-labeled cAMP of 150 nM was determined in separate experiments through simultaneous variation of substrate and selected drug concentrations.

Selectivity for PDE10, as compared to other PDE families, was assessed using the IMAP® technology. Rhesus PDE2A3 and Human PDE10A2 enzyme was prepared from cytosolic fractions of transiently transfected HEK cells. All other PDE's were GST Tag human enzyme expressed in insect cells and were obtained from BPS Bioscience (San Diego, Calif.): PDE1A (Cat#60010), PDE3A (Cat#60030), PDE4A1A (Cat#60040), PDE5A1 (Cat#60050), PDE6C (Cat#60060), PDE7A (Cat#60070), PDE8A1 (Cat#60080), PDE9A2 (Cat#60090), PDE11A4 (Cat#60110).

Assays for PDE 1 through 11 were performed in parallel at room temperature in 384-well microtiter plates with an incubation volume of 20.2 µL. Solutions of test compounds were prepared in DMSO and serially diluted with DMSO to yield 30 µL of each of ten solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, Calif.) was used to dispense 200 nL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or FAM-labeled cGMP from Molecular Devices (Sunnyvale, Calif., product #R7506 or cGMP#R7508), at a final concentration of 50 nM were made in the assay buffer (10 mM Tris HCl, pH 7.2, 10 mM $MgCl_2$, 0.05% $NaN_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 µL and then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 µL of the binding solution to each well of the assay plate. The plates were sealed and shaken for 10 seconds. The plates were incubated at room temperature for one hour, then the parallel and perpendicular fluorescence was measured using a Tecan Genios Pro plate reader (Tecan, Switzerland). The apparent inhibition constants for the compounds against all 11 PDE's was determined from the parallel and perpendicular fluorescent readings as described for PDE10 FP assay using the following apparent $K_M$ values for each enzyme and substrate combination: PDE1A (FAM cGMP) 70 nM, rhesus PD2A3 (FAM cAMP) 10,000 nM, PDE3A (FAM cAMP) 50 nM, PDE4A1A (FAM cAMP) 1500 nM, PDE5A1 (FAM cGMP) 400 nM, PDE6C (FAM cGMP) 700 nM, PDE7A (FAM cAMP) 150 nM, PDE8A1 (FAM cAMP) 50 nM, PDE9A2 (FAM cGMP) 60 nM, PDE10A2 (FAM cAMP) 150 nM, PDE11A4 (FAM cAMP) 1000 nM. The intrinsic PDE10 inhibitory activity of a compound which may be used in accordance with the present invention may be determined by these assays.

All of the final compounds of the following examples had activity in inhibiting the human PDE10 enzyme in the aforementioned assays, generally with an Ki of less than about 1 µM. In particular, all of the final compounds of the following examples had activity in inhibiting the human PDE10 enzyme in the aforementioned assays, generally with an Ki of less than about 0.1 µM. Additional data is provided in the following Examples. Such a result is indicative of the intrinsic activity of the compounds in use as inhibitors of the PDE10 enzyme. In general, one of ordinary skill in the art would appreciate that a substance is considered to effectively inhibit PDE10 activity if it has a Ki of less than or about 1 M, preferably less than or about 0.1 µM. The present invention also includes compounds within the generic scope of the invention which possess activity as inhibitors of other phosphodiesterase enzymes. With respect to 2-alkoxy pyrimidine compounds, the present compounds exhibit unexpected properties, such as regarding increased potency, oral bioavailability, metabolic stability, and/or decreased off target activity.

The subject compounds are further useful in a method for the prevention, treatment, control, amelioration, or reduction of risk of the diseases, disorders and conditions noted herein. The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg. of body weight daily are administered to the patient, e.g., humans and elderly humans. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Several methods for preparing the compounds of this invention are illustrated in the following Schemes and Examples. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; Ac: acetyl; THF: tetrahydrofuran; Boc: tert-butyloxycarbonyl; DIPEA: N,N-diisopropylethylamine; DPPA: diphenylphosphorylazide; EDC: N-(3-Dimethylaminopropyl)-N'-ethylcarbodiimide; EtOAc: ethyl acetate; HOBt: hydroxybenzotriazole hydrate; TEA: triethylamine; DMF: N,N-dimethylformamide; rt: room temperature; HPLC: high performance liquid chromatography; NMR: nuclear magnetic resonance; TLC: thin-layer chromatography.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

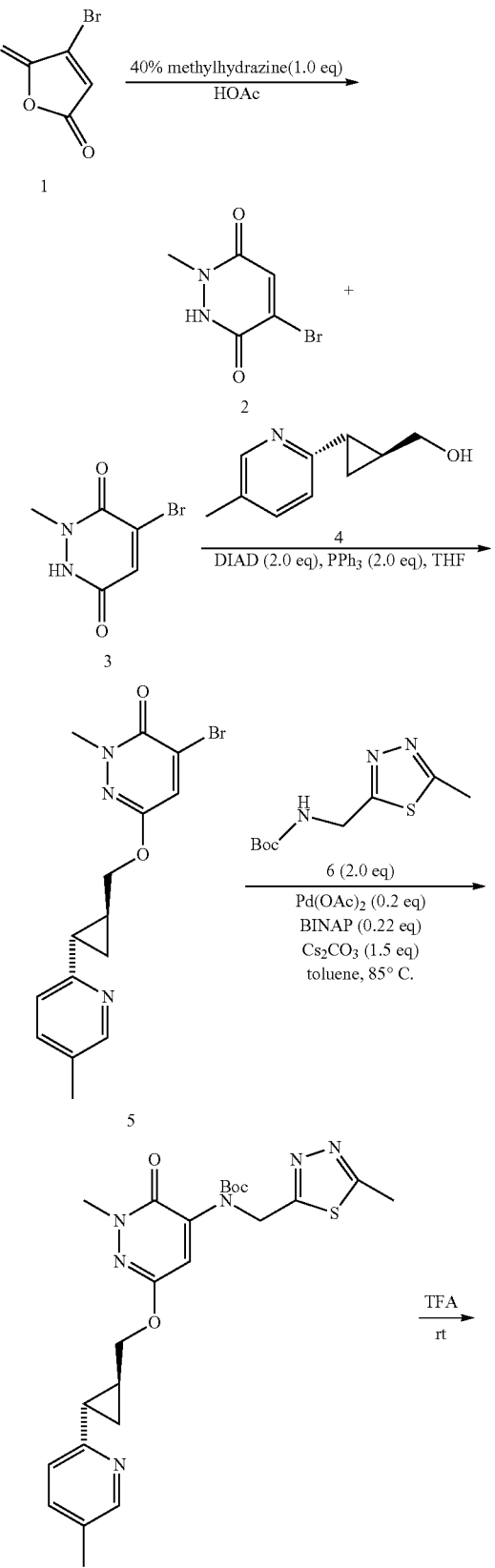

SCHEME 1

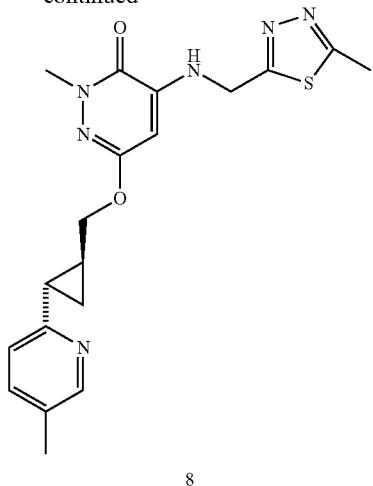

8

Example 1

Referring to Scheme 1

Step A:
5-bromo-1-methyl-1,2-dihydropyridazine-3,6-dione

To a solution of 1 (100 g, 0.565 mol) in HOAc (1.0 L) cooled in an ice-water bath, 40% aq. methylhydrazine solution (65 g, 0.565 mol) was added dropwise while the internal temperature was held below 20° C. The mixture was allowed to warm to rt and stirred for 16 h. The precipitated solid was collected by filtration, washed with EtOAc, and dried in vacuo to give 2 as a white solid. ESI-MS: 206.9 (M+H)+. $^1$H NMR (400 MHz, CD$_3$OD) δ: 7.35 (s, 1H), 3.60 (s, 3H).

The filtrate was concentrated to give the crude 3, which was purified by column chromatography on silica gel, eluting with PE/EA (1/2) to give 3 as a yellow solid. ESI-MS: 206.9 (M+H)+. $^1$H NMR (400 MHz, CD$_3$OD) δ: 7.57 (s, 1H), 3.67 (s, 3H).

Step B: 4-bromo-2-methyl-6-(((1S,2S)-2-(5-methylpyridin-2-yl)cyclopropyl)methoxy)pyridazin-3(2H)-one (5)

To a solution of 5-bromo-1-methyl-1,2-dihydropyridazine-3,6-dione (100 mg, 0.49 mmol) in THF (3 mL) at 0° C. was added triphenyl phosphorous (257 mg, 0.98 mmol) and ((1S,2S)-2-(5-methylpyridin-2-yl)cyclopropyl)methanol (4) (80 mg, 0.49 mmol) followed by dropwise addition of DIAD (198 mg, 0.98 mmol). The reaction mixture was warmed to ambient temperature. After stirred for 1 h, the mixture was concentrated. The residue was purified by column chromatography on silica gel, eluting with PE/EA (1/2) to give the title compound as oil.

Step C: tert-butyl (5-methyl-1,3,4-thiadiazol-2-yl)methyl(2-methyl-6-(((1S,2S)-2-(5-methyl pyridin-2-yl)cyclopropyl)methoxy)-3-oxo-2,3-dihydropyridazin-4-yl)carbamate (7)

A mixture of 4-bromo-2-methyl-6-(((1S,2S)-2-(5-methylpyridin-2-yl)cyclopropyl)methoxy)pyridazin-3(2H)-one (5) (90 mg, 0.26 mmol), tert-butyl (5-methyl-1,3,4-thiadiazol-2-yl)methylcarbamate (6) (119 mg, 0.52 mmol), Pd(OAc)$_2$ (9 mg, 0.052 mmol), BINAP (36 mg, 0.057 mmol) and Cs$_2$CO$_3$ (127 mg, 0.39 mmol) in toluene (4 mL) under N$_2$ was heated at 85° C. for 20 h. After cooled to rt, The mixture was diluted with EtOAc (20 mL), washed with H$_2$O and brine, dried over MgSO$_4$, filtered and concentrated in vacuo. The residue was purified by column chromatography on silica gel, eluting with PE/EA (1/2) to give the title compound as a oil.

Step D: 2-methyl-4-((5-methyl-1,3,4-thiadiazol-2-yl)methylamino)-6-(((1S,2S)-2-(5-methyl pyridin-2-yl)cyclopropyl)methoxy)pyridazin-3(2H)-one (8)

A solution of tert-butyl (5-methyl-1,3,4-thiadiazol-2-yl)methyl(2-methyl-6-(((1S,2S)-2-(5-methyl pyridin-2-yl)cyclopropyl)methoxy)-3-oxo-2,3-dihydropyridazin-4-yl)carbamate (7) (95 mg, 0.19 mmol) in TFA (1 mL) was stirred at room temperature for 1 h. The reaction mixture was concentrated and 10 mL sat. aq. NaHCO$_3$ was added, extracted with EA (3×10 mL). The organic phase was dried with anhydrous Na$_2$SO$_4$, filtered and concentrated. The residue was purified by Prep-TLC using PE/EtOAc=1/2 to give title compound as a oil. $^1$H NMR (400 MHz, DMSO) δ 8.23 (s, 1H), 7.55 (t, 1H), 7.45 (d, 1H), 7.18 (d, 1H), 5.86 (s, 1H), 4.73-4.71 (m, 2H), 4.09-4.04 (m, 1H), 3.97-3.97 (m, 1H), 3.51 (s, 3H), 2.66 (s, 3H), 2.22 (s, 3H), 2.11-2.05 (m, 1H), 1.72-1.68 (m, 1H), 1.14-1.09 (m, 1H), 0.99-0.94 (m, 1H); LRMS m/z (M+H) 399.2 found, 399.15 required.

SCHEME 2

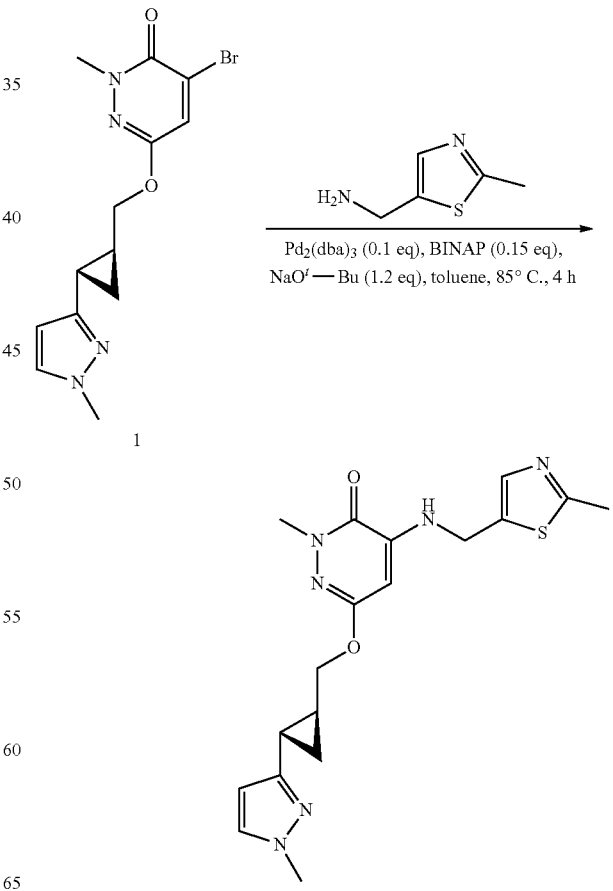

Example 2

Step A: 2-methyl-6-((((1S,2S)-2-(1-methyl-1H-pyrazol-3-yl)cyclopropyl)methoxy)-4-((2-methylthiazol-5-yl)methylamino)pyridazin-3(2H)-one To the solution of 4-bromo-2-methyl-6-(((1S,2S)-2-(1-methyl-1H-pyrazol-3-yl)cyclo propyl)methoxy)pyridazin-3(2H)-one (made according to Example 1, by replacing ((1S,2S)-2-(5-methylpyridin-2-yl)cyclopropyl)methanol with (((1S,2S)-2-(1-methyl-1H-pyrazol-3-yl)cyclopropyl)methanol, 27 mg, 0.08 mmol) in toluene (2 mL) under $N_2$, (2-methylthiazol-5-yl)methanamine (13 mg, 0.096 mmol), $Pd_2(dba)_3$ (7 mg, 0.008 mmol), BINAP (7 mg, 0.012 mmol) and NaO$^t$Bu (9 mg, 0.096 mmol) were added. After the reaction mixture was stirred at 85° C. for 4 h, 15 mL water was added. The mixture was extracted with EtOAc (3×10 mL). The combined organics were dried over $MgSO_4$, filtered and concentrated in vacuo. The residue was purified by reverse phase chromatography (X bridge Prep C18OBD, 40-60% acetonitrile in water with 10 mmol $NH_4HCO_3$ modifier) to afford the title compound as an oil. $^1$H NMR (400 MHz, MeOD) δ 7.56 (s, 1H), 7.42 (d, 1H), 5.96 (d, 1H), 5.89 (s, 1H), 4.59 (s, 2H), 4.15-5.11 (m, 1H), 4.04-4.01 (m, 1H), 3.81 (s, 3H), 3.63 (s, 3H), 2.66 (s, 3H), 1.95-1.89 (m, 1H), 1.61-1.53 (m, 1H), 1.01-0.95 (m, 2H); LRMS m/z (M+H) 387.1 found, 387.15 required.

The following Examples 3-7 were prepared using the procedure of Example 1, substituting the appropriate starting materials.

The following Examples 8-34 were prepared using the procedure of Example 2, substituting the appropriate starting materials.

TABLE 1

| Example | Structure | IUPAC Name | LCMS m/z [M + H]$^+$ |
|---|---|---|---|
| 3 | 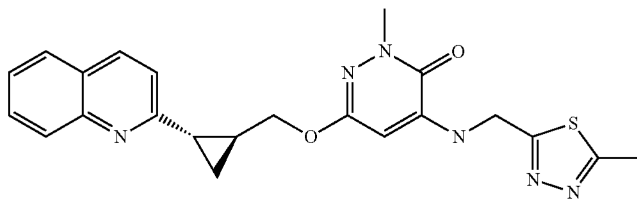 [SMILES: Cc1nnc(CNc2cc(OC[C@H]3C[C@@H]3c3ccc4ccccc4n3)nn(C)c2=O)s1] | 2-methyl-4-((5-methyl-1,3,4-thiadiazol-2-yl)-methylamino)-6-(((1S,2S)-2-(quinolin-2-yl)cyclopropyl)methoxy)pyridazin-3(2H)-one | 435.1 |
| 4 | 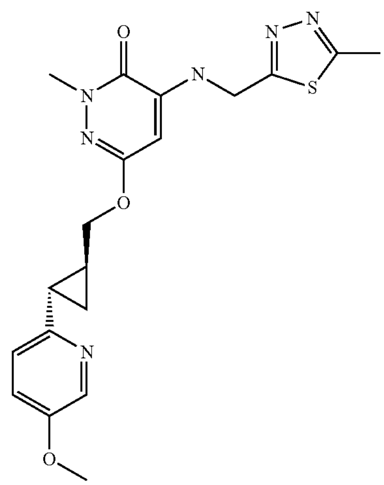 [SMILES: COc1ccc([C@H]2C[C@@H]2COc2cc(NCc3nnc(C)s3)c(=O)n(C)n2)nc1] | 6-(((1S,2S)-2-(5-methoxypyridin-2-yl)cyclopropyl-)-methoxy)-2-methyl-4-((5-methyl-1,3,4-thiadiazol-2-yl)methylamino)pyridazin-3(2H)-one | 415.1 |
| 5 | 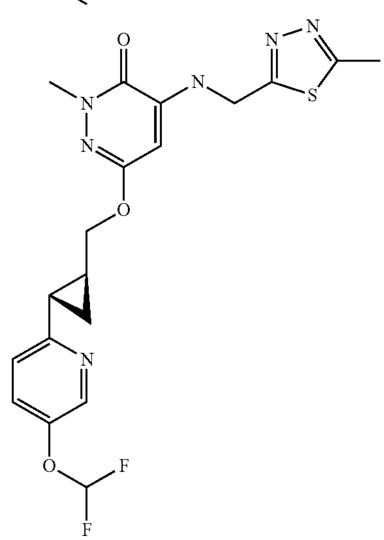 | 6-(((1S,2S)-2-(5-(difluoromethoxy)pyridin-2-yl)cyclopropyl)methoxy-)-2-methyl-4-((5-methyl-1,3,4-thiadiazol-2-yl)-methylamino)pyridazin-3(2H)-one | 451.1 |

TABLE 1-continued

| Example | Structure | IUPAC Name | LCMS m/z [M + H]+ |
|---|---|---|---|
| 6 | 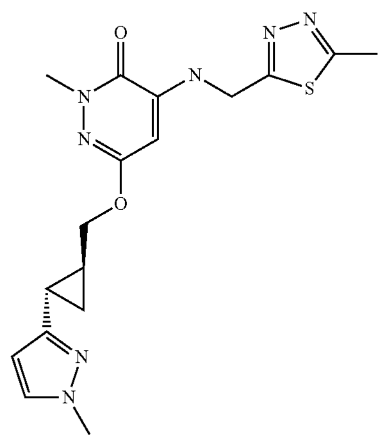 [SMILES: Cc1nnc(CNc2cc(OC[C@H]3C[C@@H]3c3ccn(C)n3)nn(C)c2=O)s1] | 2-methyl-4-((5-methyl-1,3,4-thiadiazol-2-yl)-methylamino)-6-(((1S,2S)-2-(1-methyl-1H-pyrazol-3-yl)cyclopropyl)methoxy)-pyridazin-3(2H)-one | 388.1 |
| 7 | 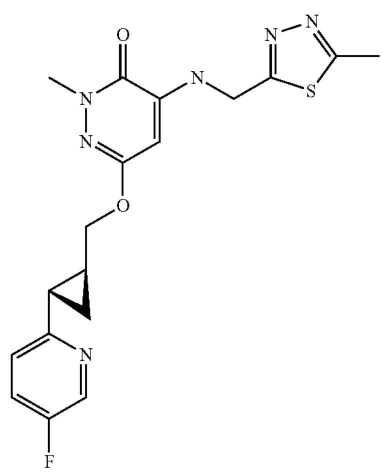 [SMILES: Cc1nnc(CNc2cc(OC[C@H]3C[C@@H]3c3ccc(F)cn3)nn(C)c2=O)s1] | 6-(((1S,2S)-2-(5-fluoropyridin-2-yl)cyclopropyl)methoxy)-2-methyl-4-((5-methyl-1,3,4-thiadiazol-2-yl)methylamino)pyridazin-3(2H)one | 403.1 |
| 8 | 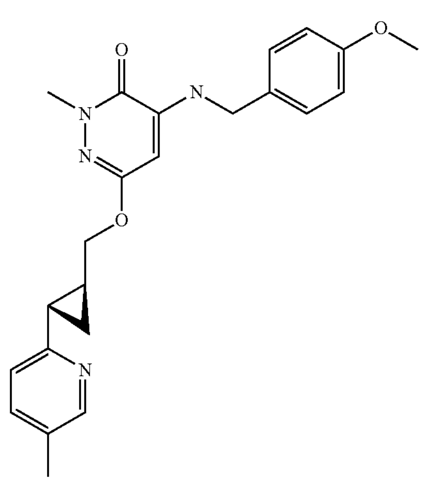 [SMILES: COc1ccc(CNc2cc(OC[C@H]3C[C@@H]3c3ccc(C)cn3)nn(C)c2=O)cc1] | 4-(4-methoxybenzylamino)-2-methyl-6-(((1S,2S)-2-(5-methylpyridin-2-yl)cyclopropyl)methoxy)-pyridazin-3(2H)-one | 407.1 |

TABLE 1-continued

| Example | Structure | IUPAC Name | LCMS m/z [M + H]⁺ |
|---|---|---|---|
| 9 | 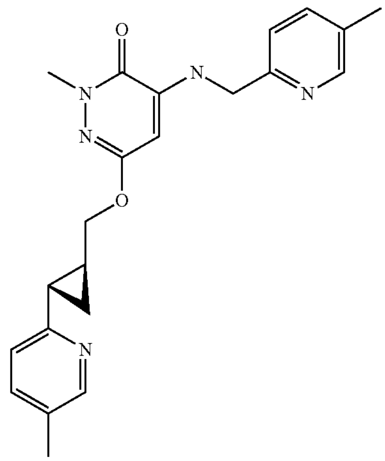 [SMILES: Cc1ccc(CNc2cc(OC[C@H]3C[C@@H]3c3ccc(C)cn3)nn(C)c2=O)nc1] | 2-methyl-6-(((1S,2S)-2-(5-methylpyridin-2-yl)cyclopropyl)methoxy)-4-((5-methylpyridin-2-yl)methylamino)pyridazin-3(2H)-one | 392.1 |
| 10 | 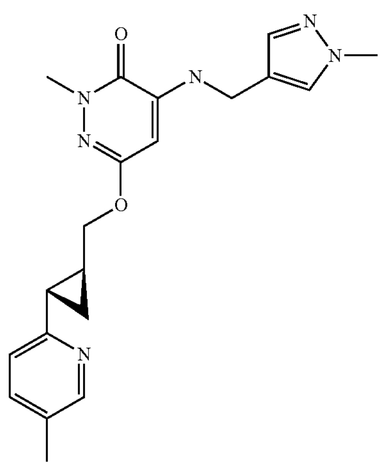 [SMILES: Cc1ccc([C@H]2C[C@@H]2COc2cc(NCc3cnn(C)c3)c(=O)n(C)n2)nc1] | 2-methyl-4-((1-methyl-1H-pyrazol-4-yl)methylamino)-6-(((1S,2S)-2-(5-methylpyridin-2-yl)cyclopropyl)methoxy)-pyridazin-3(2H)-one | 381.1 |
| 11 | 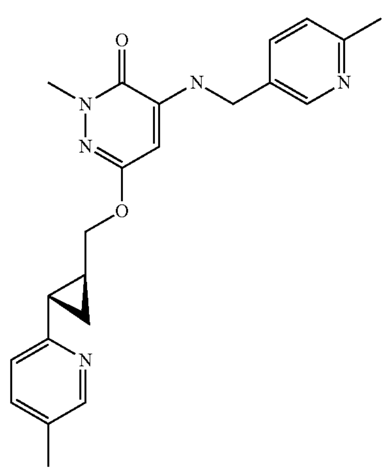 [SMILES: Cc1ccc([C@H]2C[C@@H]2COc2cc(NCc3ccc(C)nc3)c(=O)n(C)n2)nc1] | 2-methyl-6-(((1S,2S)-2-(5-methylpyridin-2-yl)cyclopropyl)methoxy)-4-((6-methylpyridin-3-yl)methylamino)pyridazin-3(2H)-one | 392.1 |

TABLE 1-continued
| Example | Structure | IUPAC Name | LCMS m/z [M + H]+ |
|---|---|---|---|
| 12 | 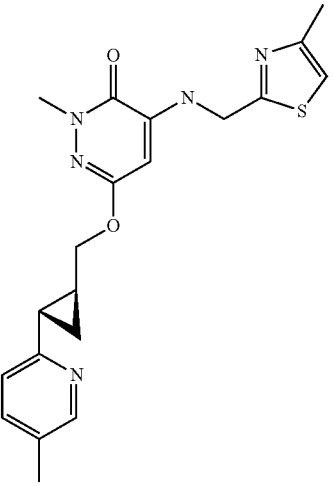 [SMILES: Cc1ccc([C@H]2C[C@@H]2COc2cc(NCc3nc(C)cs3)c(=O)n(C)n2)nc1] | 2-methyl-6-(((1S,2S)-2-(5-methylpyridin-2-yl)cyclopropyl)methoxy)-4-((4-methylthiazol-2-yl)methylamino)pyridazin-3(2H)one | 398.1 |
| 13 | 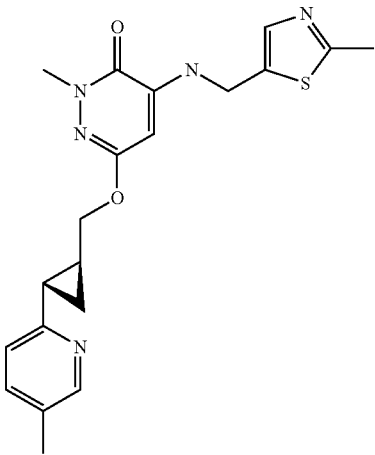 [SMILES: Cc1ccc([C@H]2C[C@@H]2COc2cc(NCc3cnc(C)s3)c(=O)n(C)n2)nc1] | 2-methyl-6-(((1S,2S)-2-(5-methylpyridin-2-yl)cyclopropyl)methoxy)-4-((2-methylthiazol-5-yl)methylamino)pyridazin-3(2H)-one | 398.1 |
| 14 | 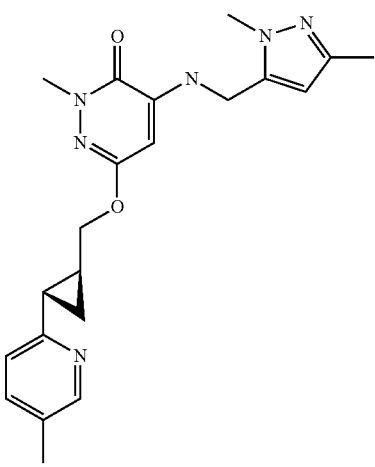 [SMILES: Cc1ccc([C@H]2C[C@@H]2COc2cc(NCc3cc(C)nn3C)c(=O)n(C)n2)nc1] | 4-((1,3-dimethyl-1H-pyrazol-5-yl)methylamino-)-2-methyl-6-(((1S,2S)-2-(5-methylpyridin-2-yl)cyclopropyl)methoxy)-pyridazin-3(2H)-one | 395.1 |

TABLE 1-continued

| Example | Structure | IUPAC Name | LCMS m/z [M + H]+ |
|---------|-----------|------------|-------------------|
| 15 | 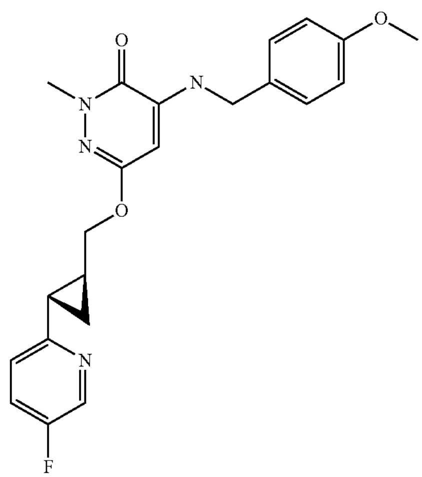 [SMILES: COc1ccc(CNc2cc(OC[C@H]3C[C@@H]3c3ccc(F)cn3)nn(C)c2=O)cc1] | 6-(((1S,2S)-2-(5-fluoro-pyridin-2-yl)-cyclopropyl-)-methoxy)-4-(4-methoxy-benzylamino)-2-methyl-pyridazin-3(2H)-one | 411.1 |
| 16 | 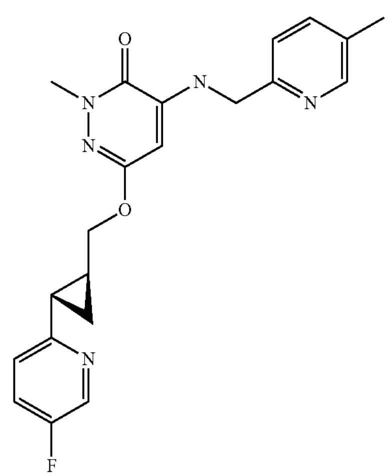 [SMILES: Cc1ccc(CNc2cc(OC[C@H]3C[C@@H]3c3ccc(F)cn3)nn(C)c2=O)nc1] | 6-(((1S,2S)-2-(5-fluoropyridin-2-yl)cyclopropyl)methoxy)-2-methyl-4-((5-methylpyridin-2-yl)methylamino)pyridazin-3(2H)-one | 396.1 |
| 17 | 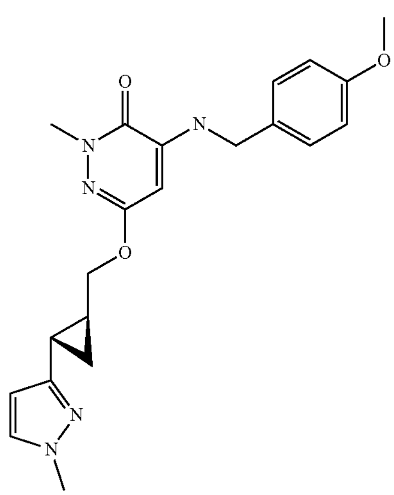 [SMILES: COc1ccc(CNc2cc(OC[C@H]3C[C@@H]3c3ccn(C)n3)nn(C)c2=O)cc1] | 4-(4-methoxybenzylamino)-2-methyl-6-(((1S,2S)-2-(1-methyl-1H-pyrazol-3-yl)cyclopropyl)methoxy)-pyridazin-3(2H)-one | 396.1 |

TABLE 1-continued

| Example | Structure | IUPAC Name | LCMS m/z [M + H]+ |
|---|---|---|---|
| 18 | 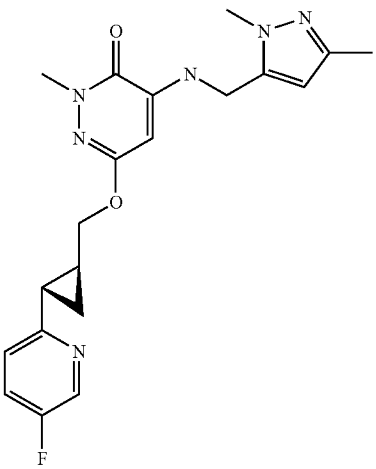 [SMILES: Cc1cc(CNc2cc(OC[C@H]3C[C@@H]3c3ccc(F)cn3)nn(C)c2=O)n(C)n1] | 4-(4-(((1S,2S)-2-(5-(difluoromethoxy)pyridin-2-yl)cyclopropyl)-methoxy)-2-methyl-pyrimidin-5-yl)-1-methylpyridin-2(1H)-one | 399.1 |
| 19 | 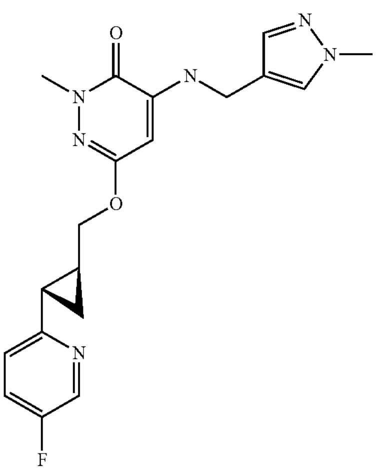 [SMILES: Cn1cc(CNc2cc(OC[C@H]3C[C@@H]3c3ccc(F)cn3)nn(C)c2=O)cn1] | 6-(((1S,2S)-2-(5-fluoropyridin-2-yl)cyclo-propyl)methoxy)-2-methyl-4-((1-methyl-1H-pyrazol-4-yl)methylamino-)-pyridazin-3(2H)-one | 385.1 |
| 20 | 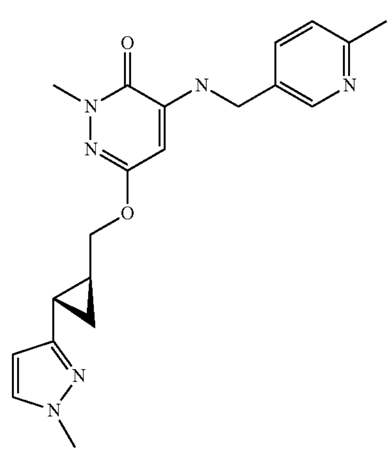 [SMILES: Cc1ccc(CNc2cc(OC[C@H]3C[C@@H]3c3ccn(C)n3)nn(C)c2=O)cn1] | 2-methyl-6-(((1S,2S)-2-(1-methyl-1H-pyrazol-3-yl)cyclopropyl)methoxy)-4-((6-methylpyridin-3-yl)methylamino)pyridazin-3(2H)-one | 381.1 |

TABLE 1-continued

| Example | Structure | IUPAC Name | LCMS m/z [M + H]+ |
|---|---|---|---|
| 21 | 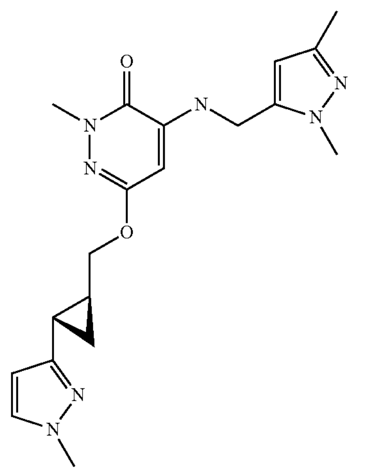 [SMILES: Cc1cc(CNc2cc(OC[C@H]3C[C@@H]3c3ccn(C)n3)nn(C)c2=O)n(C)n1] | 4-((1,3-dimethyl-1H-pyrazol-5-yl)methylamino)-2-methyl-6-(((1S,2S)-2-(1-methyl-1H-pyrazol-3-yl)cyclopropyl)methoxy)-pyridazin-3(2H)-one | 384.1 |
| 22 | 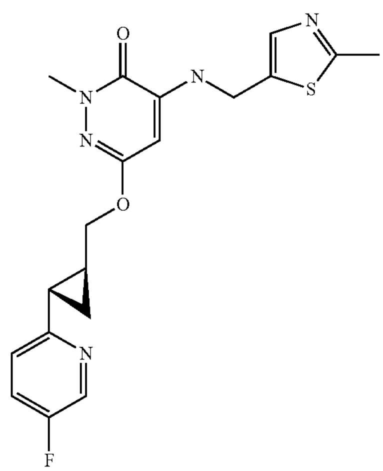 [SMILES: Cc1ncc(CNc2cc(OC[C@H]3C[C@@H]3c3ccc(F)cn3)nn(C)c2=O)s1] | 6-(((1S,2S)-2-(5-fluoropyridin-2-yl)cyclopropyl)methoxy)-2-methyl-4-((2-methylthiazol-5-yl)methylamino)pyridazin-3(2H)-one | 402.3 |
| 23 | 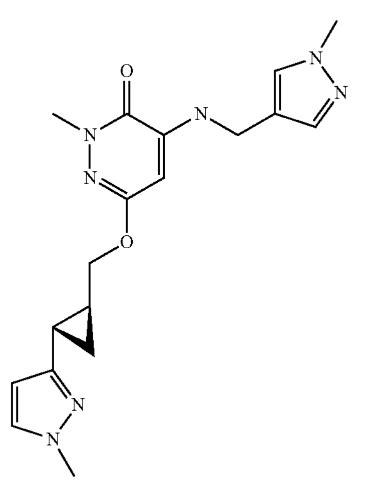 [SMILES: Cn1cc(CNc2cc(OC[C@H]3C[C@@H]3c3ccn(C)n3)nn(C)c2=O)cn1] | 2-methyl-6-(((1S,2S)-2-(1-methyl-1H-pyrazol-3-yl)cyclopropyl)methoxy)-4-((1-methyl-1H-pyrazol-4-yl)methylamino)-pyridazin-3(2H)-one | 370.1 |

TABLE 1-continued

| Example | Structure | IUPAC Name | LCMS m/z [M + H]+ |
|---|---|---|---|
| 24 | 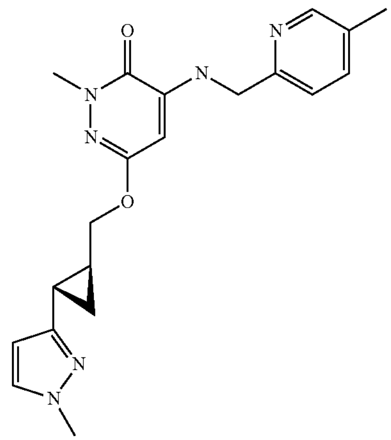 [SMILES: Cc1ccc(CNc2cc(OC[C@H]3C[C@@H]3c3ccn(C)n3)nn(C)c2=O)nc1] | 2-methyl-6-((((1S,2S)-2-(1-methyl-1H-pyrazol-3-yl)-cyclopropyl)methoxy)-4-((5-methylpyridin-2-yl)-methylamino)pyridazin-3(2H)-one | 381.1 |
| 25 | 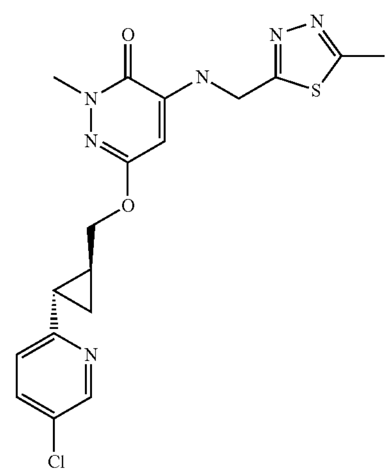 [SMILES: Cc1nnc(CNc2cc(OC[C@H]3C[C@@H]3c3ccc(Cl)cn3)nn(C)c2=O)s1] | 6-(((1S,2S)-2-(5-chloropyridin-2-yl)cyclopropyl)methoxy)-2-methyl-4-((5-methyl-1,3,4-thiadiazol-2-yl)methylamino)pyridazin-3(2H)-one | 419.1 |
| 26 | 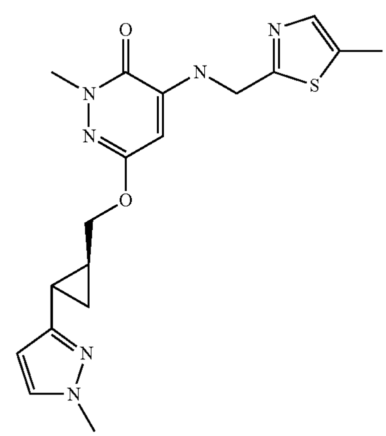 [SMILES: Cc1cnc(CNc2cc(OC[C@H]3CC3c3ccn(C)n3)nn(C)c2=O)s1] | 2-methyl-6-((((1S,2S)-2-(1-methyl-1H-pyrazol-3-yl)cyclopropyl)methoxy)-4-((5-methylthiazol-2-yl)methylamino)pyridazin-3(2H)-one | 387.1 |

TABLE 1-continued

| Example | Structure | IUPAC Name | LCMS m/z [M + H]+ |
|---|---|---|---|
| 27 | 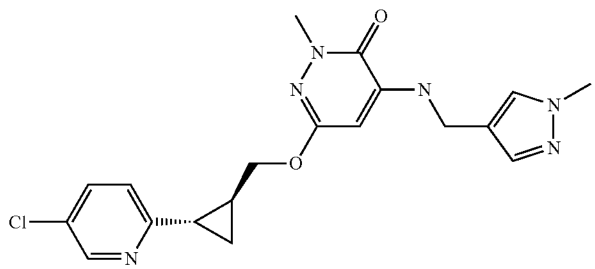 [SMILES: Cn1cc(CNc2cc(OC[C@H]3C[C@@H]3c3ccc(Cl)cn3)nn(C)c2=O)cn1] | 6-(((1S,2S)-2-(5-chloro-pyridin-2-yl)cyclopropyl)-methoxy)-2-methyl-4-((1-methyl-1H-pyrazol-4-yl)methylamino)pyridazin-3(2H)-one | 401.1 |
| 28 | 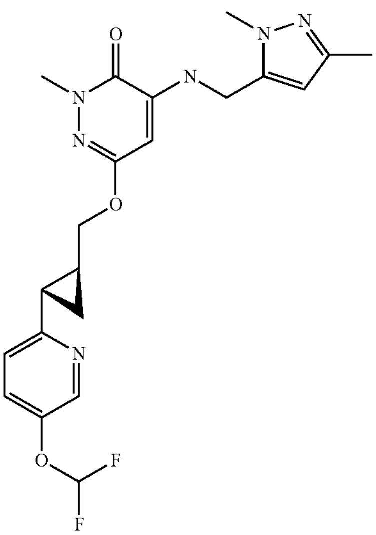 [SMILES: Cc1cc(CNc2cc(OC[C@H]3C[C@@H]3c3ccc(OC(F)F)cn3)nn(C)c2=O)n(C)n1] | 6-(((1S,2S)-2-(5-(difluoro-methoxy)pyridin-2-yl)-cyclopropyl)-methoxy)-4-((1,3-dimethyl-1H-pyrazol-5-yl)methyl-amino)-2-methylpyridazin-3(2H)one | 447.1 |
| 29 | 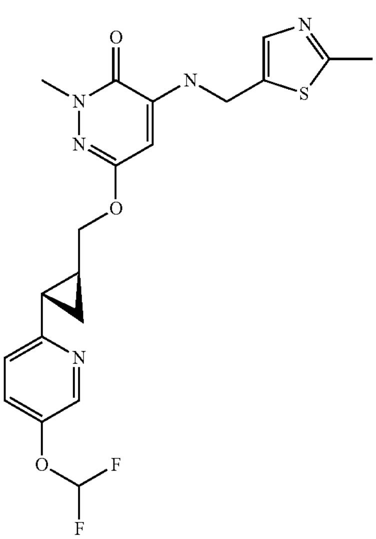 [SMILES: Cc1ncc(CNc2cc(OC[C@H]3C[C@@H]3c3ccc(OC(F)F)cn3)nn(C)c2=O)s1] | 6-(((1S,2S)-2-(5-(difluoromethoxy)pyridin-2-yl)cyclopropyl)-methoxy)-2-methyl-4-((2-methylthiazol-5-yl)methyl-amino)pyridazin-3(2H)one | 450.1 |

TABLE 1-continued

| Example | Structure | IUPAC Name | LCMS m/z [M + H]+ |
|---|---|---|---|
| 30 | 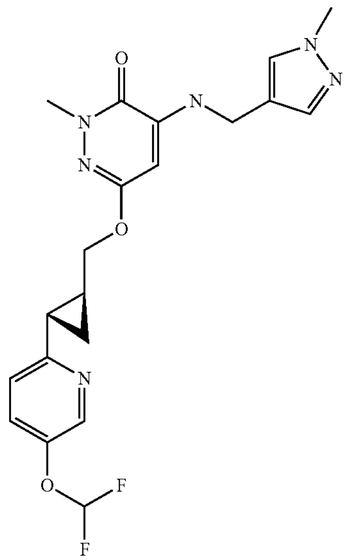 [SMILES: Cn1cc(CNc2cc(OC[C@H]3C[C@@H]3c3ccc(OC(F)F)cn3)nn(C)c2=O)cn1] | 6-(((1S,2S)-2-(5-(difluoromethoxy)pyridin-2-yl)cyclopropyl)methoxy)-2-methyl-4-((1-methyl-1H-pyrazol-4-yl)methylamino)pyridazin-3(2H)-one | 433.1 |
| 31 | 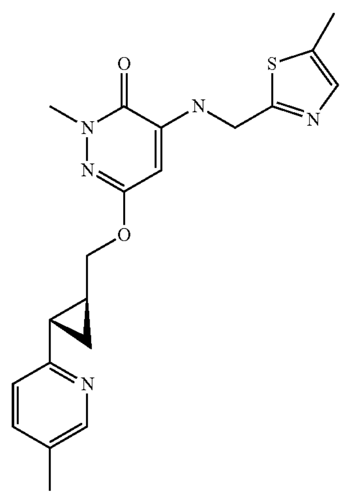 [SMILES: Cc1ccc([C@H]2C[C@@H]2COc2cc(NCc3ncc(C)s3)c(=O)n(C)n2)nc1] | 2-methyl-6-(((1S,2S)-2-(5-methylpyridin-2-yl)cyclopropyl)methoxy)-4-((5-methylthiazol-2-yl)methylamino)pyridazin-3(2H)-one | 398.1 |
| 32 | 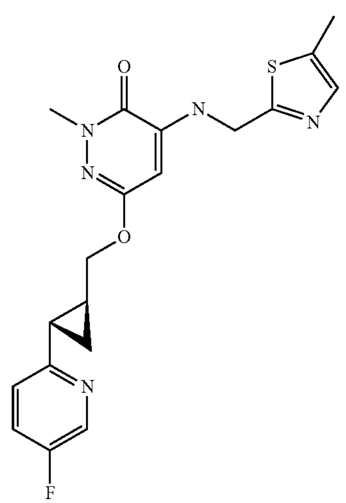 [SMILES: Cc1cnc(CNc2cc(OC[C@H]3C[C@@H]3c3ccc(F)cn3)nn(C)c2=O)s1] | 6-(((1S,2S)-2-(5-fluoropyridin-2-yl)cyclopropyl)methoxy)-2-methyl-4-((5-methylthiazol-2-yl)methylamino)pyridazin-3(2H)-one | 402.1 |

TABLE 1-continued

| Example | Structure | IUPAC Name | LCMS m/z [M + H]+ |
|---|---|---|---|
| 33 | 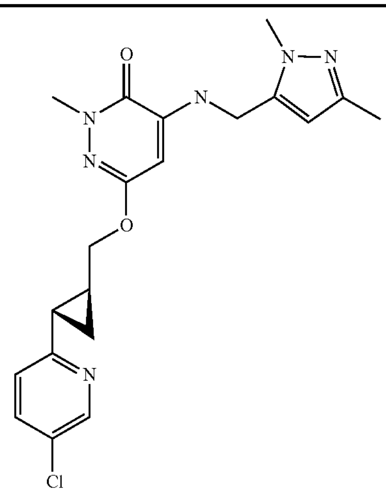 | 6-(((1S,2S)-2-(5-chloropyridin-2-yl)cyclopropyl)methoxy)-4-((1,3-dimethyl-1H-pyrazol-5-yl)methylamino)-2-methylpyridazin-3(2H)-one | 415.1 |
| 34 | 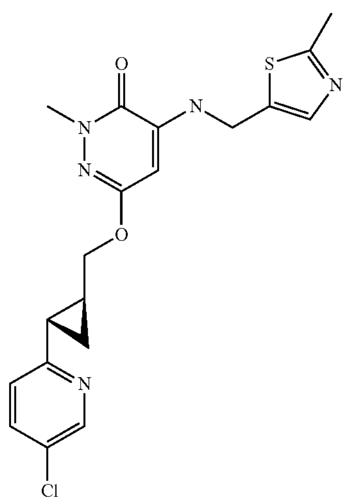 [SMILES: Cc1ncc(CNc2cc(OC[C@H]3C[C@@H]3c3ccc(Cl)cn3)nn(C)c2=O)s1] | 6-(((1S,2S)-2-(5-chloropyridin-2-yl)cyclopropyl)methoxy)-2-methyl-4-((2-methylthiazol-5-yl)methylamino)pyridazin-3(2H)-one | 418.1 |

Example 35

Step A: 4-((4-chloro-1,3-dimethyl-1H-pyrazol-5-yl)methylamino)-2-methyl-6-(((1S,2S)-2-(5-methylpyridin-2-yl)cyclopropyl)methoxy)pyridazin-3(2H)-one To a solution of 4-((1,3-dimethyl-1H-pyrazol-5-yl)methylamino)-2-methyl-6-(((1S,2S)-2-(5-methylpyridin-2-yl)cyclopropyl)methoxy)pyridazin-3(2H)-one (10 mg, 0.025 mmol) in 1,2-Dichloroethane (2.0 mL) was added NCS (4.0 mg, 0.030 mmol). After stirred for 1 h at rt, the reaction mixture was concentrated. The residue was purified by reverse phase chromatography (X bridge Prep C18OBD, 40-60% acetonitrile in water with 10 mmol $NH_4HCO_3$ modifier) to obtain product. 1H NMR (400 MHz, MeOD) δ 8.21 (s, 1H), 7.53 (d, 1H), 7.14 (d, 1H), 5.91 (s, 1H), 4.42 (s, 2H), 4.21-4.16 (m, 1H), 4.11-4.06 (m, 1H), 3.79 (s, 3H), 3.63 (s, 3H), 2.31 (s, 3H), 2.19 (s, 3H), 2.12-2.06 (m, 1H), 1.82-1.79 (m, 1H), 1.25-1.20 (m, 1H), 1.10-1.05 (m, 1H); LRMS m/z (M+H) 429.1 found, 429.17 required.

TABLE 2

| Example | L # | Structure | IUPAC Name | LCMS m/z [M + H]+ |
|---|---|---|---|---|
| 35 | L-005210770 | 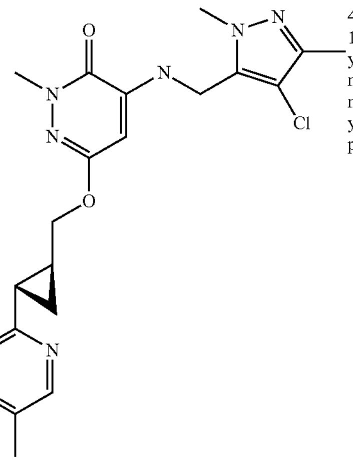 | 4-((4-chloro-1,3-dimethyl-1H-pyrazol-5-yl)methylamino)-2-methyl-6-(((1S,2S)-2-(5-methylpyridin-2-yl)cyclopropyl)methoxy)-pyridazin-3(2H)-one | 429.1 |

Example 36

Step A: 1. 2-methyl-4-(methyl((5-methyl-1,3,4-thiadiazol-2-yl)methyl)amino)-6-(((1S,2S)-2-(quinolin-2-yl)cyclopropyl)methoxy)pyridazin-3(2H)-one To a solution of 2-methyl-4-(methyl((5-methyl-1,3,4-thiadiazol-2-yl)methyl)amino)-6-(((1S,2S)-2-(quinolin-2-yl)cyclopropyl)methoxy)pyridazin-3(2H)-one (50 mg, 0.12 mmol) in THF (4.0 mL) was added NaH (10 mg, 0.24 mmol). After stirred for 30 min, CH$_3$I (26 mg, 0.18 mmol) was added. After the reaction mixture was stirred for another 16 h, water was carefully added and the mixture was extracted with EtOAc (2×10 mL). The combined organics were dried over MgSO$_4$, filtered and concentrated. The residue was purified by Prep-TLC using PE/EtOAc=1/1 to give title compound. $^1$H NMR (400 MHz, MeOD) δ 8.21 (d, 1H), 7.94 (d, 1H), 7.87 (d, 1H), 7.72 (t, 1H), 7.52 (t, 1H), 7.32 (d, 1H), 6.13 (s, 1H), 5.29 (s, 2H), 4.35-4.30 (m, 1H), 4.16-4.11 (m, 1H), 3.65 (s, 3H), 2.90 (s, 3H), 2.75 (s, 3H), 2.38-2.33 (m, 1H), 2.09-2.01 (m, 1H), 1.50-1.46 (m, 1H), 1.27-1.22 (m, 1H); LRMS m/z (M+H) 449.1 found, 449.17 required.

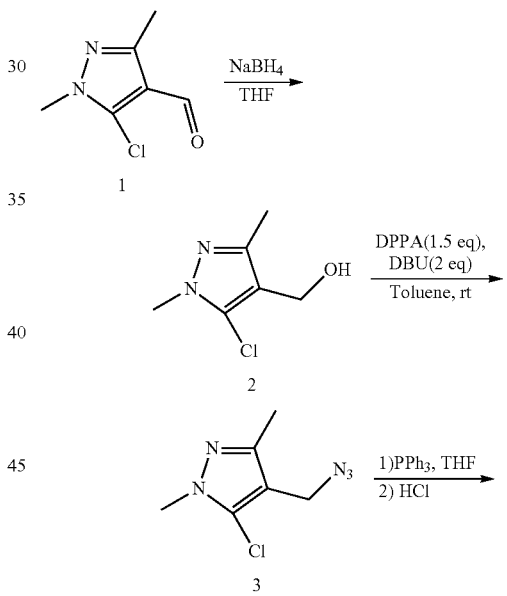

Scheme 3

TABLE 3

| Example | Structure | IUPAC Name | LCMS m/z [M + H]+ |
|---|---|---|---|
| 36 | 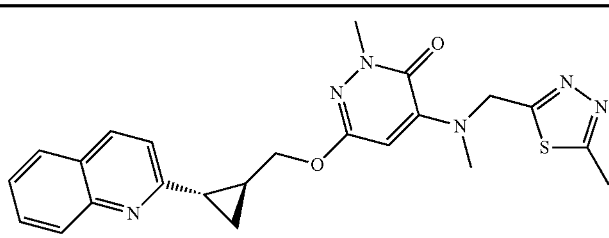 | 2-methyl-4-(methyl((5-methyl-1,3,4-thiadiazol-2-yl)methyl)amino)-6-(((1S,2S)-2-(quinolin-2-yl)cyclopropyl)methoxy)-pyridazin-3(2H)-one | 449.1 |

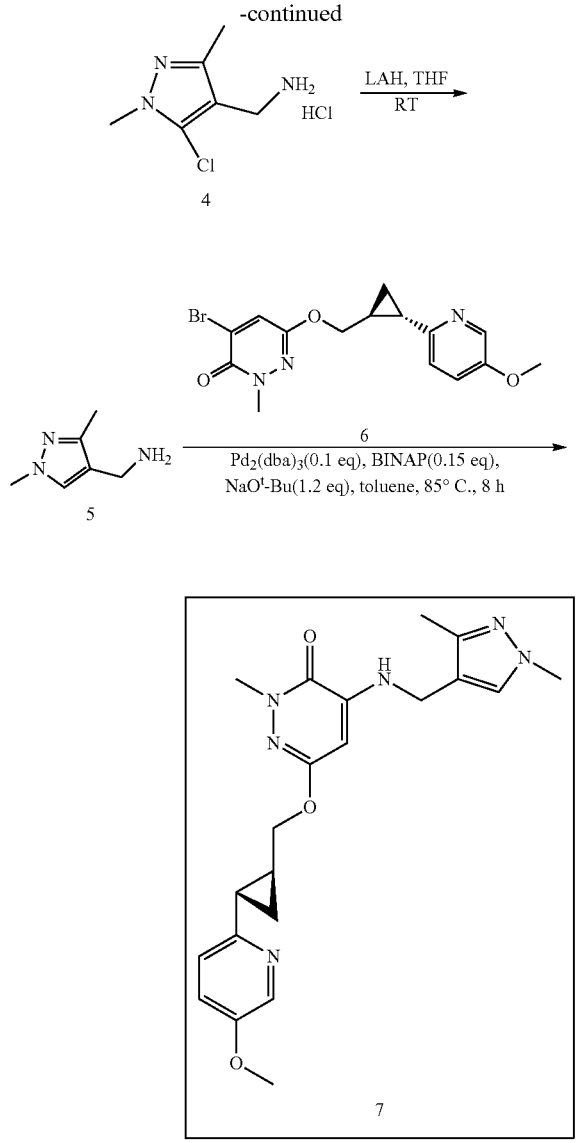

Example 37

Referring to Scheme 3

Step A: (5-chloro-1,3-dimethyl-1H-pyrazol-4-yl)methanol (2)

To a solution of compound 1 (632 mg, 4 mmol) in THF (20 mL) was added NaBH₄ (456 mg, 12 mmol). The reaction mixture was stirred at room temperature overnight and then saturated aqueous solution of NH₄Cl was added. The mixture was extracted with EA and the combined organic layer was washed with brine, dried over anhydrous sodium sulfate, filtered and concentrated under reduced pressure to give white solid which was used to next step without further purification. LCMS (ESI) m/z=161 (M+H)⁺.

Step B: 4-(azidomethyl)-5-chloro-1,3-dimethyl-1H-pyrazole (3)

To a solution of compound 2 (538 mg, 3.36 mmol) in toluene (10 mL) was added DPPA (1.1 mL, 5.04 mmol) and DBU (0.6 mL, 6.72 mmol) at 0° C. After stirring for 1 hr, the reaction mixture was warmed to room temperature and stirred for 24 hr. EA (20 mL) was added and the mixture was washed with water, brine, concentrated to give a yellow solid which was used without further purification. LCMS (ESI) m/z=186 (M+H)⁺.

Step C: (5-chloro-1,3-dimethyl-1H-pyrazol-4-yl)methanamine hydrochloride (4)

To a solution of compound 3 (175 mg, 0.95 mmol) in THF (5 mL) was added PPh₃ (248 mg, 0.95 mmol) at 0° C. After stirring for 1 hr, water (0.03 mL) and NH₄OH (0.07 mL) were added sequentially and the resulting mixture was stirred at room temperature for overnight. After the solvent was evaporated, the residue was purified with reversed flash to give a white solid. LCMS (ESI) m/z=160 (M+H)⁺.

Step D: (1,3-dimethyl-1H-pyrazol-4-yl)methanamine (5)

To a solution of compound 4 (120 mg, 0.61 mmol) in THF (5 mL) was added LAH (43 mg, 3.78 mmol). The resulting mixture was stirred at room temperature overnight. Water was added and the resulting mixture was filtered. Organic layer was separated and then concentrated in vacuum to give a white solid (crude product). LCMS (ESI) m/z=126 (M+H)⁺.

Step E: 4-(((1,3-dimethyl-1H-pyrazol-4-yl)methylamino)-6-(((1S,2S)-2-(5-methoxypyridin-2-yl)cyclopropyl)methoxy)-2-methylpyridazin-3(2H)-one (7)

Under N₂, the mixture of compound 5 (50 mg, 0.4 mmol), compound 6 (146 mg, 0.4 mmol), Pd₂(dba)₃ (37 mg, 0.04 mmol), BINAP (37 mg, 0.12 mmol) and NaOᵗ—Bu (46 mg, 0.48 mmol) in toluene (5 mL) was heated at 85° C. for 8 h. The solvent was removed; the residue was purified with prep-HPLC to give title compound as white oil. LCMS (ESI) m/z=411 (M+H)⁺, ¹H NMR (400 MHz, MeOD) δ 8.06 (d, 1H), 7.48 (s, 1H), 7.30 (dd, 1H), 7.18 (d, 1H), 5.82 (s, 1H), 4.21-4.15 (m, 3H), 4.05 (dd, 1H), 3.85 (s, 3H), 3.78 (s, 3H), 3.62 (s, 3H), 2.20 (s, 3H), 2.10-2.04 (m, 1H), 1.79-1.71 (m, 1H), 1.22-1.15 (m, 1H), 1.07-0.99 (m, 1H).

The following Examples 38-49 were prepared using the procedure of Example 37, substituting the appropriate starting materials.

TABLE 4

| Example | Structure | IUPAC Name | LCMS m/z [M + H]+ |
|---|---|---|---|
| 37 | 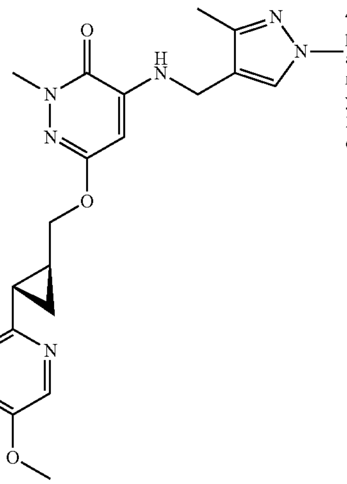 | 4-((1,3-dimethyl-1H-pyrazol-4-yl)methyl-amino)-6-(((1S,2S)-2-(5-methoxypyridin-2-yl)cyclopropyl)methoxy)-2-methylpyridazin-3(2H)-one | 411.1 |
| 38 | 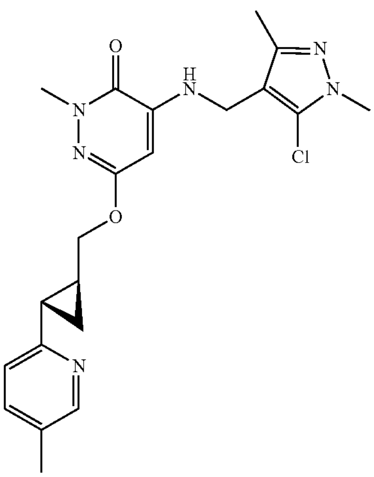 [SMILES: Cc1ccc([C@H]2C[C@@H]2COc2cc(NCc3c(C)nn(C)c3Cl)c(=O)n(C)n2)nc1] | 4-((5-chloro-1,3-dimethyl-1H-pyrazol-4-yl)methyl-amino)-2-methyl-6-(((1S,2S)-2-(5-methyl-pyridin-2-yl)cyclopropyl)methoxy)-pyridazin-3(2H)-one | 429.1 |
| 39 | 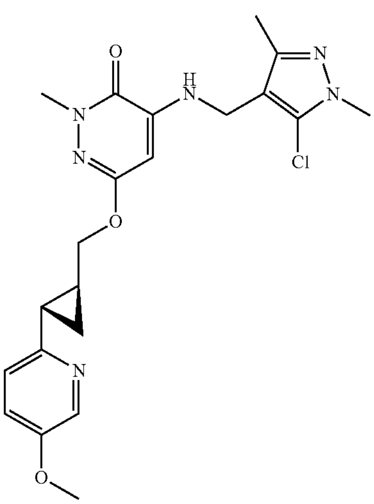 [SMILES: COc1ccc([C@H]2C[C@@H]2COc2cc(NCc3c(C)nn(C)c3Cl)c(=O)n(C)n2)nc1] | 4-((5-chloro-1,3-dimethyl-1H-pyrazol-4-yl)methylamino)-6-(((1S,2S)-2-(5-methoxypyridin-2-yl)cyclopropyl)methoxy)-2-methylpyridazin-3(2H)-one | 445.1 |

TABLE 4-continued

| Example | Structure | IUPAC Name | LCMS m/z [M + H]+ |
|---|---|---|---|
| 40 | 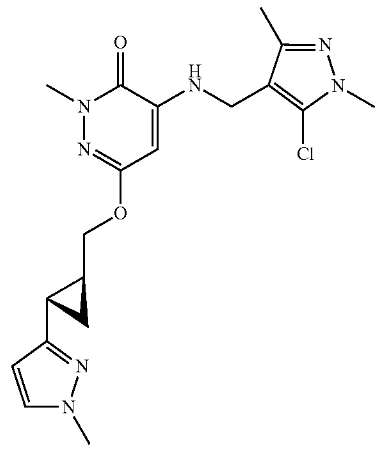 [SMILES: Cc1nn(C)c(Cl)c1CNc1cc(OC[C@H]2C[C@@H]2c2ccn(C)n2)nn(C)c1=O] | 4-(((5-chloro-1,3-dimethyl-1H-pyrazol-4-yl)methyl)amino)-2-methyl-6-(((1S,2S)-2-(1-methyl-1H-pyrazol-3-yl)cyclopropyl)methoxy)-pyridazin-3(2H)-one | 418.1 |
| 41 | 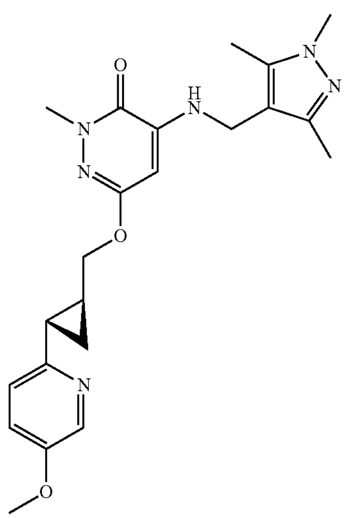 [SMILES: COc1ccc([C@H]2C[C@@H]2COc2cc(NCc3c(C)nn(C)c3C)c(=O)n(C)n2)nc1] | 6-(((1S,2S)-2-(5-methoxypyridin-2-yl)cyclopropyl)methoxy)-2-methyl-4-(((1,3,5-trimethyl-1H-pyrazol-4-yl)methyl)amino)pyridazin-3(2H)-one | 425.2 |
| 42 | 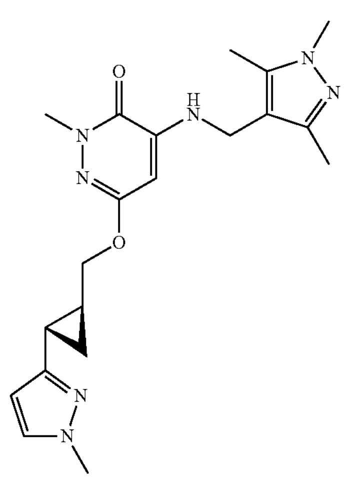 [SMILES: Cc1nn(C)c(C)c1CNc1cc(OC[C@H]2C[C@@H]2c2ccn(C)n2)nn(C)c1=O] | 2-methyl-6-(((1S,2S)-2-(1-methyl-1H-pyrazol-3-yl)cyclopropyl)methoxy)-4-(((1,3,5-trimethyl-1H-pyrazol-4-yl)methyl)amino)pyridazin-3(2H)-one | 398.2 |

TABLE 4-continued

| Example | Structure | IUPAC Name | LCMS m/z [M + H]+ |
|---|---|---|---|
| 43 | 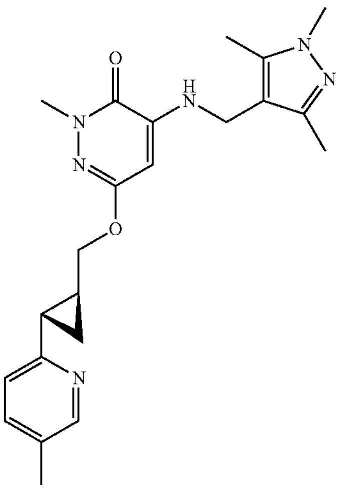 [SMILES: Cc1ccc([C@H]2C[C@@H]2COc2cc(NCc3c(C)nn(C)c3C)c(=O)n(C)n2)nc1] | 2-methyl-6-((((1S,2S)-2-(5-methylpyridin-2-yl)-cyclopropyl)methoxy)-4-(((1,3,5-trimethyl-1H-pyrazol-4-yl)methyl)-amino)pyridazin-3(2H)one | 409.2 |
| 44 | 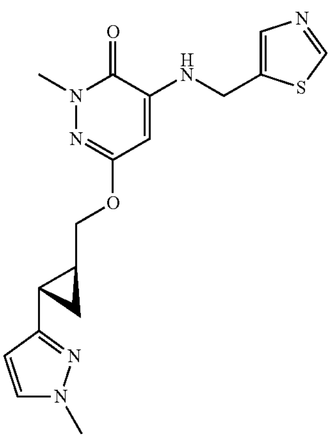 [SMILES: Cn1ccc([C@H]2C[C@@H]2COc2cc(NCc3cncs3)c(=O)n(C)n2)n1] | 2-methyl-6-((((1S,2S)-2-(1-methyl-1H-pyrazol-3-yl)cyclopropyl)methoxy)-4-((thiazol-5-ylmethyl)-amino)pyridazin-3(2H)one | 373.2 |
| 45 | 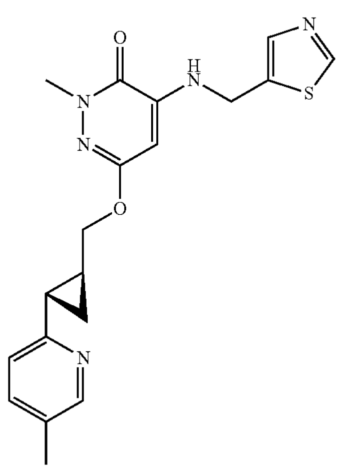 [SMILES: Cc1ccc([C@H]2C[C@@H]2COc2cc(NCc3cncs3)c(=O)n(C)n2)nc1] | 2-methyl-6-((((1S,2S)-2-(5-methylpyridin-2-yl)cyclopropyl)methoxy)-4-((thiazol-5-ylmethyl)amino)pyridazin-3(2H)-one | 384.1 |

TABLE 4-continued

| Example | Structure | IUPAC Name | LCMS m/z [M + H]+ |
|---|---|---|---|
| 46 | 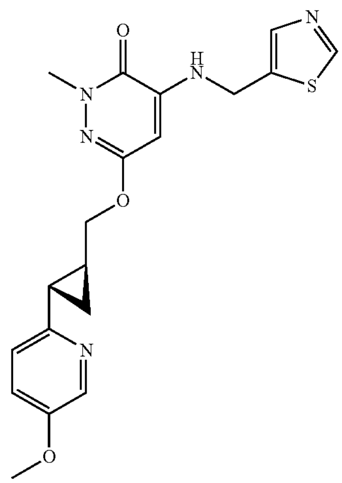 [SMILES: COc1ccc([C@H]2C[C@@H]2COc2cc(NCc3cncs3)c(=O)n(C)n2)nc1] | 6-(((1S,2S)-2-(5-methoxypyridin-2-yl)cyclopropyl)methoxy)-2-methyl-4-((thiazol-5-ylmethyl)amino)pyridazin-3(2H)-one | 400.1 |
| 47 | 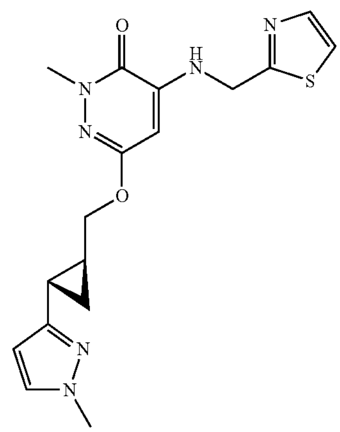 [SMILES: Cn1ccc([C@H]2C[C@@H]2COc2cc(NCc3nccs3)c(=O)n(C)n2)n1] | 2-methyl-6-(((1S,2S)-2-(1-methyl-1H-pyrazol-3-yl)cyclopropyl)methoxy)-4-((thiazol-2-ylmethyl)amino)pyridazin-3(2H)-one | 373.1 |
| 48 | 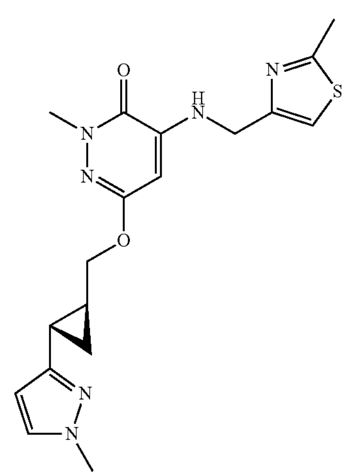 [SMILES: Cc1nc(CNc2cc(OC[C@H]3C[C@@H]3c3ccn(C)n3)nn(C)c2=O)cs1] | 2-methyl-6-(1S,2S)-2-(1-methyl-1H-pyrazol-3-yl)cyclopropyl)methoxy)-4-(((2-methylthiazol-4-yl)methyl)amino)pyridazin-3(2H)-one | NEED DATA |

TABLE 4-continued

| Example | Structure | IUPAC Name | LCMS m/z [M + H]+ |
|---|---|---|---|
| 49 | 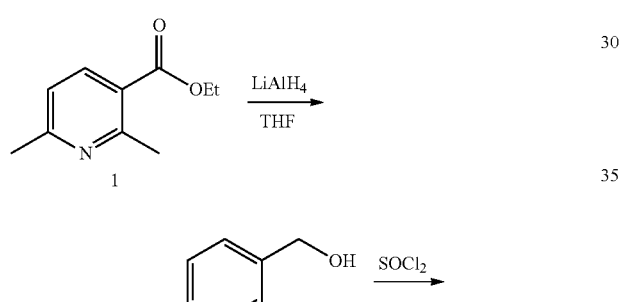 | 6-(((1S,2S)-2-(5-methoxypyridin-2-yl)cyclopropyl)methoxy)-2-methyl-4-(((2-methyl-thiazol-4-yl)methyl)amino-)-pyridazin-3(2H)-one | 387.1 |

Scheme 4

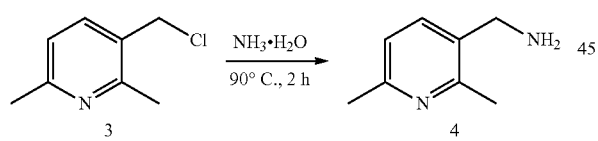

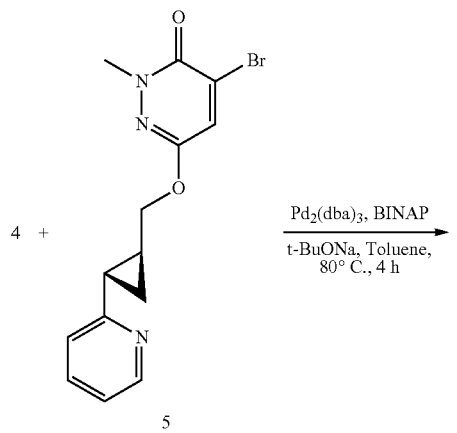

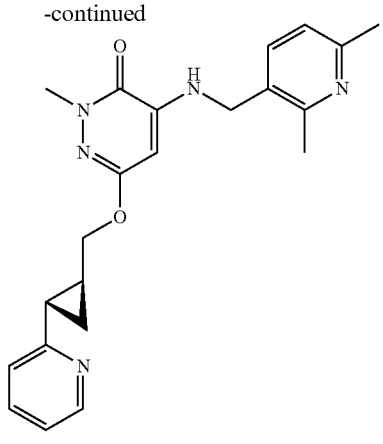

Example 50

Compound 6

Referring to Scheme 4

Step A: (2,6-dimethylpyridin-3-yl)methanol (2)

To a solution of ethyl 2,6-dimethylnicotinate (1.0 g, 5.6 mmol) in THF (20 mL) at 0° C. was added LiAlH$_4$ (318 mg, 8.4 mmol). The resulting mixture was stirred at 0° C. for 5 min and then warmed to room temperature for 1 hour. Quenched with 0.3 mL water, 0.3 mL 15% NaOH solution and then with 1 mL water sequentially. After stirred at room temperature for 15 min, sodium sulfate was added to the mixture and stirred for another 15 min and then filtered. The resulting solution was concentrated to afford the crude product which was used for next step directly without further purification. LCMS (ESI) m/z=138.1 138.1 (M+H)+.

Step B: 3-(chloromethyl)-2,6-dimethylpyridine (3)

The solution of compound (2,6-dimethylpyridin-3-yl)methanol (0.76 g, 5.6 mmol) in SOCl$_2$ (5 mL) was stirred at room temperature for 1 hour and then concentrated to give the crude product 3 which was used for next step directly without further purification. LCMS (ESI) m/z=156.1 (M+H)$^+$.

Step C: (2,6-dimethylpyridin-3-yl)methanamine (4)

The solution of 3-(chloromethyl)-2,6-dimethylpyridine (850 mg, 5.5 mmol) in ammonia solution (10 mL) was stirred at 90° C. for 2 hours and then concentrated to give the crude product which was used for next step directly without further purification. LCMS (ESI) m/z=137.1 (M+H)$^+$.

Step D: 4-((2,6-dimethylpyridin-3-yl)methylamino)-2-methyl-6-(((1S,2S)-2-(pyridin-2-yl)cyclopropyl)methoxy)pyridazin-3(2H)-one (6)

A mixture of (2,6-dimethylpyridin-3-yl)methanamine (30 mg, 0.2 mmol), 4-bromo-2-methyl-6-(((1S,2S)-2-(pyridin-2-yl)cyclopropyl)methoxy)pyridazin-3(2H)-one (68 mg, 0.2 mmol), Pd$_2$(dba)$_3$ (18 mg, 0.02 mmol), BINAP (18 mg, 0.03 mmol) and $^t$-BuONa (38 mg, 0.4 mmol) in toluene (4 mL) under N$_2$ was heated at 80° C. for 4 h. The mixture was filtered and concentrated to give crude product which was purified by Prep-HPLC to give the title compound as oil. $^1$H NMR (400 MHz, CD$_3$OD) δ 8.34 (d, 1H), 7.67-7.62 (m, 1H), 7.47 (d, 1H), 7.21 (d, 1H), 7.16-7.13 (m, 1H), 7.05 (d, 1H), 5.67 (s, 1H), 4.35 (s, 2H), 4.20-4.16 (m, 1H), 4.03-3.98 (m, 1H), 3.63 (s, 3H), 2.50 (s, 3H), 2.46 (s, 3H), 2.11-2.07 (m, 1H), 1.84-1.79 (m, 1H), 1.26-1.21 (m, 1H), 1.09-1.04 (m, 1H), LCMS m/z (M+H) 392.2 found, 392.2 required.

The following Examples 50-66 were prepared using the procedure of Example 50, substituting the appropriate starting materials.

TABLE 5

| Example | Structure | IUPAC Name | LCMS m/z [M + H]$^+$ |
|---------|-----------|------------|----------------------|
| 50 | 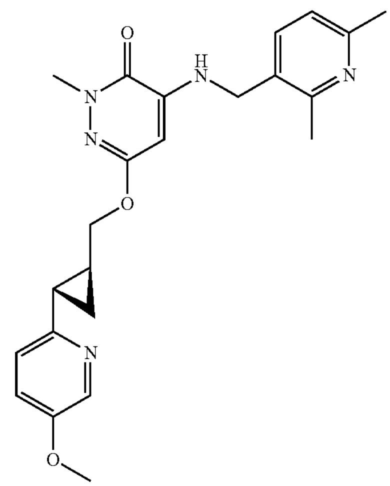 [SMILES: COc1ccc([C@H]2C[C@@H]2COc2cc(NCc3ccc(C)nc3C)c(=O)n(C)n2)nc1] | 4-(((2,6-dimethylpyridin-3-yl)methyl)amino)-6-(((1S,2S)-2-(5-methoxypyridin-2-yl)cyclopropyl)methoxy)-2-methylpyridazin-3(2H)-one | 422.1 |
| 51 | 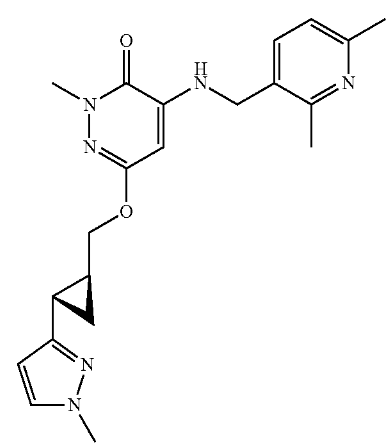 [SMILES: Cc1ccc(CNc2cc(OC[C@H]3C[C@@H]3c3ccn(C)n3)nn(C)c2=O)c(C)n1] | 4-(((2,6-dimethylpyridin-3-yl)methyl)amino)-2-methyl-6-(((1S,2S)-2-(1-methyl-1H-pyrazol-3-yl)cyclopropyl)methoxy)-pyridazin-3(2H)-one | 395.2 |

TABLE 5-continued

| Example | Structure | IUPAC Name | LCMS m/z [M + H]+ |
|---|---|---|---|
| 52 | 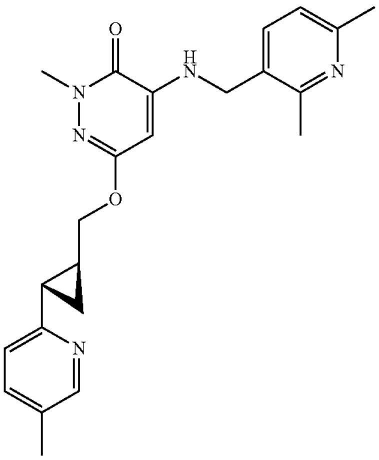 [SMILES: Cc1ccc([C@H]2C[C@@H]2COc2cc(NCc3ccc(C)nc3C)c(=O)n(C)n2)nc1] | 4-(((2,6-dimethylpyridin-3-yl)methyl)amino)-2-methyl-6-((((1S,2S)-2-(5-methylpyridin-2-yl)cyclopropyl)methoxy)-pyridazin-3(2H)-one | 406.1 |
| 53 | 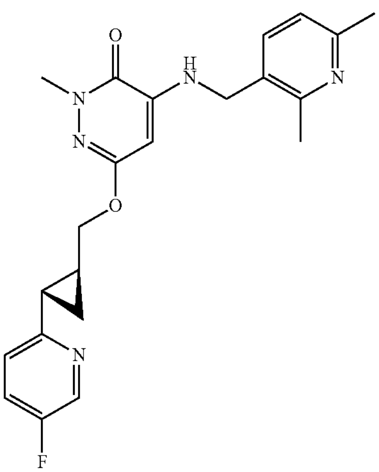 [SMILES: Cc1ccc(CNc2cc(OC[C@H]3C[C@@H]3c3ccc(F)cn3)nn(C)c2=O)c(C)n1] | 4-(((2,6-dimethylpyridin-3-yl)methyl)amino)-6-((((1S,2S)-2-(5-fluoro-pyridin-2-yl)cyclopropyl-)-methoxy)-2-methyl-pyridazin-3(2H)-one | 410.1 |
| 54 | 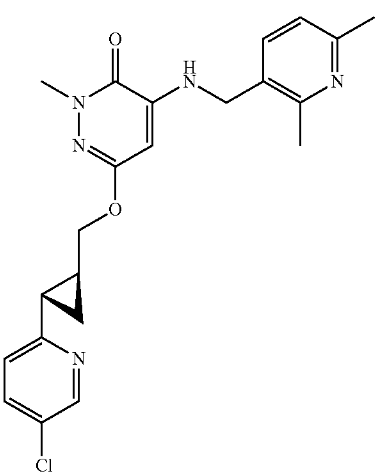 [SMILES: Cc1ccc(CNc2cc(OC[C@H]3C[C@@H]3c3ccc(Cl)cn3)nn(C)c2=O)c(C)n1] | 6-((((1S,2S)-2-(5-chloro-pyridin-2-yl)cyclopropyl-)-methoxy-4-(((2,6-dimethylpyridin-3-yl)methyl)amino)-2-methylpyridazin-3(2H)one | 426.1 |

TABLE 5-continued

| Example | Structure | IUPAC Name | LCMS m/z [M + H]+ |
|---|---|---|---|
| 55 | 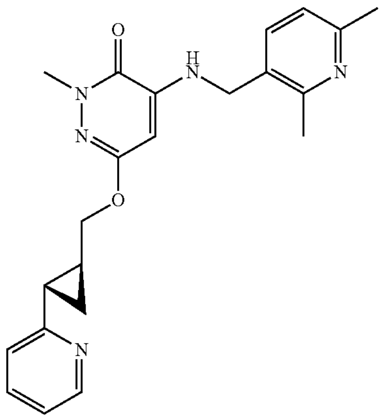 [SMILES: Cc1ccc(CNc2cc(OC[C@H]3C[C@@H]3c3ccccn3)nn(C)c2=O)c(C)n1] | 4-(((2,6-dimethylpyridin-3-yl)methyl)amino)-2-methyl-6-(((1S,2S)-2-(pyridin-2-yl)cyclopropyl-)-methoxy)pyridazin-3(2H)-one | 392.2 |
| 56 | 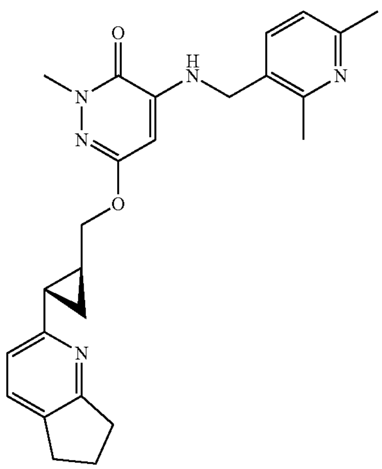 [SMILES: Cc1ccc(CNc2cc(OC[C@H]3C[C@@H]3c3ccc4c(n3)CCC4)nn(C)c2=O)c(C)n1] | 6-(((1S,2S)-2-(6,7-dihydro-5H-cyclopenta-[b]pyridin-2-yl)cyclo-propyl)methoxy)-4-(((2,6-dimethylpyridin-3-yl)-methyl)amino)-2-methyl-pyridazin-3(2H)-one | 432.2 |
| 57 | 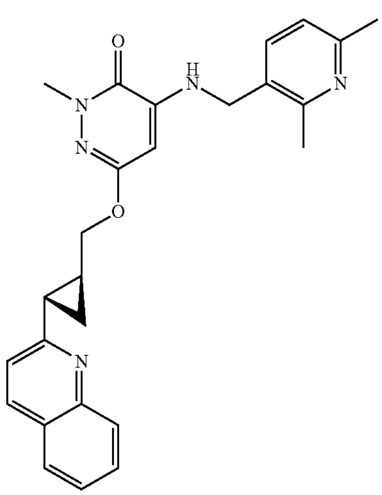 [SMILES: Cc1ccc(CNc2cc(OC[C@H]3C[C@@H]3c3ccc4ccccc4n3)nn(C)c2=O)c(C)n1] | 4-(((2,6-dimethylpyridin-3-yl)methyl)amino)-2-methyl-6-(((1S,2S)-2-(quinolin-2-yl)cyclopropyl)methoxy)-pyridazin-3(2H)-one | 442.1 |

TABLE 5-continued

| Example | Structure | IUPAC Name | LCMS m/z [M + H]+ |
|---|---|---|---|
| 58 | 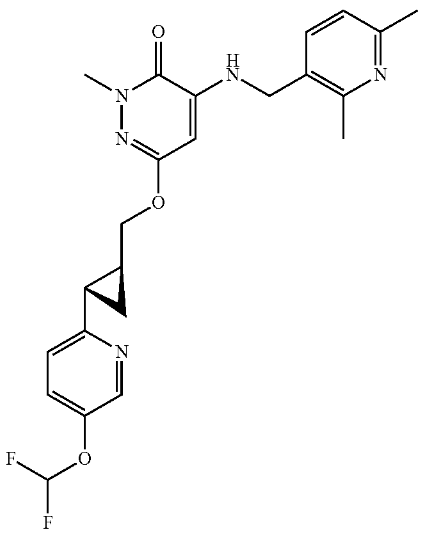 [SMILES: Cc1ccc(CNc2cc(OC[C@H]3C[C@@H]3c3ccc(OC(F)F)cn3)nn(C)c2=O)c(C)n1] | 6-(((1S,2S)-2-(5-(difluoromethoxy)pyridin-2-yl)cyclopropyl)methoxy)-4-(((2,6-dimethylpyridin-3-yl)methyl)amino)-2-methylpyridazin-3(2H)-one | 458.1 |
| 59 | 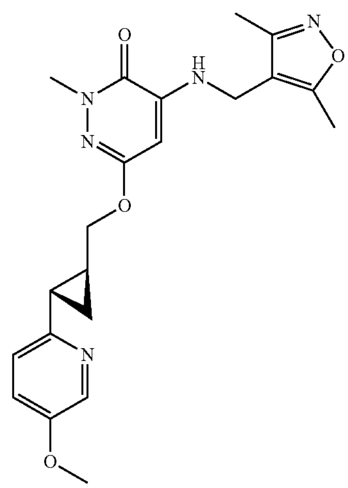 [SMILES: COc1ccc([C@H]2C[C@@H]2COc2cc(NCc3c(C)noc3C)c(=O)n(C)n2)nc1] | 4-(((3,5-dimethylisoxazol-4-yl)methyl)amino)-6-(((1S,2S)-2-(5-methoxypyridin-2-yl)cyclopropyl-)methoxy)-2-methylpyridazin-3(2H)-one | 412.1 |
| 60 | 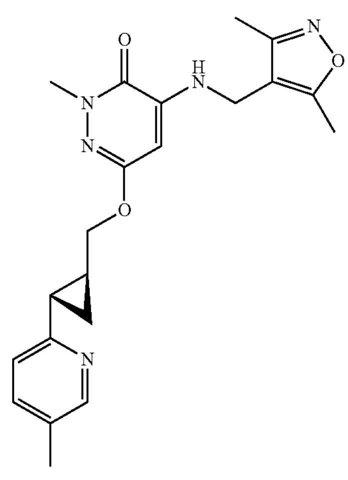 [SMILES: Cc1ccc([C@H]2C[C@@H]2COc2cc(NCc3c(C)noc3C)c(=O)n(C)n2)nc1] | 4-(((3,5-dimethylisoxazol-4-yl)methyl)amino)-2-methyl-6-(((1S,2S)-2-(5-methylpyridin-2-yl)cyclopropyl)methoxy)pyridazin-3(2H)-one | 396.2 |

TABLE 5-continued

| Example | Structure | IUPAC Name | LCMS m/z [M + H]+ |
|---|---|---|---|
| 61 | 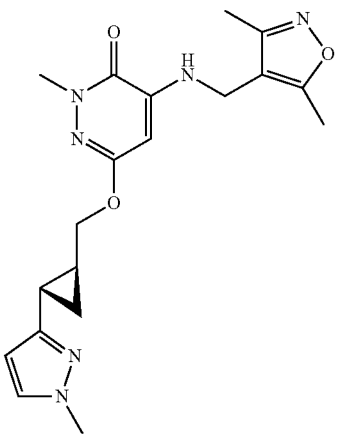 [SMILES: Cc1noc(C)c1CNc1cc(OC[C@H]2C[C@@H]2c2ccn(C)n2)nn(C)c1=O] | 4-(((3,5-dimethylisoxazol-4-yl)methyl)amino)-2-methyl-6-(((1S,2S)-2-(1-methyl-1H-pyrazol-3-yl)cyclopropyl)methoxy)-pyridazin-3(2H)-one | 385.1 |
| 62 | 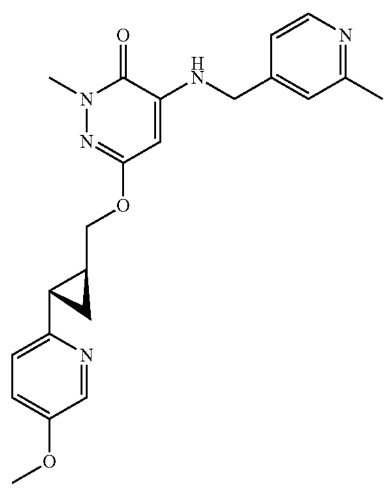 [SMILES: COc1ccc([C@H]2C[C@@H]2COc2cc(NCc3ccnc(C)c3)c(=O)n(C)n2)nc1] | 6-(((1S,2S)-2-(5-methoxy-pyridin-2-yl)cyclopropyl-)-methoxy)-2-methyl-4-(((2-methylpyridin-4-yl)methyl)amino)pyridazin-3(2H)-one | 408.2 |
| 63 | 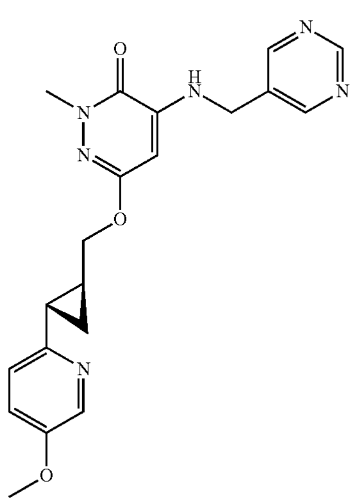 [SMILES: COc1ccc([C@H]2C[C@@H]2COc2cc(NCc3cncnc3)c(=O)n(C)n2)nc1] | 6-(((1S,2S)-2-(5-methoxy-pyridin-2-yl)cyclopropyl-)-methoxy)-2-methyl-4-((pyrimidin-5-ylmethyl)-amino)pyridazin-3(2H)one | 395.1 |

TABLE 5-continued

| Example | Structure | IUPAC Name | LCMS m/z [M + H]+ |
|---|---|---|---|
| 64 | 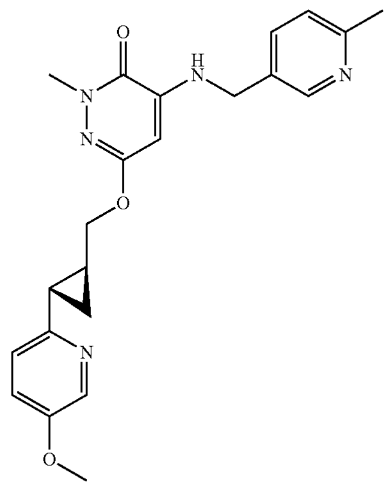 [SMILES: COc1ccc([C@H]2C[C@@H]2COc2cc(NCc3ccc(C)nc3)c(=O)n(C)n2)nc1] | 6-(((1S,2S)-2-(5-methoxy-pyridin-2-yl)cyclopropyl-)-methoxy)-2-methyl-4-(((6-methylpyridin-3-yl)methyl)amino)pyridazin-3(2H)-one | 408.2 |
| 65 | 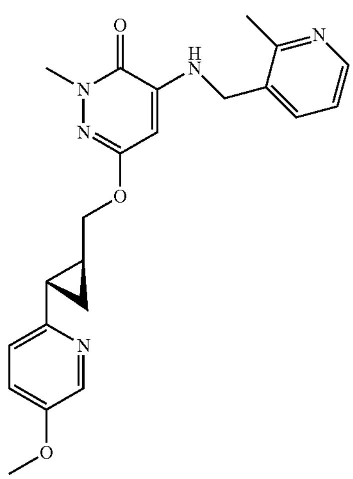 [SMILES: COc1ccc([C@H]2C[C@@H]2COc2cc(NCc3cccnc3C)c(=O)n(C)n2)nc1] | 6-(((1S,2S)-2-(5-methoxy-pyridin-2-yl)cyclopropyl-)-methoxy)-2-methyl-4-(((2-methylpyridin-3-yl)-methyl)amino)pyridazin-3(2H)-one | 408.2 |
| 66 | 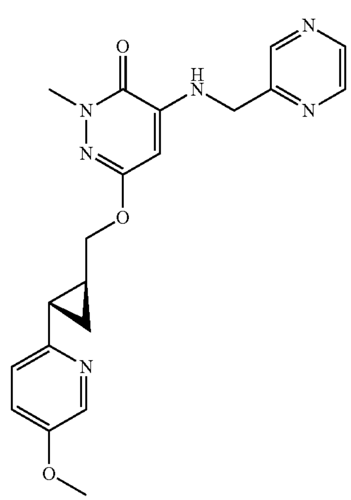 [SMILES: COc1ccc([C@H]2C[C@@H]2COc2cc(NCc3cnccn3)c(=O)n(C)n2)nc1] | 6-(((1S,2S)-2-(5-methoxypyridin-2-yl)cyclopropyl)methoxy)-2-methyl-4-((pyrazin-2-ylmethyl)amino)pyridazin-3(2H)-one | 395.2 |

Scheme 4-1

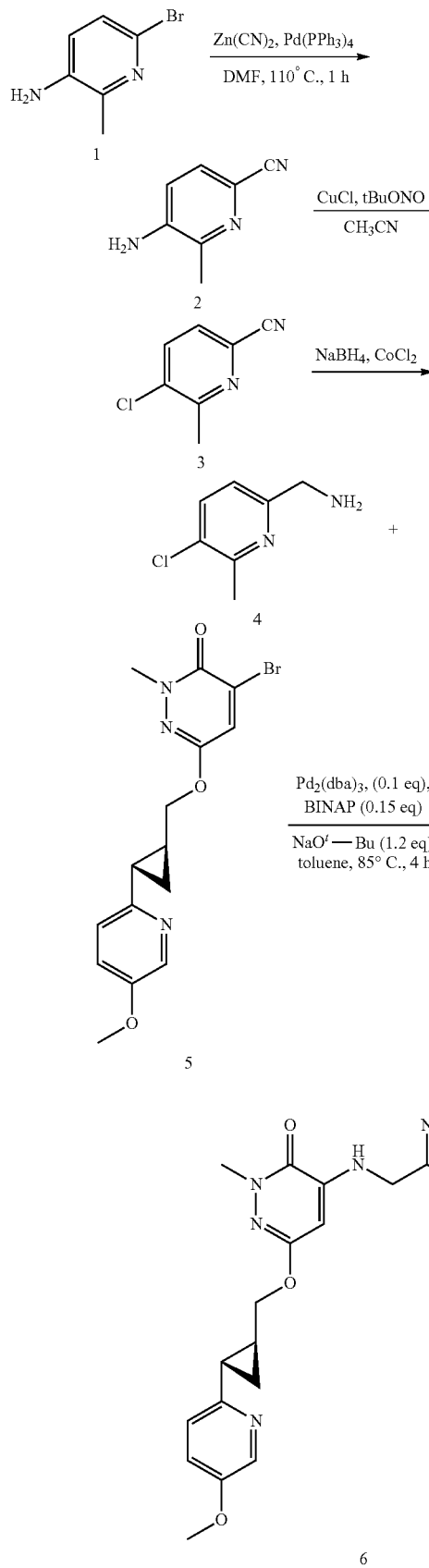

Referring to Scheme 4-1

Step A: 5-amino-6-methylpicolinonitrile (2)

To a solution of 6-bromo-2-methylpyridin-3-amine (compound 1, 500 mg, 2.69 mmol) in DMF (10 mL) was added $Zn(CN)_2$ (943 mg, 8.06 mmol) and $Pd(PPh_3)_4$ (288 mg, 0.3 mmol) at room temperature. The reaction was stirred at 110° C. in microwave reactor for 1 h. After it was cooled to room temperature, the mixture was filtered and purified by reverse phase chromatography (X bridge Prep C18OBD, 40-60% MeOH in water with 10 mmol $NH_4HCO_3$ modifier) to afford the compound as an oil.

Step B: 5-chloro-6-methylpicolinonitrile (3)

A solution of 5-amino-6-methylpicolinonitrile (2) (260 mg, 1.95 mmol), CuCl (290 mg, 2.93 mmol) and t-BuONO (456 mg, 3.9 mmol) in $CH_3CN$ (10 mL) was stirred at room temperature under $N_2$ for 2 h, and then warmed to 60° C. After 2 h, 10 mL 6N HCl was added and extracted with EA (3×10 mL). The organic phase was dried with anhydrous $Na_2SO_4$, filtered and concentrated. The residue was purified by Prep-TLC using PE/EtOAc=1/1 to give title compound as oil.

Step C: (5-chloro-6-methylpyridin-2-yl)methanamine (4)

To a mixture of 5-chloro-6-methylpicolinonitrile (3) (200 mg, 1.31 mmol) in MeOH (10 mL) was added $NaBH_4$ (150 mg, 3.94 mmol), $CoCl_2$ (5 mg) at room temperature. After 30 min, the mixture was filtered and purified by reverse phase chromatography (X bridge Prep C18OBD, 40-60% MeOH in water with 10 mmol $NH_4HCO_3$ modifier) to afford the compound as an oil.

Step D: 4-((5-chloro-6-methylpyridin-2-yl)methylamino)-6-((((1S,2S)-2-(5-methoxypyridin-2-yl)cyclopropyl)methoxy)-2-methylpyridazin-3(2H)-one (6)

To the solution of 4-bromo-6-((((1S,2S)-2-(5-methoxypyridin-2-yl)cyclopropyl)methoxy)-2-methylpyridazin-3(2H)-one (5) (80 mg, 0.219 mmol) in toluene (5 mL) under $N_2$, (5-chloro-6-methylpyridin-2-yl)methanamine (4) (50 mg, 0.320 mmol), $Pd_2(dba)_3$ (15 mg, 0.0219 mmol), BINAP (20 mg, 0.0328 mmol) and NaOt-Bu (42 mg, 0.438 mmol) were added. After the reaction mixture was stirred at 85° C. for 4 h, 15 mL water was added. The mixture was extracted with EtOAc (3×10 mL). The combined organics were dried over $Na_2SO_4$, filtered and concentrated in vacuo. The residue was purified by reverse phase chromatography (X bridge Prep C18OBD, 40-60% acetonitrile in water with 10 mmol $NH_4HCO_3$ modifier) to afford the compound as an oil (15 mg, 15.5% yield). $^1H$ NMR (400 MHz, MeOD) δ 8.05-8.04 (s, 1H), 7.75-7.73 (d, 1H), 7.30-7.27 (m, 1H), 7.20-7.15 (m, 2H), 5.72 (s 1H), 4.40 (s, 2H), 4.18-4.14 (m, 1H), 4.10-4.00 (m, 1H), 3.86 (s, 3H), 3.71 (s, 3H), 2.61 (s, 3H), 2.08-2.03 (m, 1H), 1.75-1.70 (m, 1H), 1.18-1.13 (m, 1H) 1.03-0.95 (m, 1H); LRMS m/z (M+H) 441.1 found, 441.15 required.

Scheme 4-2

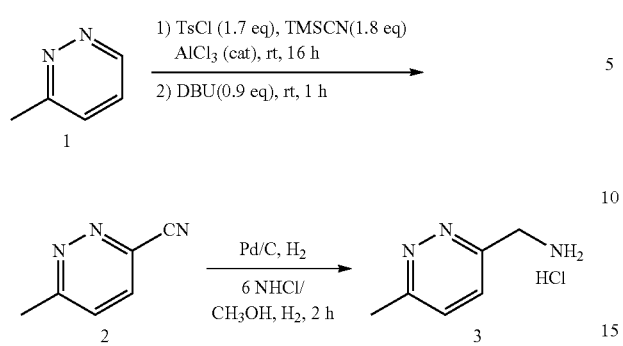

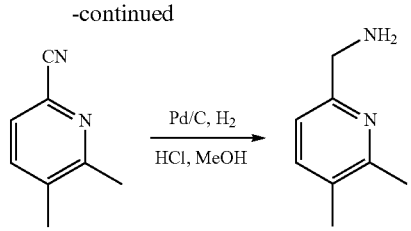

Referring to Scheme 4-2

Step A: 6-methylpyridazine-3-carbonitrile (2)

To a stirring solution of 3-methylpyridazine (1.1 g, 11.80 mmol) in dichloromethane (20 mL) was added $AlCl_3$ (0.05 g) followed by trimethylsilylcyanide (2.1 g, 21.1 mmol). After 20 min, a solution of p-toluenesulfonyl chloride (3.8 g, 20.1 mmol) in dichloromethane (5 mL) was added slowly and the solution was stirred for 16 h. The solvent was removed in vacuo and ethanol (10 ml) was added and stirred for 15 min, then filtered to give a white solid. The solid was dissolved in THF (200 mL) and DBU (1.6 mL, 10.5 mmol) was added. After 1 h, the solvent was removed in vacuo and the residue was partitioned between hexane and saturated aqueous $NH_4Cl$. The aqueous phase was basified with solid $Na_2CO_3$, and then extracted with EtOAc (100 ml*2). The combined ethyl acetate phases was dried over $MgSO_4$, filtered and concentrated to give compound 2 as a white solid.

Step B: (6-methylpyridazin-3-yl)methanamine hydrochloride (3)

To a solution of compound 2 (250 mg, 2.38 mmol) in MeOH (20 mL) was added 6N HCl (5 mL) followed by Pd/C (100 mg). The reaction mixture was kept on Parr shaker for 2 h at 40 psi. The reaction mixture was filtered through celite and washed with 5 mL of MeOH and the filtrate was concentrated to give compound 3 as a dark brown solid.

Scheme 4-3

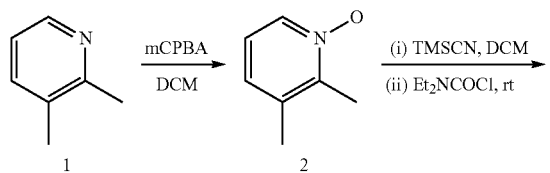

Step A: 2,3-dimethylpyridine 1-oxide (2)

A solution of 2 in Scheme 4-3, 3-dimethylpyridine (107 mg, 1 mmol) in DCM (10 mL) was treated with m-CPBA (345 mg, 2 mmol) and stirred at room temperature overnight. The reaction mixture was concentrated and the resulting material was purified directly by combi-flash (MeOH/$H_2O$ ($NH_4HCO_3$)) to give a white solid. LCMS (ESI) m/z=124 $(M+H)^+$.

Step B: 5,6-dimethylpicolinonitrile (3)

To a solution of compound 2 in Scheme 4-3 (98 mg, 0.8 mmol) in DCM (10 mL) was added TMSCN (0.2 mL) at room temperature. After the mixture was stirred for 30 min, diethylcarbamic chloride (0.2 mL) was added, and stirred for 24 h. The mixture was concentrated and the residue was purified by combi-flash (MeOH/$H_2O$ ($NH_4HCO_3$)) to give a white solid. LCMS (ESI) m/z=134 $(M+H)^+$.

Step C: (5,6-dimethylpyridin-2-yl)methanamine (4)

To a solution of compound 3 in Scheme 4-3 (58 mg, 0.44 mmol) in MeOH (5 mL) and 6N HCl (1 mL) was added Pd/C (10 mg) at room temperature, the mixture was filled with hydrogen for three times and stirred overnight. The reaction mixture was filtered through celite and washed with MeOH and the filtrate was concentrated. The residue was concentrated to give compound 4 as a dark brown solid.

Examples 67-77

The following Examples 67-77 were prepared using the procedure of Example 67, substituting the appropriate starting materials.

TABLE 6
| Example | Structure | IUPAC Name | LCMS m/z [M + H]+ |
|---|---|---|---|
| 67 | 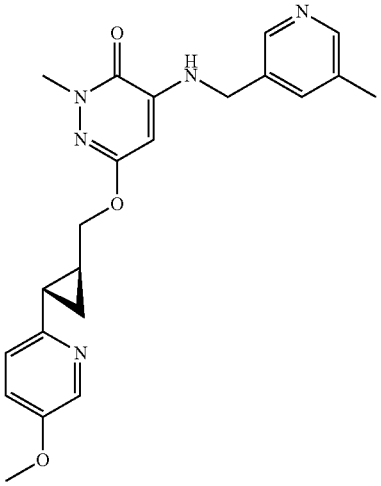 [SMILES: COc1ccc([C@H]2C[C@@H]2COc2cc(NCc3cncc(C)c3)c(=O)n(C)n2)nc1] | 6-(((1S,2S)-2-(5-methoxypyridin-2-yl)cyclopropyl)methoxy)-2-methyl-4-(((5-methylpyridin-3-yl)methyl)amino)pyridazin-3(2H)-one | 408.2 |
| 68 | 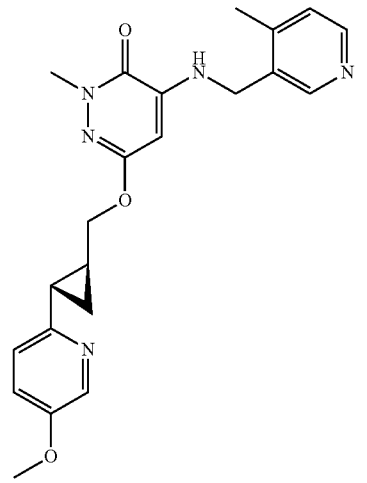 [SMILES: COc1ccc([C@H]2C[C@@H]2COc2cc(NCc3cnccc3C)c(=O)n(C)n2)nc1] | 6-(((1S,2S)-2-(5-methoxy-pyridin-2-yl)cyclopropyl-)-methoxy)-2-methyl-4-((pyridin-3-ylmethyl)-amino)pyridazin-3(2H)one | 394.2 |
| 69 | 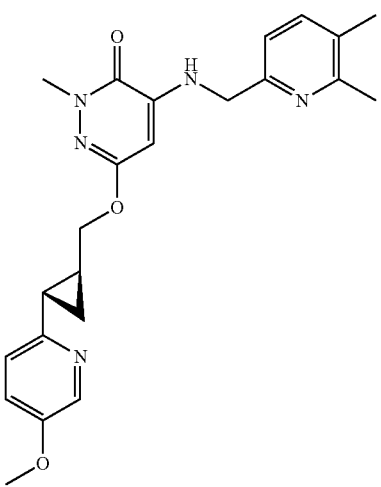 [SMILES: COc1ccc([C@H]2C[C@@H]2COc2cc(NCc3ccc(C)c(C)n3)c(=O)n(C)n2)nc1] | 4-(((5,6-dimethylpyridin-2-yl)methyl)amino)-6-(((1S,2S)-2-(5-methoxy-pyridin-2-yl)cyclopropyl-)-methoxy)-2-methyl-pyridazin-3(2H)-one | 422.2 |

TABLE 6-continued

| Example | Structure | IUPAC Name | LCMS m/z [M + H]+ |
|---------|-----------|------------|-------------------|
| 70 | 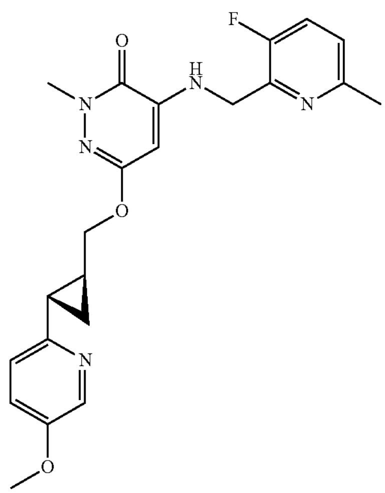 [SMILES: COc1ccc([C@H]2C[C@@H]2COc2cc(NCc3nc(C)ccc3F)c(=O)n(C)n2)nc1] | 4-(((3-fluoro-6-methyl-pyridin-2-yl)methyl)-amino)-6-(((1S,2S)-2-(5-methoxypyridin-2-yl)-cyclopropyl)methoxy)-2-methylpyridazin-3(2H)one | 426.2 |
| 71 | 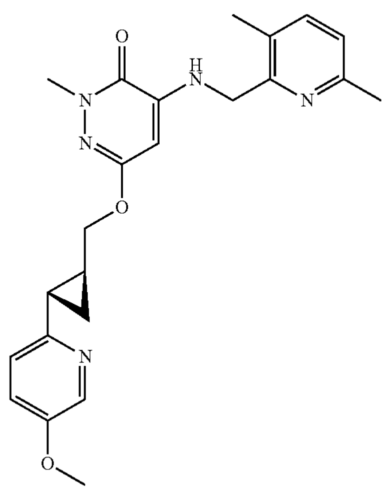 [SMILES: COc1ccc([C@H]2C[C@@H]2COc2cc(NCc3nc(C)ccc3C)c(=O)n(C)n2)nc1] | 4-(((3,6-dimethylpyridin-2-yl)methyl)amino)-6-(((1S,2S)-2-(5-methoxy-pyridin-2-yl)cyclopropyl-)-methoxy)-2-methylpyridazin-3(2H)one | 422.2 |
| 72 | 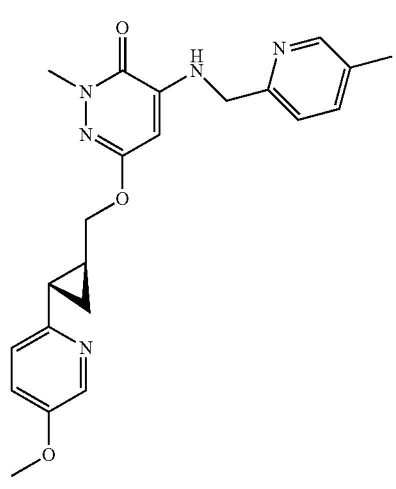 [SMILES: COc1ccc([C@H]2C[C@@H]2COc2cc(NCc3ccc(C)cn3)c(=O)n(C)n2)nc1] | 6-(((1S,2S)-2-(5-methoxy-pyridin-2-yl)cyclopropyl-)-methoxy)-2-methyl-4-(((5-methylpyridin-2-yl)-methyl)amino)pyridazin-3(2H)-one | 408.2 |

TABLE 6-continued

| Example | Structure | IUPAC Name | LCMS m/z [M + H]+ |
|---|---|---|---|
| 73 | 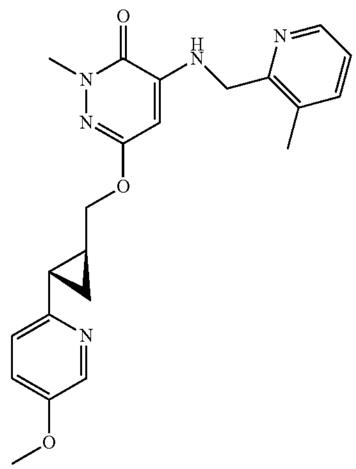 [SMILES: COc1ccc([C@H]2C[C@@H]2COc2cc(NCc3ncccc3C)c(=O)n(C)n2)nc1] | 6-(((1S,2S)-2-(5-methoxypyridin-2-yl)cyclopropyl)methoxy)-2-methyl-4-(((3-methyl-pyridin-2-yl)methyl)-amino)pyridazin-3(2H)one | 408.2 |
| 74 | 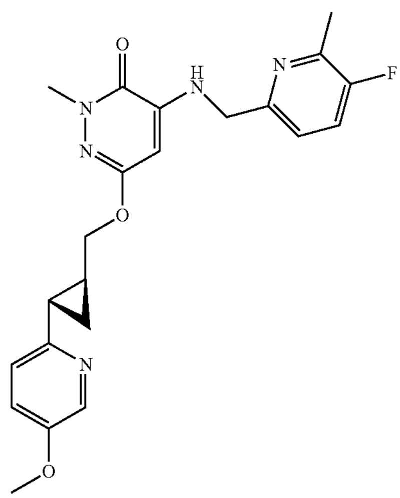 [SMILES: COc1ccc([C@H]2C[C@@H]2COc2cc(NCc3ccc(F)c(C)n3)c(=O)n(C)n2)nc1] | 4-(((5-fluoro-6-methyl-pyridin2yl)methyl)amino)-6-(((1S,2S)-2-(5-methoxy-pyridin-2-yl)cyclopropyl-)-methoxy)-2-methyl-pyridazin-3(2H)-one | 426.2 |
| 75 | 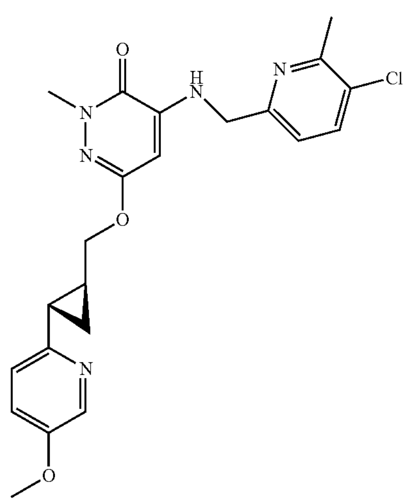 [SMILES: COc1ccc([C@H]2C[C@@H]2COc2cc(NCc3ccc(Cl)c(C)n3)c(=O)n(C)n2)nc1] | 4-(((5-chloro-6-methyl-pyridin-2-yl)methyl)-amino)-6-(((1S,2S)-2-(5-methoxypyridin-2-yl)cyclopropyl)methoxy)2-methylpyridazin-3(2H)one | 442.1 |

TABLE 6-continued
| Example | Structure | IUPAC Name | LCMS m/z [M + H]+ |
|---|---|---|---|
| 76 | 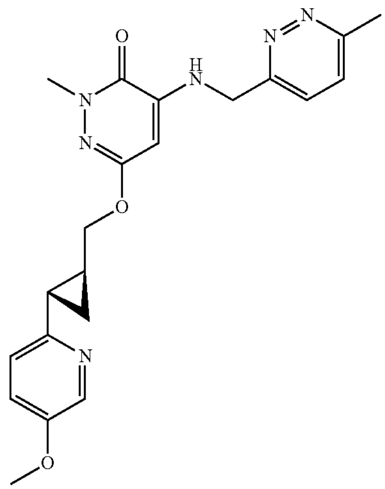 [SMILES: COc1ccc([C@H]2C[C@@H]2COc2cc(NCc3ccc(C)nn3)c(=O)n(C)n2)nc1] | 6-(((1S,2S)-2-(5-methoxy-pyridin-2-yl)cyclopropyl-)-methoxy)-2-methyl-4-(((6-methylpyridazin-3-yl)methyl)amino)pyridazin-3(2H)-one | 409.2 |
| 77 | 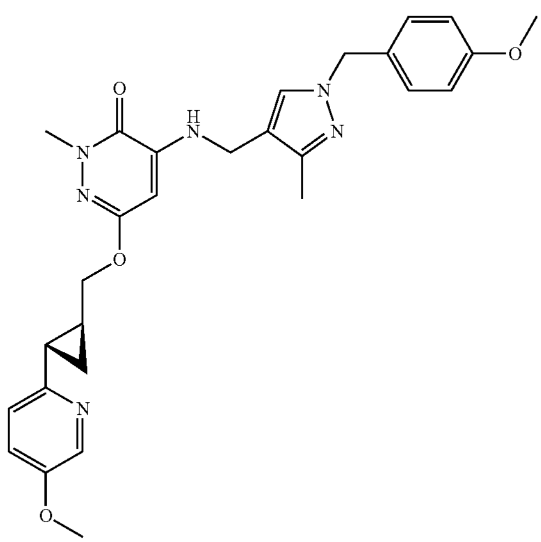 [SMILES: COc1ccc(Cn2cc(CNc3cc(OC[C@H]4C[C@@H]4c4ccc(OC)cn4)nn(C)c3=O)c(C)n2)cc1] | 4-((1-(4-methoxybenzyl)-3-methyl-1H-pyrazol-4-yl)methylamino)-6-(((1S,2S)-2-(5-methoxy-pyridin-2-yl)cyclopropyl)-methoxy)-2-methyl-pyridazin-3(2H)-one | 517.2 |
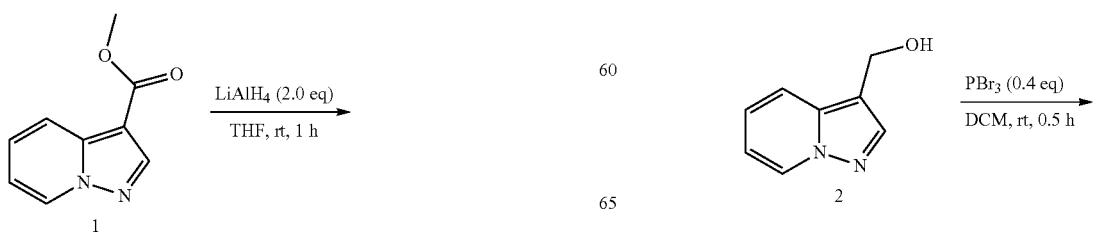
Scheme 5

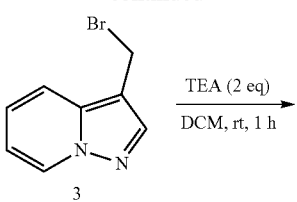

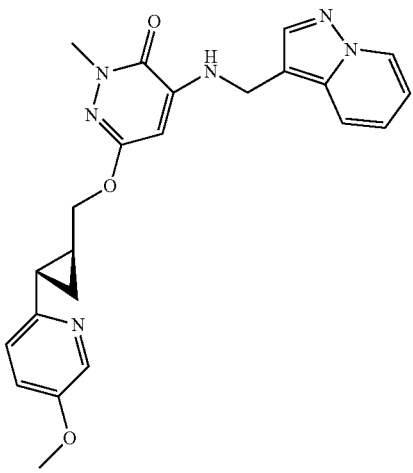

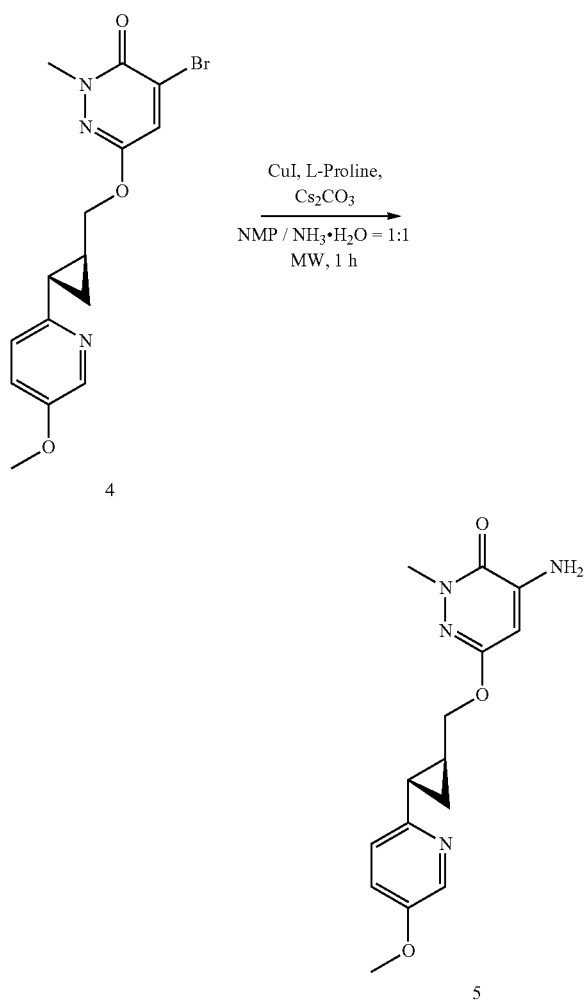 [SMILES: COc1ccc([C@H]2C[C@@H]2COc2cc(Br)c(=O)n(C)n2)nc1 ; COc1ccc([C@H]2C[C@@H]2COc2cc(N)c(=O)n(C)n2)nc1]

Examples 78-91

Referring to Scheme 5

Step A: pyrazolo[1,5-a]pyridin-3-ylmethanol (2)

A solution of methyl pyrazolo[1,5-a]pyridine-3-carboxylate carbamate (1) (400 mg, 2.10 mmol) in THF (4 mL) was added LiAlH$_4$ (159 mg, 4.20 mmol) at room temperature for 1 h. The reaction mixture was concentrated and 10 mL sat. aq. NaHCO$_3$ was added, extracted with EA (3×10 mL). The organic phase was dried with anhydrous Na$_2$SO$_4$, filtered and concentrated. The residue was purified by Prep-TLC TLC using PE/EtOAc=2/1 to give title compound as oil.

Step B: 3-(bromomethyl)pyrazolo[1,5-a]pyridine (3)

To the solution of pyrazolo[1,5-a]pyridin-3-ylmethanol (2) (50 mg, 0.338 mmol) in DCM (2 mL) was added PBr$_3$ (36.58 mg, 0.135 mmol) at room temperature for 30 min. The reaction solution was used in the next step.

Step C: 4-amino-6-(((1S,2S)-2-(5-methoxypyridin-2-yl)cyclopropyl)methoxy)-2-methylpyridazin-3(2H)-one (5)

To a MW tube was added compound 4 (1.0 g, 2.7 mmol), CuI (52 mg, 0.27 mmol), L-Proline (66 mg, 0.4 mmol), Cs$_2$CO$_3$ (1.0 g, 3.2 mmol) in the mixed solution of NMP/NH$_3$.H$_2$O (5 mL/5 mL). The resulting mixture was activated under microwave at 110° C. for 1 hour. Filtered and purified with flash chromatography directly to afford the compound 5.

Step D: 2-methyl-6-(((1S,2S)-2-(5-methylpyridin-2-yl)cyclopropyl)methoxy)-4-(pyrazolo[1,5-a]pyridin-3-ylmethylamino)pyridazin-3(2H)-one (6)

To the solution of 3-(bromomethyl)pyrazolo[1,5-a]pyridine (3) (4 mL, 0.27 mmol, 0.0675 mmol/ml) in DCM (4 mL) was added TEA (33 mg, 0.33 mmol) and 4-amino-6-(((1S,2S)-2-(5-methoxypyridin-2-yl)cyclopropyl)methoxy)-2-methylpyridazin-3(2H)-one (50 mg, 0.165 mmol) at room temperature and stirred for 1 h, then 10 mL sat. NH$_4$Cl was added, extracted with EtOAc (3×10 mL). The combined organic phase were dried over Na$_2$SO$_4$, filtered and concentrated in vacuo. The residue was purified by reverse phase chromatography (X bridge Prep C18OBD, 40-60% acetonitrile in water with 10 mmol NH$_4$HCO$_3$ modifier) to afford the compound as an oil. $^1$H NMR (400 MHz, MeOD) δ 8.47 (d, 1H), 8.03 (d, 1H), 7.96 (s, 1H), 7.67 (d, 1H), 7.26-7.11 (m, 3H), 6.87-6.84 (m, 1H), 5.85 (s, 1H), 4.50 (s, 2H), 4.17-4.13 (m, 1H), 4.02-3.97 (m, 1H), 3.82 (s, 3H), 3.59 (s, 3H), 2.06-2.02 (m, 1H), 1.75-1.71 (m, 1H), 1.17-1.13 (m, 1H) 1.02-0.99 (m, 1H); LRMS m/z (M+H) 433.1 found, 433.15 required.

The following Examples 78-91 were prepared using the procedure of Example 78, substituting the appropriate starting materials.

TABLE 7

| Example | Structure | IUPAC Name | LCMS m/z [M + H]+ |
|---|---|---|---|
| 78 | 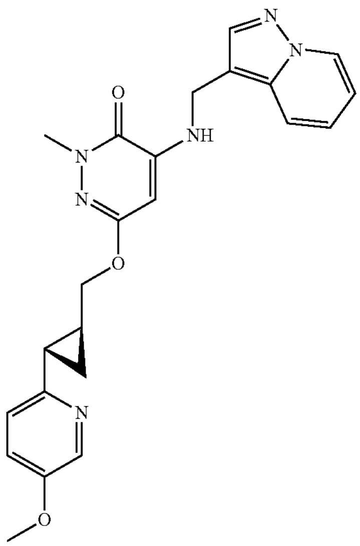 [SMILES: COc1ccc([C@H]2C[C@@H]2COc2cc(NCc3cnn4ccccc34)c(=O)n(C)n2)nc1] | 6-(((1S,2S)-2-(5-methoxy-pyridin-2-yl)cyclopropyl-)-methoxy)-2-methyl-4-((pyrazolo[1,5-a]pyridin-3-ylmethyl)amino)pyridazin-3(2H)-one | 433.1 |
| 79 | 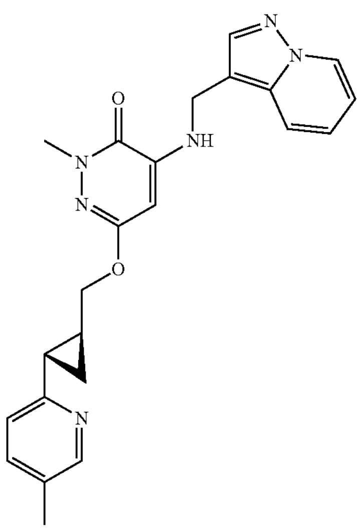 [SMILES: Cc1ccc([C@H]2C[C@@H]2COc2cc(NCc3cnn4ccccc34)c(=O)n(C)n2)nc1] | 2-methyl-6-(((1S,2S)-2-(5-methylpyridin-2-yl)cyclopropyl)methoxy)-4-((pyrazolo[1,5-a]pyridin-3-ylmethyl)amino)-pyridazin-3(2H)-one | 417.2 |
| 80 | 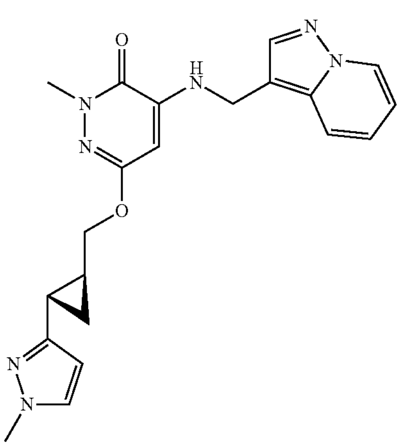 [SMILES: Cn1ccc([C@H]2C[C@@H]2COc2cc(NCc3cnn4ccccc34)c(=O)n(C)n2)n1] | 2-methyl-6-(((1S,2S)-2-(1-methyl-1H-pyrazol-3-yl)cyclopropyl)methoxy)-4-((pyrazolo[1,5-a]pyridin-3-ylmethyl)amino)-pyridazin-3(2H)-one | 406.2 |

TABLE 7-continued

| Example | Structure | IUPAC Name | LCMS m/z [M + H]+ |
|---------|-----------|------------|-------------------|
| 81 | 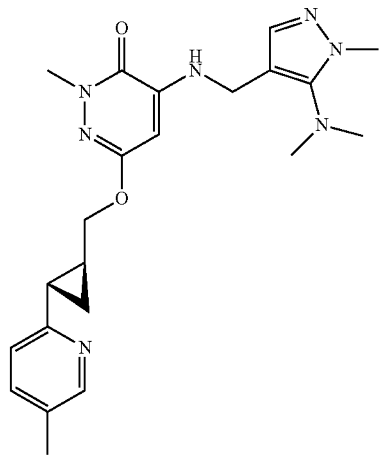 [SMILES: Cc1ccc([C@H]2C[C@@H]2COc2cc(NCc3cnn(C)c3N(C)C)c(=O)n(C)n2)nc1] | 4-(((5-(dimethylamino)-1-methyl-1H-pyrazol-4-yl)methyl)amino)-2-methyl-6-(((1S,2S)-2-(5-methylpyridin-2-yl)cyclopropyl)methoxy)-pyridazin-3(2H)-one | 424.2 |
| 82 | 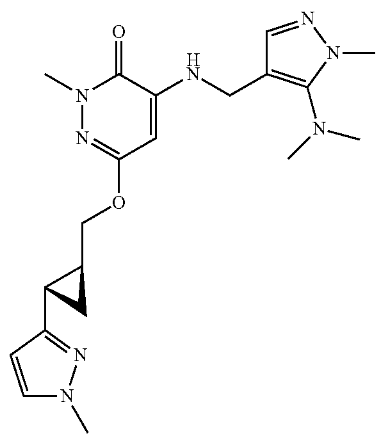 [SMILES: CN(C)c1c(CNc2cc(OC[C@H]3C[C@@H]3c3ccn(C)n3)nn(C)c2=O)cnn1C] | 4-(((5-(dimethylamino)-1-methyl-1H-pyrazol-4-yl)methyl)amino)-2-methyl-6-(((1S,2S)-2-(1-methyl-1H-pyrazol-3-yl)cyclopropyl)methoxy)-pyridazin-3(2H)-one | 413.2 |
| 83 | 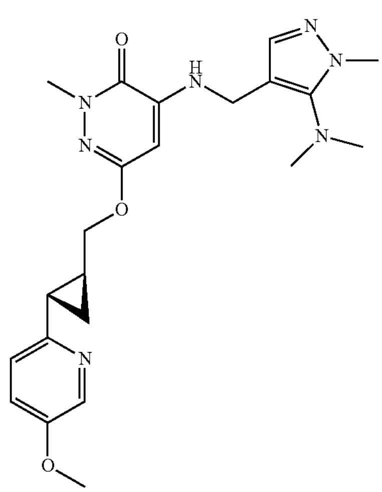 [SMILES: COc1ccc([C@H]2C[C@@H]2COc2cc(NCc3cnn(C)c3N(C)C)c(=O)n(C)n2)nc1] | 4-(((5-(dimethylamino)-1-methyl-1H-pyrazol-4-yl)methyl)amino)-6-(((1S,2S)-2-(5-methoxypyridin-2-yl)cyclopropyl)methoxy)-2-methylpyridazin-3(2H)-one | 440.2 |

TABLE 7-continued

| Example | Structure | IUPAC Name | LCMS m/z [M + H]+ |
|---|---|---|---|
| 84 | 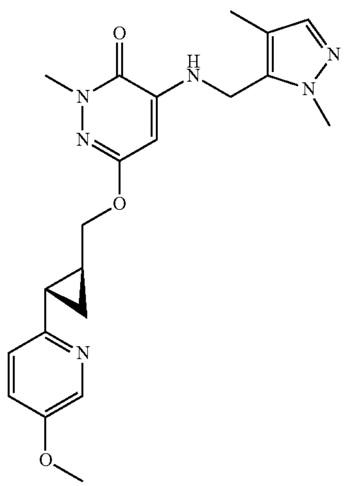 [SMILES: COc1ccc([C@H]2C[C@@H]2COc2cc(NCc3c(C)cnn3C)c(=O)n(C)n2)nc1] | 4-(((1,4-dimethyl-1H-pyrazol-5-yl)methyl)amino)-6-((((1S,2S)-2-(5-methoxypyridin-2-yl)cyclopropyl)methoxy)-2-methylpyridazin-3(2H)-one | 411.2 |
| 85 | 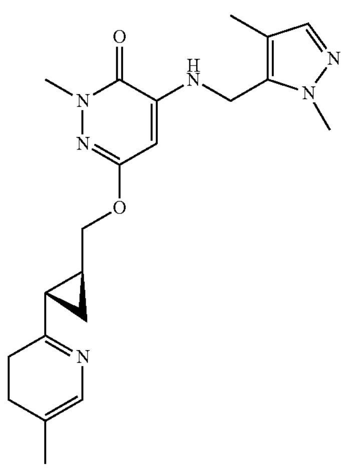 [SMILES: CC1=CN=C([C@H]2C[C@@H]2COc2cc(NCc3c(C)cnn3C)c(=O)n(C)n2)CC1] | 4-(((1,4-dimethyl-1H-pyrazol-5-yl)methyl)amino)-2-methyl-6-((((1S,2S)-2-(5-methylpyridin-2-yl)cyclopropyl)methoxy)-pyridazin-3(2H)-one | 395.2 |
| 86 | 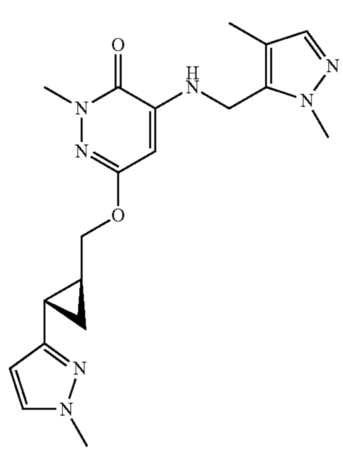 [SMILES: Cc1cnn(C)c1CNc1cc(OC[C@H]2C[C@@H]2c2ccn(C)n2)nn(C)c1=O] | 4-(((1,4-dimethyl-1H-pyrazol-5-yl)methyl)amino)-2-methyl-6-((((1S,2S)-2-(1-methyl-1H-pyrazol-3-yl)cyclopropyl)methoxy)-pyridazin-3(2H)-one | 384.2 |

TABLE 7-continued

| Example | Structure | IUPAC Name | LCMS m/z [M + H]+ |
|---|---|---|---|
| 87 | 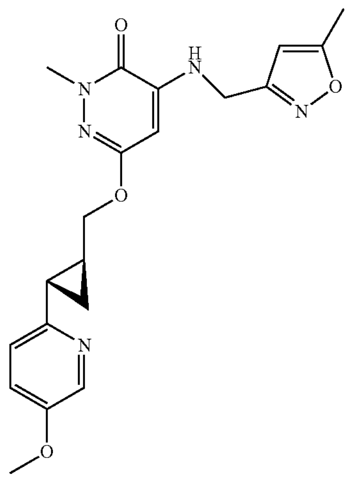 [SMILES: COc1ccc([C@H]2C[C@@H]2COc2cc(NCc3cc(C)on3)c(=O)n(C)n2)nc1] | 6-(((1S,2S)-2-(5-methoxypyridin-2-yl)cyclopropyl)methoxy)-2-methyl-4-(((5-methylisoxazol-3-yl)methyl)amino)pyridazin-3(2H)-one | 398.2 |
| 88 | 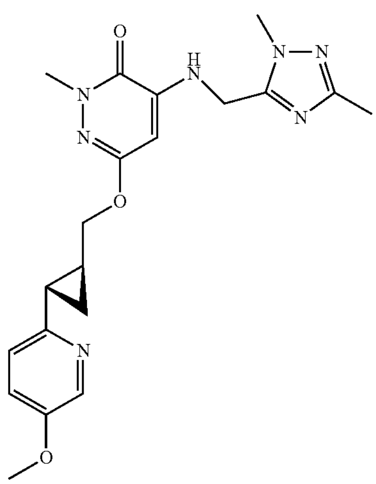 [SMILES: COc1ccc([C@H]2C[C@@H]2COc2cc(NCc3nc(C)nn3C)c(=O)n(C)n2)nc1] | 4-(((1,3-dimethyl-1H-1,2,4-triazol-5-yl)methyl)amino)-6-(((1S,2S)-2-(5-methoxypyridin-2-yl)cyclopropyl)methoxy)-2-methylpyridazin-3(2H)-one | 412.2 |
| 89 | 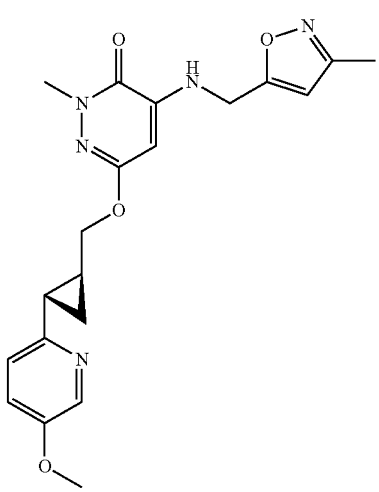 [SMILES: COc1ccc([C@H]2C[C@@H]2COc2cc(NCc3cc(C)no3)c(=O)n(C)n2)nc1] | 6-(((1S,2S)-2-(5-methoxypyridin-2-yl)cyclopropyl)methoxy)-2-methyl-4-(((3-methylisoxazol-5-yl)methyl)amino)pyridazin-3(2H)-one | 398.2 |

TABLE 7-continued
| Example | Structure | IUPAC Name | LCMS m/z [M + H]+ |
|---|---|---|---|
| 90 | 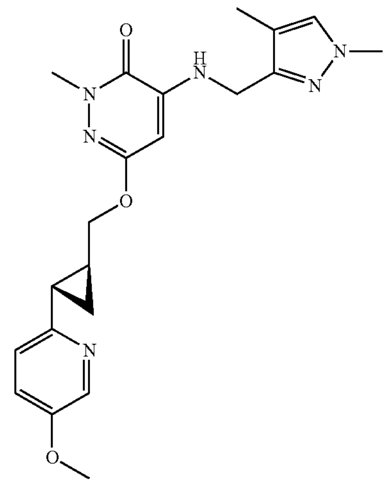 [SMILES: COc1ccc([C@H]2C[C@@H]2COc2cc(NCc3nn(C)cc3C)c(=O)n(C)n2)nc1] | 4-(((1,4-dimethyl-1H-pyrazol-3-yl)methyl)amino)-6-(((1S,2S)-2-(5-methoxypyridin-2-yl)cyclopropyl)methoxy)-2-methylpyridazin-3(2H)-one | 410.2 |
| 91 | 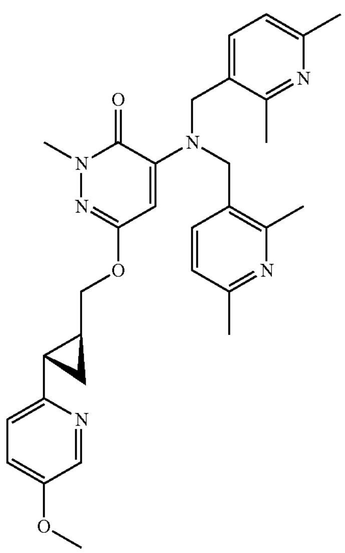 [SMILES: COc1ccc([C@H]2C[C@@H]2COc2cc(N(Cc3ccc(C)nc3C)Cc3ccc(C)nc3C)c(=O)n(C)n2)nc1] | 4-(bis((2,6-dimethylpyridin-3-yl)methyl)amino)-6-(((1S,2S)-2-(5-methoxypyridin-2-yl)cyclopropyl)methoxy)-2-methylpyridazin-3(2H)-one | 541.1 |
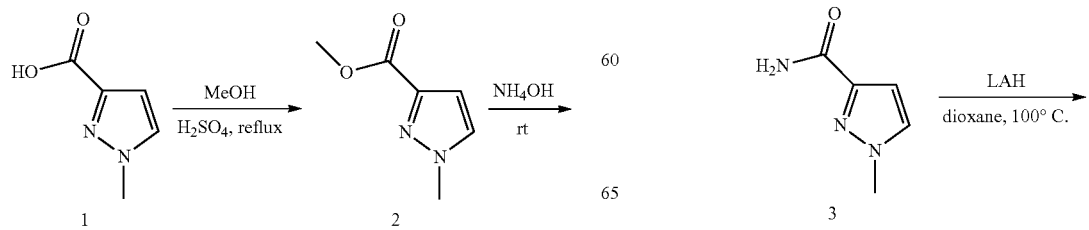
Scheme 6

101
-continued

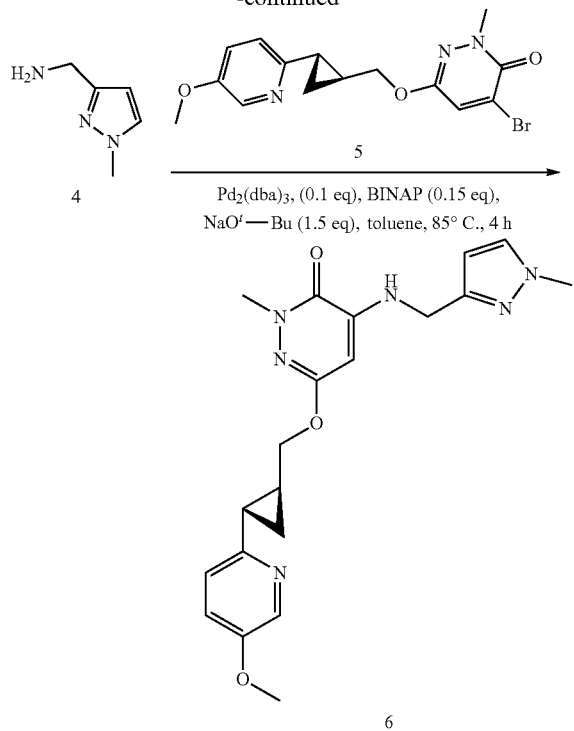

Examples 92-107

Referring to Scheme 6

Step A: Methyl 1-methyl-1H-pyrazole-3-carboxylate (2)

To a solution of compound 1 (1.26 g, 10 mmol) in methanol (30 mL) was added sulfuric acid (0.5 mL). The resulting mixture was refluxed for 2 h and the solvent was evaporated. The residue was dissolved in EA (60 mL) and washed with brine, dried over $Na_2SO_4$. Then filtered and concentrated to give the product.

102

Step B: 1-Methyl-1H-pyrazole-3-carboxamide (3)

A solution of methyl 1-methyl-1H-pyrazole-3-carboxylate (1.1 g, 7.9 mmol) in $NH_3.H_2O$ (10 mL) was stirred for 2 h at room temperature. The solvent was evaporated to give the crude product which was used for the next step without further purification.

Step C: (1-Methyl-1H-pyrazol-3-yl)methanamine (4)

To a solution of 1-methyl-1H-pyrazole-3-carboxamide (400 mg, 3.2 mmol) in dioxane (30 mL) was added LAH (365 mg, 9.6 mmol). The resulting mixture was stirred for 3 h at 100° C. After it was cooled to 0° C., it was quenched with 0.4 ml water, 0.4 mL 15% NaOH aqueous, 1.2 mL water in turn. Anhydrous sodium sulfate was added to the solution. The mixture was filtered and concentrated to give the crude product which was used for the next step directly.

Step D: 6-(((1S,2S)-2-(5-methoxypyridin-2-cyclopropyl)methoxy)-2-meth-4-((1-methyl-1H-pyrazol-3-yl)methylamino)pyridazin-3(2H)-one (6)

To the solution of 4-bromo-6-(((1S,2S)-2-(5-methoxypyridin-2-yl)cyclopropyl)methoxy)-2-methylpyridazin-3(2H)-one (73 mg, 0.2 mmol) in toluene (4 mL) under $N_2$, (1-methyl-1H-pyrazol-3-yl)methanamine (22 mg, 0.2 mmol), $Pd_2(dba)_3$ (18 mg, 0.02 mmol), BINAP (18 mg, 0.03 mmol) and $NaO^tBu$ (29 mg, 0.3 mmol) were added. After the reaction mixture was stirred at 85° C. for 4 h, 15 mL water was added. The mixture was extracted with EtOAc (3×10 mL). The combined organics were dried over $MgSO_4$, filtered and concentrated in vacuo. The residue was purified by Pre-HPLC to afford the title compound as a solid. 1H NMR (400 MHz, MeOD) δ 8.06 (d, 1H), 7.50 (d, 1H), 7.30 (dd, 1H), 7.17 (d, 1H), 6.21 (d, 1H), 5.83 (s, 1H), 4.32 (s, 2H), 4.18-4.14 (m, 1H), 4.06-4.02 (m, 1H), 3.87 (s, 3H), 3.84 (s, 3H), 3.62 (s, 3H), 2.09-2.04 (m, 1H), 1.76-1.72 (m, 1H), 1.20-1.15 (m, 1H), 1.05-1.00 (m, 1H); LRMS m/z (M+H) 397.2 found, 397.19 required.

The following Examples 92-107 were prepared using the procedure of Example 92, substituting the appropriate starting materials.

TABLE 8

| Example | Structure | IUPAC Name | LCMS m/z [M + H]+ |
|---|---|---|---|
| 92 | 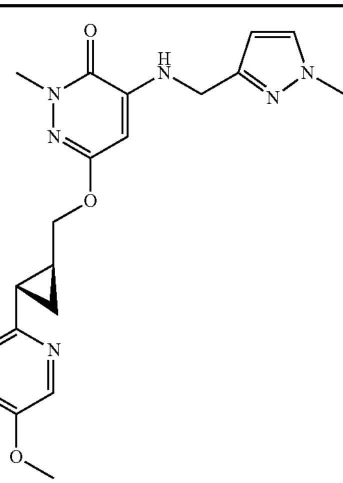 | 6-(((1S,2S)-2-(5-methoxy-pyridin-2-yl)cyclopropyl-)methoxy)-2-methyl-4-(((1-methyl-1H-pyrazol-3-yl)methyl)-amino)-pyridazin-3(2H)one | 397.2 |

TABLE 8-continued

| Example | Structure | IUPAC Name | LCMS m/z [M + H]+ |
|---|---|---|---|
| 93 | 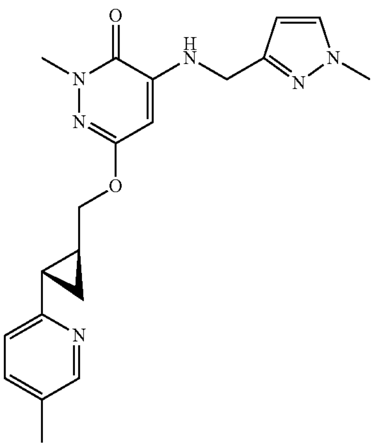 [SMILES: Cc1ccc([C@H]2C[C@@H]2COc2cc(NCc3ccn(C)n3)c(=O)n(C)n2)nc1] | 2-methyl-4-(((1-methyl-1H-pyrazol-3-yl)methyl)-amino)-6-(((1S,2S)-2-(5-methylpyridin-2-yl)cyclopropyl)methoxy)pyridazin-3(2H)-one | 381.2 |
| 94 | 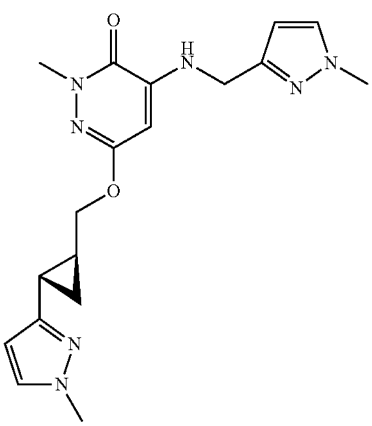 [SMILES: Cn1ccc(CNc2cc(OC[C@H]3C[C@@H]3c3ccn(C)n3)nn(C)c2=O)n1] | 2-methyl-6-(((1S,2S)-2-(1-methyl-1H-pyrazol-3-yl)cyclopropyl)methoxy)-4-(((1-methyl-1H-pyrazol-3-yl)methyl)amino)-pyridazin-3(2H)-one | 370.2 |
| 95 | 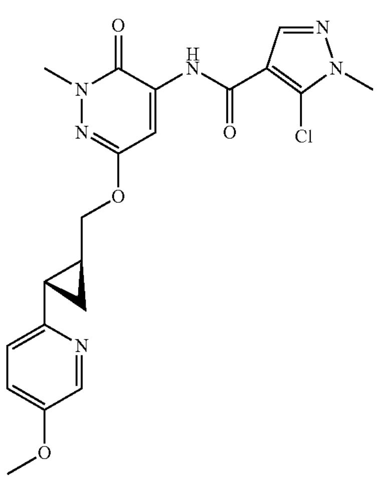 [SMILES: COc1ccc([C@H]2C[C@@H]2COc2cc(NC(=O)c3cnn(C)c3Cl)c(=O)n(C)n2)nc1] | 5-chloro-N-(6-(((1S,2S)-2-(5-methoxypyridin-2-yl)-cyclopropyl)methoxy)-2-methyl-3-oxo-2,3-dihydro-pyridazin-4-yl)-1-methyl-1Hpyrazole-4carboxamide | 445.2 |

TABLE 8-continued

| Example | Structure | IUPAC Name | LCMS m/z [M + H]+ |
|---|---|---|---|
| 96 | 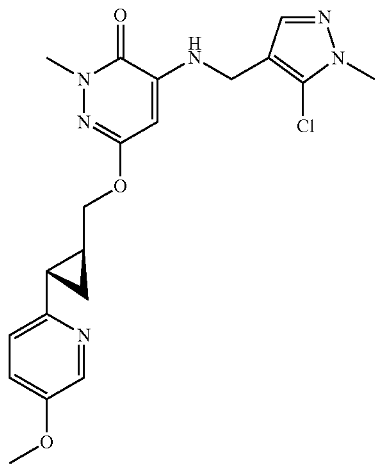 [SMILES: COc1ccc([C@H]2C[C@@H]2COc2cc(NCc3cnn(C)c3Cl)c(=O)n(C)n2)nc1] | 4-(((5-chloro-1-methyl-1H-pyrazol-4-yl)methyl)-amino)-6-((((1S,2S)-2-(5-methoxypyridin-2-yl)-cyclopropyl)methoxy)-2-methylpyridazin-3(2H)one | 431.1 |
| 97 | 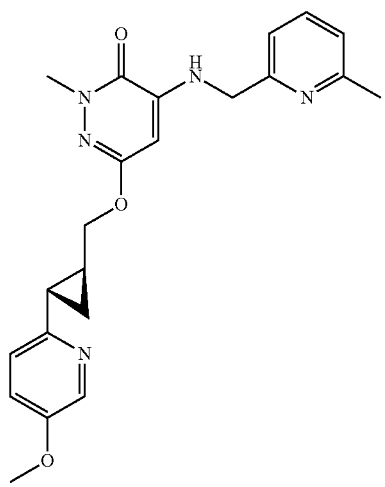 [SMILES: COc1ccc([C@H]2C[C@@H]2COc2cc(NCc3cccc(C)n3)c(=O)n(C)n2)nc1] | 6-((((1S,2S)-2-(5-methoxypyridin-2-yl)-cyclopropyl)methoxy)-2-methyl-4-(((6-methyl-pyridin-2-yl)methyl)-amino)pyridazin-3(2H)one | 408.2 |
| 98 | 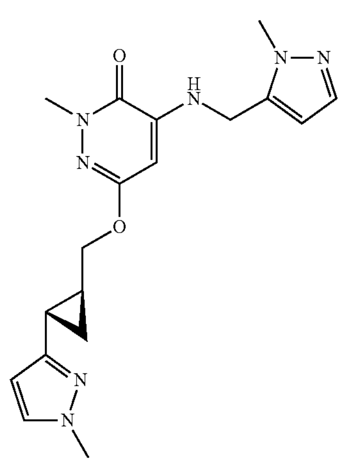 [SMILES: Cn1ccc([C@H]2C[C@@H]2COc2cc(NCc3ccnn3C)c(=O)n(C)n2)n1] | 2-methyl-6-((((1S,2S)-2-(1-methyl-1H-pyrazol-3-yl)cyclopropyl)methoxy)-4-(((1-methyl-1H-pyrazol-5-yl)methyl)amino)-pyridazin-3(2H)-one | 370.2 |

TABLE 8-continued

| Example | Structure | IUPAC Name | LCMS m/z [M + H]+ |
|---|---|---|---|
| 99 | 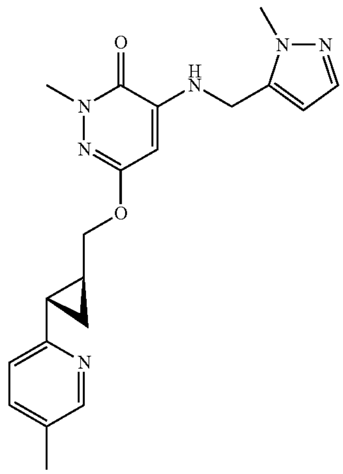 [SMILES: Cc1ccc([C@H]2C[C@@H]2COc2cc(NCc3ccnn3C)c(=O)n(C)n2)nc1] | 2-methyl-4-(((1-methyl-1H-pyrazol-5-yl)methyl-)amino)-6-(((1S,2S)-2-(5-methylpyridin-2-yl)cyclopropyl)methoxy)pyridazin-3(2H)-one | 381.2 |
| 100 | 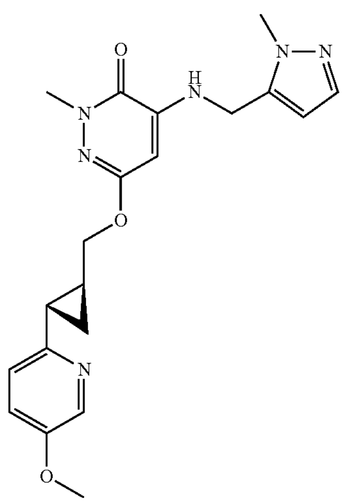 [SMILES: COc1ccc([C@H]2C[C@@H]2COc2cc(NCc3ccnn3C)c(=O)n(C)n2)nc1] | 6-(((1S,2S)-2-(5-methoxypyridin-2-yl)-cyclopropyl)methoxy)-2-methyl-4-(((1-methyl-1H-pyrazol-5-yl)methyl)-amino)pyridazin-3(2H)one | 397.2 |
| 101 | 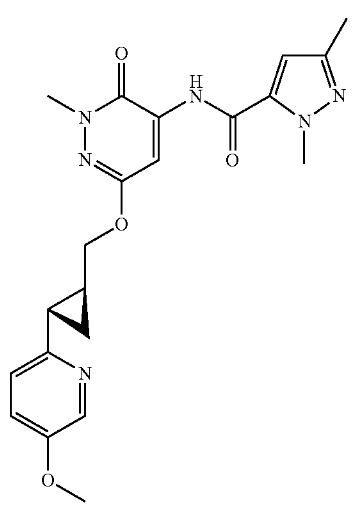 [SMILES: COc1ccc([C@H]2C[C@@H]2COc2cc(NC(=O)c3cc(C)nn3C)c(=O)n(C)n2)nc1] | N-(6-(((1S,2S)-2-(5-methoxypyridin-2-yl)-cyclopropyl)methoxy)-2-methyl-3-oxo-2,3-dihydropyridazin-4-yl)-1,3-dimethyl-1H-pyrazole-5-carboxamide | 425.2 |

TABLE 8-continued

| Example | Structure | IUPAC Name | LCMS m/z [M + H]+ |
|---|---|---|---|
| 102 | 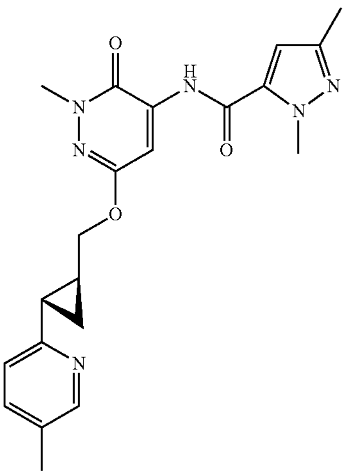 [SMILES: Cc1ccc([C@H]2C[C@@H]2COc2cc(NC(=O)c3cc(C)nn3C)c(=O)n(C)n2)nc1] | 1,3-dimethyl-N-(2-methyl-6-((((1S,2S)-2-(5-methyl-pyridin-2-yl)cyclopropyl-)methoxy)-3-oxo-2,3-dihydropyridazin-4-yl)-1H-pyrazole-5-carboxamide | 409.2 |
| 103 | 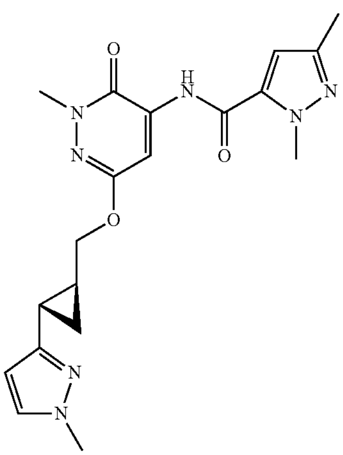 [SMILES: Cc1cc(C(=O)Nc2cc(OC[C@H]3C[C@@H]3c3ccn(C)n3)nn(C)c2=O)n(C)n1] | 1,3-dimethyl-N-(2-methyl-6-(((1S,2S)-2-(1-methyl-1H-pyrazol-3-yl)cyclopropyl)methoxy)-3-oxo-2,3-dihydropyridazin-4-yl)-1H-pyrazole-5-carboxamide | 398.2 |
| 104 | 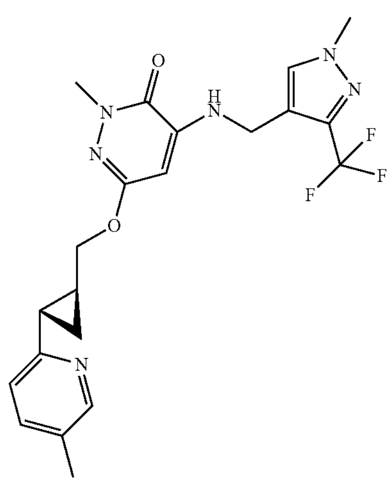 [SMILES: Cc1ccc([C@H]2C[C@@H]2COc2cc(NCc3cn(C)nc3C(F)(F)F)c(=O)n(C)n2)nc1] | 2-methyl-4-(((1-methyl-3-(trifluoromethyl)-1H-pyrazol-4-yl)methyl)-amino)-6-(((1S,2S)-2-(5-methylpyridin-2-yl)cyclopropyl)methoxy)pyridazin-3(2H)-one | 449.2 |

TABLE 8-continued

| Example | Structure | IUPAC Name | LCMS m/z [M + H]+ |
|---|---|---|---|
| 105 | 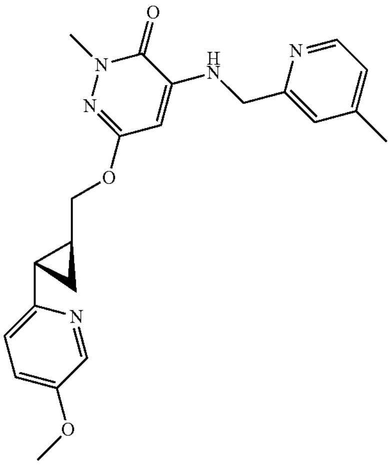 [SMILES: COc1ccc([C@H]2C[C@@H]2COc2cc(NCc3cc(C)ccn3)c(=O)n(C)n2)nc1] | 6-(((1S,2S)-2-(5-methoxy-pyridin-2-yl)cyclopropyl-)methoxy)-2-methyl-4-(((-4-methylpyridin-2-yl)-methyl)amino)pyridazin-3(2H)-one | 408.2 |
| 106 | 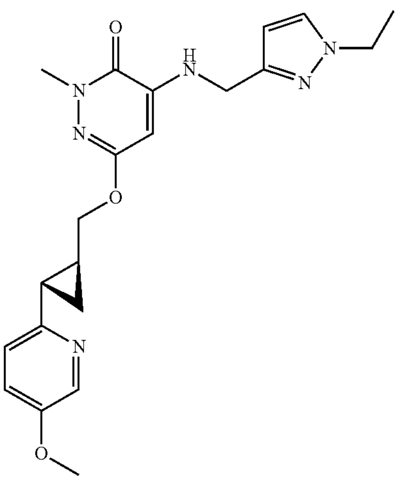 [SMILES: CCn1ccc(CNc2cc(OC[C@H]3C[C@@H]3c3ccc(OC)cn3)nn(C)c2=O)n1] | 4-(((1-ethyl-1H-pyrazol-3-yl)methyl)amino)-6-(((-1S,2S)-2-(5-methoxy-pyridin-2-yl)cyclopropyl-)methoxy)-2-methyl-pyridazin-3(2H)-one | 411.2 |
| 107 | 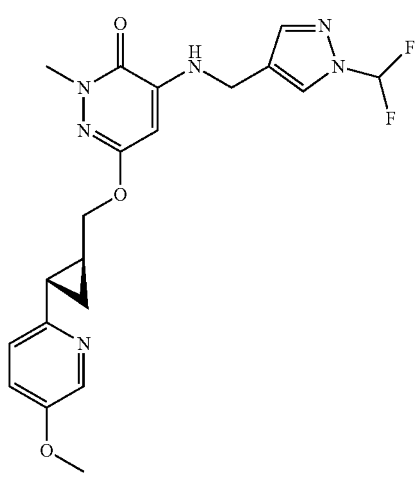 [SMILES: COc1ccc([C@H]2C[C@@H]2COc2cc(NCc3cnn(C(F)F)c3)c(=O)n(C)n2)nc1] | 4-((1-(difluoromethyl)-1H-pyrazol-4-yl)methyl-amino)-6-(((1S,2S)-2-(5-methoxypyridin-2-yl)-cyclopropyl)methoxy)-2-methylpyridazin-3(2H)one | 432.1 |

Scheme 7

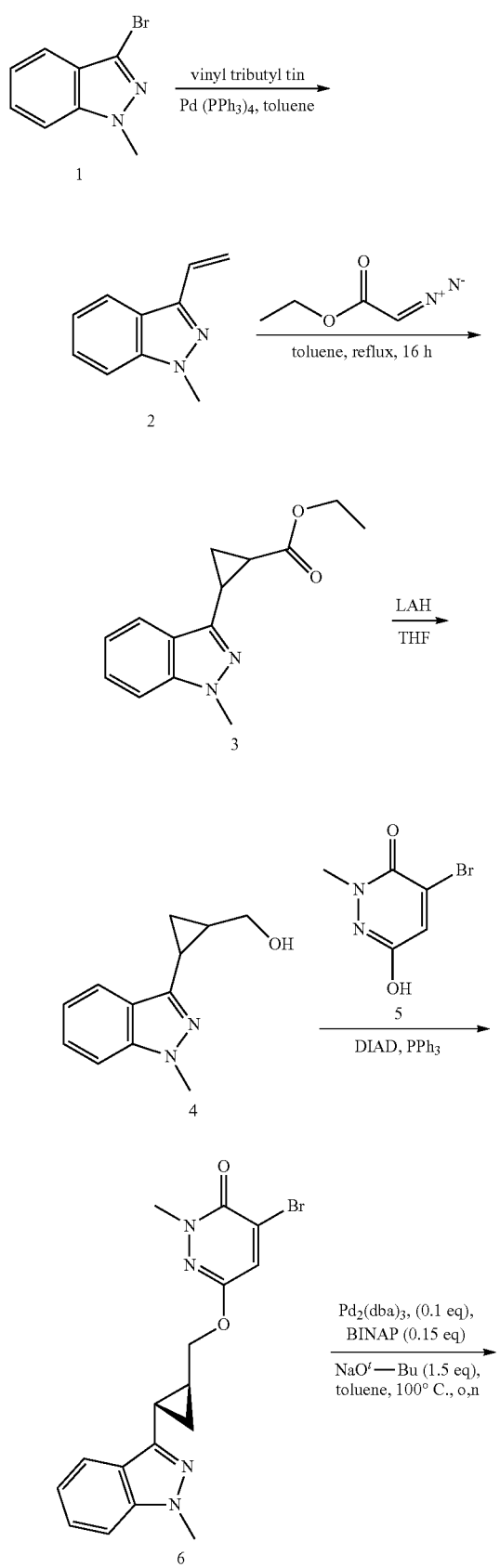

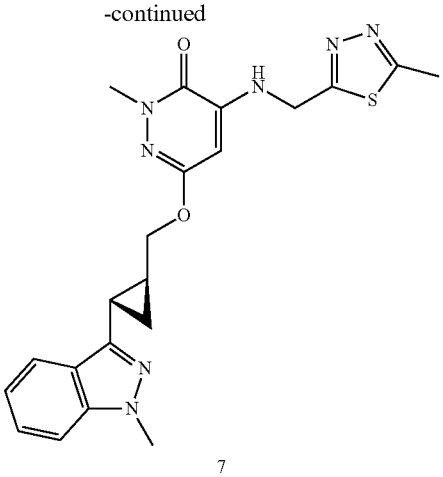

Examples 108-125

Referring to Scheme 7

Step A: 1-methyl-3-vinyl-1H-indazole (2)

A solution of compound 1 (1.6 g, 8 mmol) and vinyl tributyl tin (2.6 mL, 11 mmol) in toluene (10 mL) was treated with Pd(PPh$_3$)$_4$ (0.92 g, 0.8 mmol) and heated to reflux overnight. The reaction mixture was concentrated and the resulting material was purified directly by gradient elution on silica gel (0 to 20% EtOAc in hexanes) to afford the title compound as a colorless oil.

Step B: ethyl 2-(1-methyl-1H-indazol-3-yl)cyclopropanecarboxylate (3)

A solution of compound 2 (1.1 g, 7 mmol) in toluene (5 mL) was treated with ethyl diazoacetate (1.2 g, 10 mmol) and stirred at reflux overnight under N$_2$. The mixture was concentrated and the residue was purified by gradient elution on silica gel (PE: EA=5:1) to afford the title compound as a pale yellow oil.

Step C: (2-(1-methyl-1H-indazol-3-yl)cyclopropyl)methanol (4)

A solution of ethyl 2-(1-methyl-1H-indazol-3-yl)cyclopropanecarboxylate (1.17 g, 5 mmol) in THF (20 mL) was cooled to 0° C. and treated slowly with LAH (270 mg, 7 mmol). The solution was warmed to room temperature and stirred overnight. The reaction mixture was then re-cooled to 0° C. and treated sequentially with 0.3 mL of water, 0.3 mL of 15% NaOH, and 0.9 mL of water. Sodium sulfate was added to the mixture. After stirring at room temperature for 10 min, the mixture was filtered through a pad of Celite and the filtrate was concentrated in vacuo to afford the title compound as pale yellow oil. LRMS m/z (M+H) 204.1 found, 204.1 required. Enantiomers can be resolved by chiral analytical SFC ((R,R)-Whelk-O1 4.6*250 mm 5 um) ent1=4.37 min (1S,2S) (active isomer, 360 mg), ent2=5.33 min.

Step D: 4-bromo-2-methyl-6-(((1S,2S)-2-(1-methyl-1H-indazol-3-yl)cyclopropyl)methoxy)pyridazin-3(2H)-one (6)

To a solution of 5-bromo-1-methyl-1,2-dihydropyridazine-3,6-dione (300 mg, 1.485 mmol) in THF (20 mL) at 0° C. was added PPh₃ (781 mg, 2.97 mmol) and ((1S,2S)-2-(1-methyl-1H-indazol-3-yl)cyclopropyl)methanol (300 mg, 1.485 mmol) followed by dropwise addition of DIAD (0.6 mL, 2.97 mmol). The reaction mixture was warmed to ambient temperature. After stirred for 2 h, the mixture was concentrated. The residue was purified by column chromatography on silica gel, eluting with PE/EA (2/1) to give the title compound as oil.

Step E: 2-methyl-4-((5-methyl-1,34-thiadiazol-2-yl)methylamino)-6-(((1S,2S)-2-(1-methyl-1H-indazol-3-yl)cyclopropyl)methoxy)pyridazin-3(2H)-one (7)

To the solution of 4-bromo-2-methyl-6-(((1S,2S)-2-(1-methyl-1H-indazol-3-yl)cyclopropyl)methoxy)pyridazin-3(2H)-one (50 mg, 0.13 mmol) in toluene (5 mL) under N₂, (5-methyl-1,3,4-thiadiazol-2-yl)methanamine (23 mg, 0.14 mmol), Pd₂(dba)₃ (12 mg, 0.019 mmol), BINAP (12 mg, 0.025 mmol) and NaO$^t$Bu (18 mg, 0.2 mmol) were added. After the reaction mixture was stirred at 100° C. overnight, 15 mL water was added. The mixture was extracted with EtOAc (3×10 mL). The combined organics were dried over MgSO₄, filtered and concentrated in vacuo. The residue was purified by Pre-HPLC to afford the title compound as a solid. 1H NMR (400 MHz, MeOD) δ 7.71 (d, 1H), 7.39-7.26 (m, 2H), 7.11 (d, 1H), 6.34 (t, 1H), 5.85 (s, 1H), 4.75 (d, 2H), 4.19-4.04 (m, 2H), 3.98 (s, 3H), 3.66 (s, 3H), 2.75 (s, 3H), 2.25-2.20 (m, 1H), 1.90-1.86 (m, 1H), 1.42-1.25 (m, 1H), 1.11-1.05 (m, 1H); LRMS m/z (M+H) 438.2 found, 438.2 required.

The following Examples 108-125 were prepared using the procedure of Example 108 substituting the appropriate starting materials.

TABLE 9

| Example | Structure | IUPAC Name | LCMS m/z [M + H]⁺ |
|---|---|---|---|
| 108 | 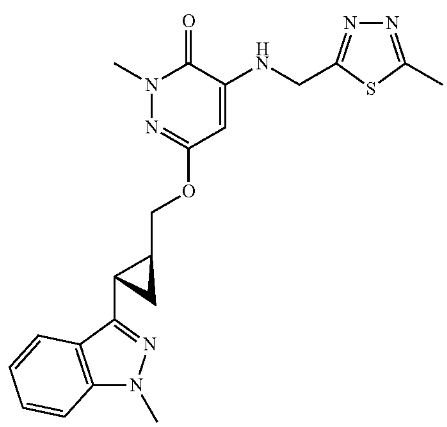 | 2-methyl-4-((5-methyl-1,3,4-thiadiazol-2-yl)-methylamino)-6-(((1S,2S)-2-(1-methyl-1H-indazol-3-yl)cyclopropyl)methoxy)pyridazin-3(2H)-one | 438.2 |
| 109 | 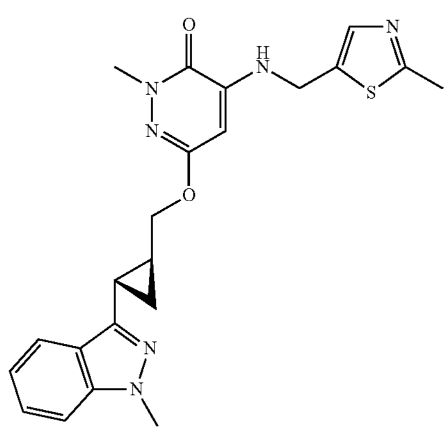 [SMILES: Cc1ncc(CNc2cc(OC[C@H]3C[C@@H]3c3nn(C)c4ccccc34)nn(C)c2=O)s1] | 2-methyl-6-(((1S,2S)-2-(1-methyl-1H-indazol-3-yl)cyclopropyl)methoxy)-4-((2-methylthiazol-5-yl)methylamino)pyridazin-3(2H)-one | 437.1 |

TABLE 9-continued

| Example | Structure | IUPAC Name | LCMS m/z [M + H]+ |
|---|---|---|---|
| 110 | 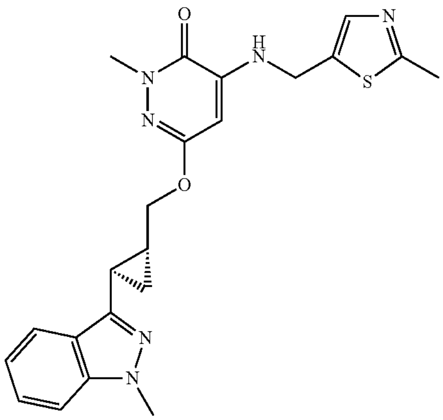 [SMILES: Cc1ncc(CNc2cc(OC[C@@H]3C[C@H]3c3nn(C)c4ccccc34)nn(C)c2=O)s1] | 2-methyl-6-(((1R,2R)-2-(1-methyl-1H-indazol-3-yl)cyclopropyl)methoxy)-4-((2-methylthiazol-5-yl)methylamino)pyridazin-3(2H)-one | 437.1 |
| 111 | 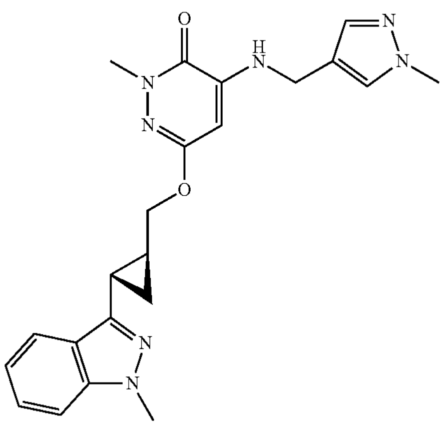 [SMILES: Cn1cc(CNc2cc(OC[C@H]3C[C@@H]3c3nn(C)c4ccccc34)nn(C)c2=O)cn1] | 2-methyl-6-(((1S,2S)-2-(1-methyl-1H-indazol-3-yl)cyclopropyl)methoxy)-4-((1-methyl-1H-pyrazol-4-yl)methylamino)-pyridazin-3(2H)-one | 420.1 |
| 112 | 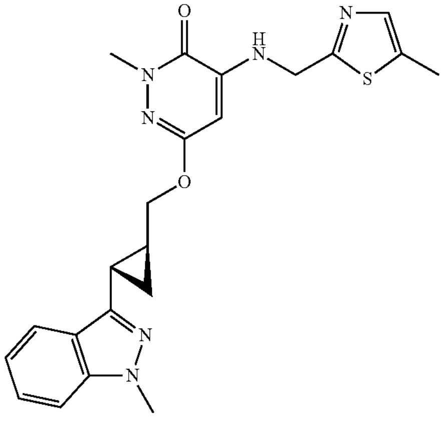 [SMILES: Cc1cnc(CNc2cc(OC[C@H]3C[C@@H]3c3nn(C)c4ccccc34)nn(C)c2=O)s1] | 2-methyl-6-(((1S,2S)-2-(1-methyl-1H-indazol-3-yl)cyclopropyl)methoxy)-4-((5-methylthiazol-2-yl)methylamino)pyridazin-3(2H)-one | 437.1 |

TABLE 9-continued

| Example | Structure | IUPAC Name | LCMS m/z [M + H]+ |
|---|---|---|---|
| 113 | 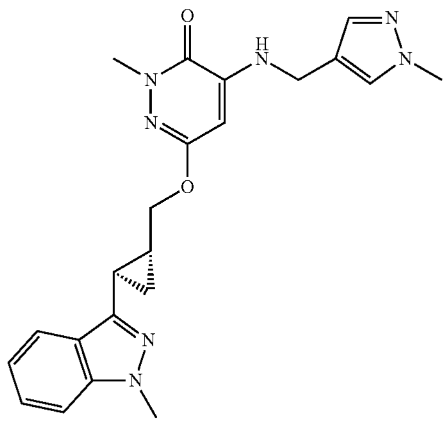 [SMILES: Cn1cc(CNc2cc(OC[C@@H]3C[C@H]3c3nn(C)c4ccccc34)nn(C)c2=O)cn1] | 2-methyl-6-(((1R,2R)-2-(1-methyl-1H-indazol-3-yl)cyclopropyl)methoxy)-4-((1-methyl-1H-pyrazol-4-yl)methylamino)pyridazin-3(2H)-one | 420.2 |
| 114 | 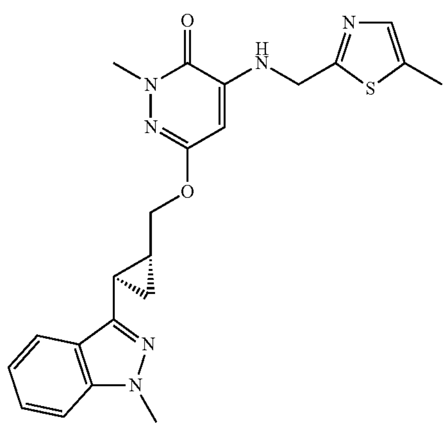 [SMILES: Cc1cnc(CNc2cc(OC[C@@H]3C[C@H]3c3nn(C)c4ccccc34)nn(C)c2=O)s1] | 2-methyl-6-(((1R,2R)-2-(1-methyl-1H-indazol-3-yl)cyclopropyl)methoxy)-4-((5-methylthiazol-2-yl)methylamino)pyridazin-3(2H)-one | 437.1 |
| 115 | 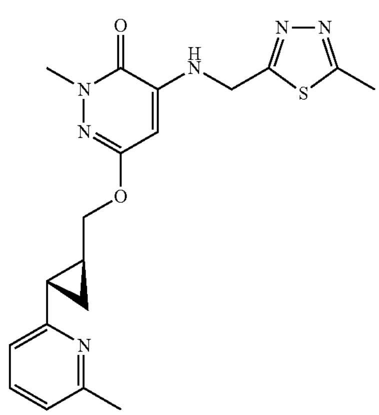 [SMILES: Cc1cccc([C@H]2C[C@@H]2COc2cc(NCc3nnc(C)s3)c(=O)n(C)n2)n1] | 2-methyl-4-((5-methyl-1,3,4-thiadiazol-2-yl)methylamino)-6-(((1S,2S)-2-(6-methylpyridin-2-yl)cyclopropyl)methoxy)pyridazin-3(2H)-one | 399.1 |

TABLE 9-continued

| Example | Structure | IUPAC Name | LCMS m/z [M + H]+ |
|---|---|---|---|
| 116 | 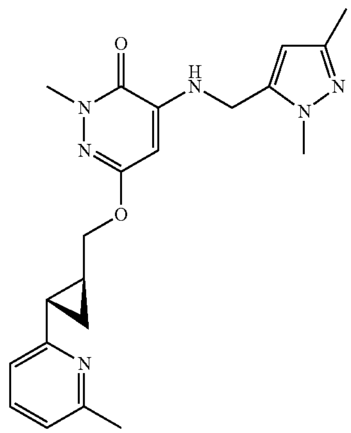 [SMILES: Cc1cccc([C@H]2C[C@@H]2COc2cc(NCc3cc(C)nn3C)c(=O)n(C)n2)n1] | 4-((1,3-dimethyl-1H-pyrazol-5-yl)methylamino)-2-methyl-6-(((1S,2S)-2-(6-methylpyridin-2-yl)cyclopropyl)methoxy)pyridazin-3(2H)-one | 395.2 |
| 117 | 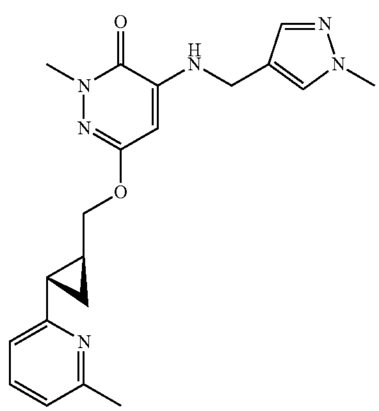 [SMILES: Cc1cccc([C@H]2C[C@@H]2COc2cc(NCc3cnn(C)c3)c(=O)n(C)n2)n1] | 2-methyl-4-((1-methyl-1H-pyrazol-4-yl)methyl-amino)-6-(((1S,2S)-2-(6-methylpyridin-2-yl)cyclopropyl)methoxy)pyridazin-3(2H)-one | 381.2 |
| 118 | 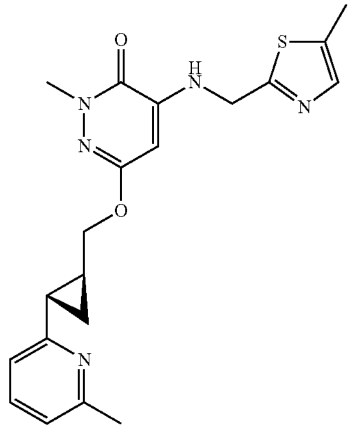 [SMILES: Cc1cccc([C@H]2C[C@@H]2COc2cc(NCc3ncc(C)s3)c(=O)n(C)n2)n1] | 2-methyl-6-(((1S,2S)-2-(6-methylpyridin-2-yl)cyclopropyl)methoxy)-4-((5-methylthiazol-2-yl)methyl-amino)pyridazin-3(2H)one | 398.2 |

TABLE 9-continued

| Example | Structure | IUPAC Name | LCMS m/z [M + H]+ |
|---|---|---|---|
| 119 | 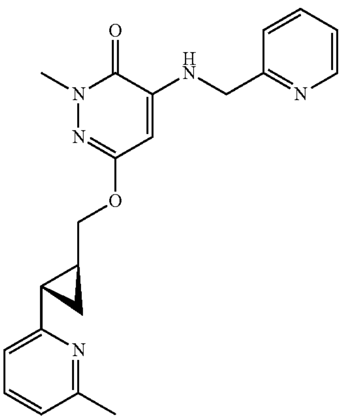 [SMILES: Cc1cccc([C@H]2C[C@@H]2COc2cc(NCc3ccccn3)c(=O)n(C)n2)n1] | 2-methyl-6-((((1S,2S)-2-(6-methylpyridin-2-yl)cyclo-propyl)methoxy)-4-(pyridin-2-ylmethylamino-)pyridazin-3(2H)-one | 378.2 |
| 120 | 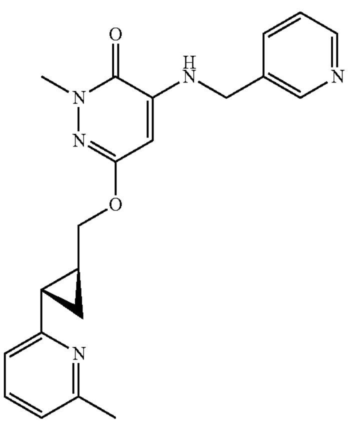 [SMILES: Cc1cccc([C@H]2C[C@@H]2COc2cc(NCc3cccnc3)c(=O)n(C)n2)n1] | 2-methyl-6-((((1S,2S)-2-(6-methylpyridin-2-yl)cyclo-propyl)methoxy)-4-(pyridin-3-ylmethylamino-)pyridazin-3(2H)-one | 378.2 |
| 121 | 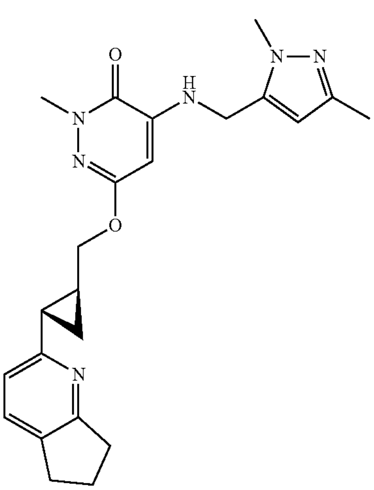 [SMILES: Cc1cc(CNc2cc(OC[C@H]3C[C@@H]3c3ccc4c(n3)CCC4)nn(C)c2=O)n(C)n1] | 6-((((1S,2S)-2-(6,7-dihydro-5H-cyclopenta-[b]pyridin-2-yl)cyclop-ropyl)methoxy)-4-((1,3-dimethyl-1H-pyrazol-5-yl)methylamino)-2-methylpyridazin-3(2H)one | 421.3 |

TABLE 9-continued

| Example | Structure | IUPAC Name | LCMS m/z [M + H]+ |
|---|---|---|---|
| 122 | 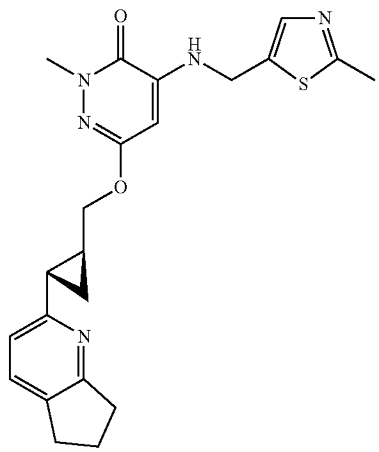 [SMILES: Cc1ncc(CNc2cc(OC[C@H]3C[C@@H]3c3ccc4c(n3)CCC4)nn(C)c2=O)s1] | 6-(((1S,2S)-2-(6,7-dihydro-5H-cyclopenta-[b]pyridin-2-yl)cyclo-propyl)-methoxy)-2-methyl-4-((2-methylthiazol-5-yl)methyl-amino)pyridazin-3(2H)one | 424.2 |
| 123 | 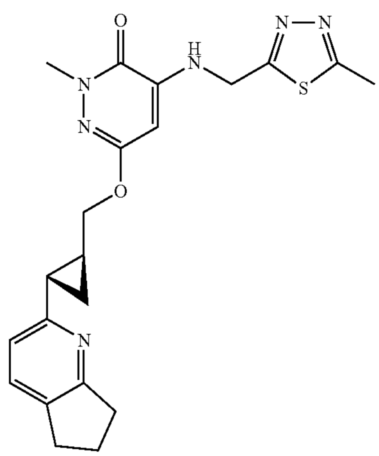 [SMILES: Cc1nnc(CNc2cc(OC[C@H]3C[C@@H]3c3ccc4c(n3)CCC4)nn(C)c2=O)s1] | 6-(((1S,2S)-2-(6,7-dihydro-5H-cyclopenta-[b]pyridin-2-yl)cyclopropyl)methoxy)-2-methyl-4-((5-methyl-1,3,4-thia-diazol-2-yl)-methylamino)-pyridazin-3(2H)-one | 425.1 |
| 124 | 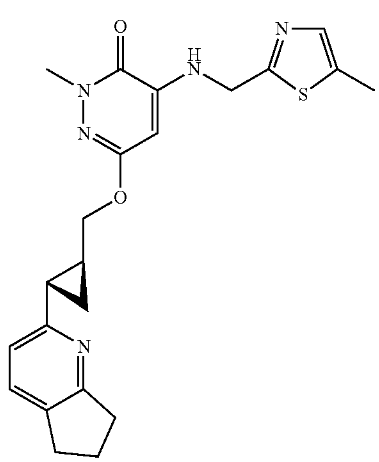 [SMILES: Cc1cnc(CNc2cc(OC[C@H]3C[C@@H]3c3ccc4c(n3)CCC4)nn(C)c2=O)s1] | 6-(((1S,2S)-2-(6,7-dihydro-5H-cyclopenta-[b]pyridin-2-yl)cyclopropyl)methoxy)-2-methy-4-((5-methyl thiazol-2-yl)-methylamino-)pyridazin-3(2H)-one | 424.2 |

TABLE 9-continued

| Example | Structure | IUPAC Name | LCMS m/z [M + H]+ |
|---|---|---|---|
| 125 | 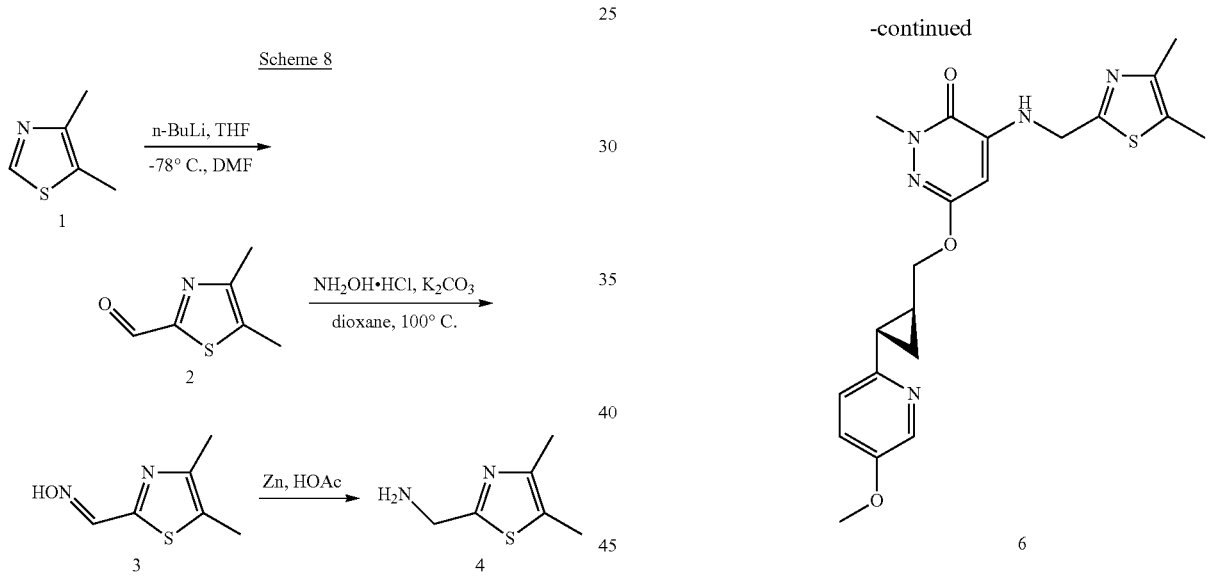 | 6-(((1S,2S)-2-(6,7-dihydro-5H-cyclopenta[b]pyridin-2-1)cyclopropyl)methoxy)-2-methyl-4-((1-methyl-1H-pyrazol-4-yl)methylamino-)pyridazin-3(2H)-one | 407.2 |

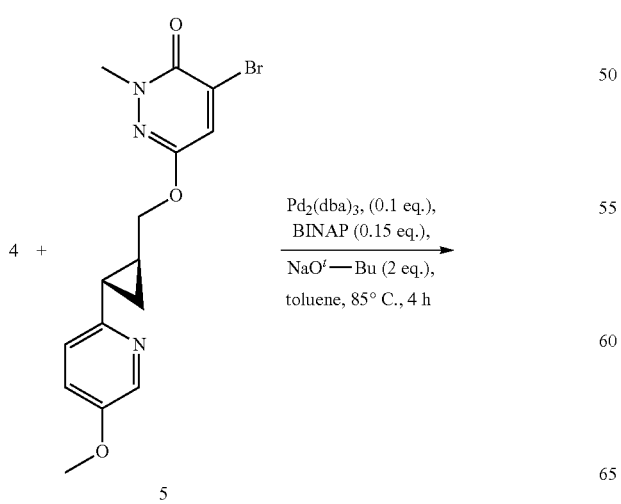

Scheme 8

Examples 126-136

Referring to Scheme 8

Step A: 4,5-dimethylthiazole-2-carbaldehyde (2)

Under argon, to a solution of 4,5-dimethylthiazole (0.62 g, 5.5 mmol) in anhydrous THF (40 mL) at −78° C., n-butyllithium (2.3 M in hexanes, 3.6 mL, 8.28 mmol) was slowly added and the reaction mixture was stirred at −78° C. for 1 h. Then a solution of anhydrous DMF (1.1 mL, 14.2 mmol) in anhydrous THF (10 mL) was added. The resulting mixture was stirred for 2.5 hours, allowing the temperature to raise to −60° C. Acetic acid (0.5 mL) and an aqueous solution of ammonium chloride were added, and warmed to room temperature. The resulting solution was extracted with diethyl ether and ethyl acetate. The combined organic phase were dried over sodium sulfate, filtered and evaporated. The crude product was purified by flash chromatography (silica gel, PE/EA, 1/0 to 7/3) to afford 4,5-dimethyl-1,3-thiazole-2-carbaldehyde, as a yellow oil which turns into a white solid after storage at −18° C. LCMS m/z (M+H) 142.1 found, 142.1 required.

Step B: 4,5-dimethylthiazole-2-carbaldehyde oxime (3)

To a solution of 4,5-dimethylthiazole-2-carbaldehyde (987 mg, 7.0 mmol) in 1,4-dioxane (35 mL) was added hydroxylamine hydrochloride (1.45 g, 21 mmol) and $K_2CO_3$ (3.8 g, 28 mmol). The resulting mixture was stirred at 100° C. for 2 hours and then diluted with EtOAc (150 mL), washed with $H_2O$ (30 mL*2). The organic layer was dried over $Na_2SO_4$, filtered and concentrated to give the crude product which was used for next step without further purification. LCMS m/z (M+H) 157.1 found, 157.1 required.

Step C: (4,5-dimethylthiazol-2-yl)methanamine (4)

The crude 4,5-dimethylthiazole-2-carbaldehyde oxime (300 mg, 2 mmol) was dissolved in acetic acid (25 mL), zinc dust (1.8 g, 27.5 mmol) was added portionwise at room temperature and the reaction mixture was stirred at room temperature for 3 hours. The mixture was then filtered over a pad of celite and rinsed with methanol. Toluene was added and the filtrate was concentrated. An aqueous solution of $NH_4Cl$ was added, the solution was acidified to pH=2 with HCl (1N) and extracted with diethyl ether and ethyl acetate. The aqueous layer was basified with aqueous NaOH to pH=10, and then extracted with diethyl ether and ethyl acetate. Combined organic extracts were dried over sodium sulfate, filtered and evaporated to give crude (4,5-dimethyl-1,3-thiazol-2-yl)methylamine as a pale yellow oil which was used in the next step without purification. LCMS m/z (M+H) 143.1 found, 143.1 required.

Step D: 4-((4,5-dimethylthiazol-2-yl)methylamino)-6-(((1S,2S)-2-(5-methoxypyridin-2-yl)cyclopropyl)methoxy)-2-methylpyridazin-3(2H)-one (6)

A mixture of (4,5-dimethylthiazol-2-yl)methanamine (28 mg, 0.2 mmol), 4-bromo-6-(((1S,2S)-2-(5-methoxypyridin-2-yl)cyclopropyl)methoxy)-2-methylpyridazin-3(2H)-one (73 mg, 0.2 mmol), $Pd_2(dba)_3$ (18 mg, 0.02 mmol), BINAP (18 mg, 0.03 mmol) and $t$-BuONa (38 mg, 0.4 mmol) in toluene (4 mL) under $N_2$ was heated at 85° C. for 4 h. filtered and concentrated to give crude product which was purified by Pre-HPLC to give the title compound 6 as a oil. $^1$H NMR (400 MHz, $CD_3OD$) δ 7.92 (d, 1H), 7.14 (dd, 1H), 7.02 (d, 1H), 5.66 (s, 1H), 4.45 (d, 2H), 4.05-4.01 (m, 1H), 3.92-3.88 (m, 1H), 3.71 (s, 3H), 3.51 (s, 3H), 2.18 (s, 3H), 2.15 (s, 3H), 1.95-1.90 (m, 1H), 1.63-1.58 (m, 1H), 1.06-1.01 (m, 1H), 0.91-0.86 (m, 1H), LCMS m/z (M+H) 428.1 found, 428.1 required.

The following Examples 126-136 were prepared using the procedure of Example 126, substituting the appropriate starting materials.

TABLE 10

| Example | Structure | IUPAC Name | LCMS m/z [M + H] |
|---|---|---|---|
| 126 | 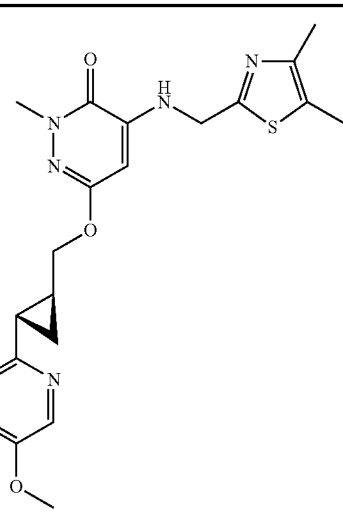 | 4-((4,5-dimethylthiazol-2-yl)methylamino)-6-(((1S,2S)-2-(5-methoxy-pyridin-2-yl)cyclopropyl-)methoxy)-2-methyl-pyridazin-3(2H)-one | 428.1 |

TABLE 10-continued
| Example | Structure | IUPAC Name | LCMS m/z [M + H] |
|---|---|---|---|
| 127 | 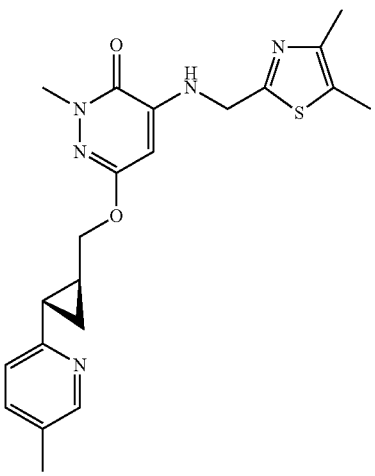 [SMILES: Cc1ccc([C@H]2C[C@@H]2COc2cc(NCc3nc(C)c(C)s3)c(=O)n(C)n2)nc1] | 4-((4,5-dimethylthiazol-2-yl)methylamino)-2-methyl-6-((((1S,2S)-2-(5-methyl-pyridin-2-yl)cyclopropyl)methoxy)pyridazin-3(2H)-one | 412.1 |
| 128 | 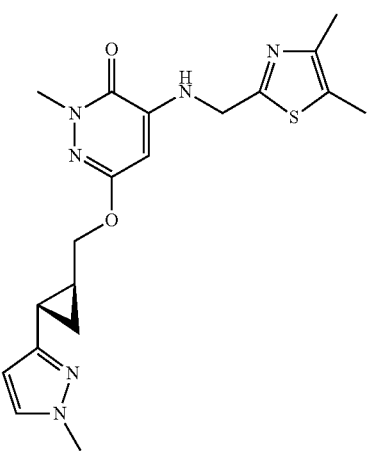 [SMILES: Cc1nc(CNc2cc(OC[C@H]3C[C@@H]3c3ccn(C)n3)nn(C)c2=O)sc1C] | 4-((4,5-dimethylthiazol-2-yl)methylamino)-2-methyl-6-((((1S,2S)-2-(1-methyl-1H-pyrazol-3-yl)cyclopropyl)methoxy)pyridazin-3(2H)-one | 401.1 |
| 129 | 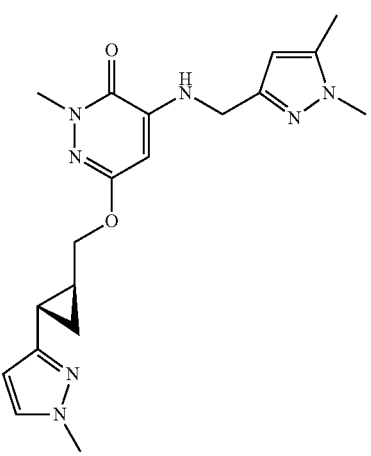 [SMILES: Cc1cc(CNc2cc(OC[C@H]3C[C@@H]3c3ccn(C)n3)nn(C)c2=O)nn1C] | 4-((1,5-dimethyl-1H-pyrazol-3-yl)methylamino)-2-methyl-6-((((1S,2S)-2-(1-methyl-1H-pyrazol-3-yl)cyclopropyl)methoxy)pyridazin-3(2H)-one | 384.2 |

TABLE 10-continued

| Example | Structure | IUPAC Name | LCMS m/z [M + H] |
|---|---|---|---|
| 130 | 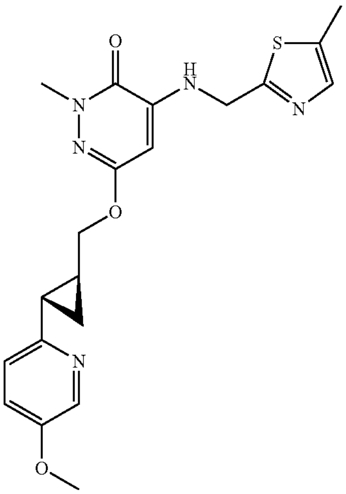 [SMILES: COc1ccc([C@H]2C[C@@H]2COc2cc(NCc3ncc(C)s3)c(=O)n(C)n2)nc1] | 6-(((1S,2S)-2-(5-methoxy-pyridin-2-yl)cyclopropyl-)methoxy)-2-methyl-4-((5-methyl-thiazol-2-yl)-methylamino-)pyridazin-3(2H)-one | 414.1 |
| 131 | 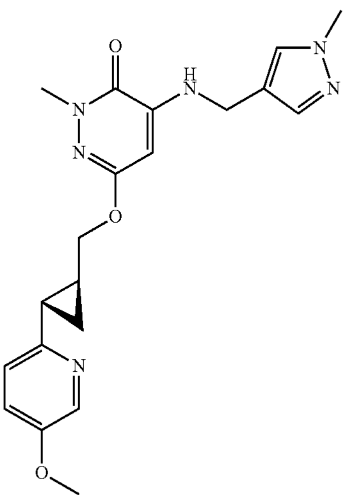 [SMILES: COc1ccc([C@H]2C[C@@H]2COc2cc(NCc3cnn(C)c3)c(=O)n(C)n2)nc1] | 6-(((1S,2S)-2-(5-methoxy-pyridin-2-yl)cyclopropyl-)methoxy)-2-methyl-4-((1-methyl-1H-pyrazol-4-yl)methylamino)pyridazin-3(2H)-one | 397.2 |
| 132 | 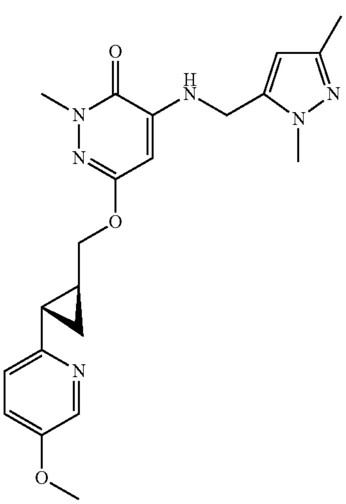 [SMILES: COc1ccc([C@H]2C[C@@H]2COc2cc(NCc3cc(C)nn3C)c(=O)n(C)n2)nc1] | 4-((1,3-dimethyl-1H-pyrazol-5-yl)methyl-amino)-6-(((1S,2S)-2-(5-methoxypyridin-2-yl)-cyclopropyl)methoxy)-2-methylpyridazin-3(2H)one | 411.1 |

TABLE 10-continued

| Example | Structure | IUPAC Name | LCMS m/z [M + H] |
|---|---|---|---|
| 133 | 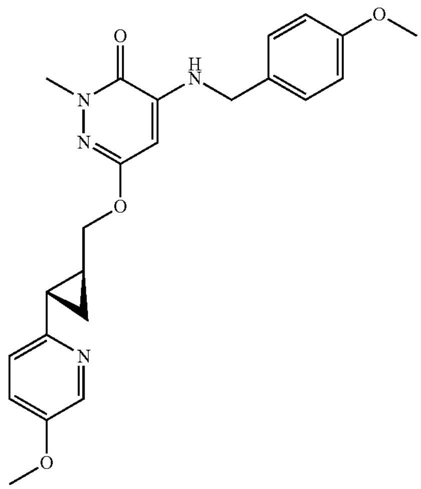 [SMILES: COc1ccc(CNc2cc(OC[C@H]3C[C@@H]3c3ccc(OC)cn3)nn(C)c2=O)cc1] | 4-(4-methoxybenzyl-amino)-6-(((1S,2S)-2-(5-methoxypyridin-2-yl)-cyclopropyl)methoxy)-2-methylpyridazin-3(2H)one | 423.2 |
| 134 | 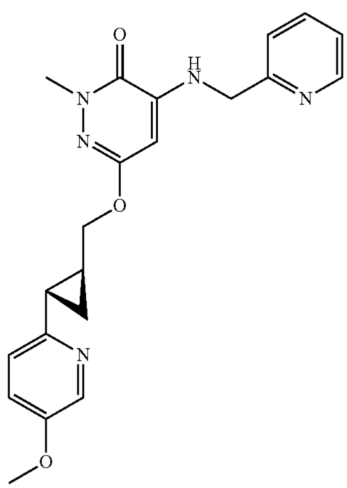 [SMILES: COc1ccc([C@H]2C[C@@H]2COc2cc(NCc3ccccn3)c(=O)n(C)n2)nc1] | 6-(((1S,2S)-2-(5-methoxy-pyridin-2-yl)-cyclopropyl-)methoxy)-2-methyl-4-(pyridin-2-yl-methyl-amino)pyridazin-3(2H)one | 394.2 |
| 135 | 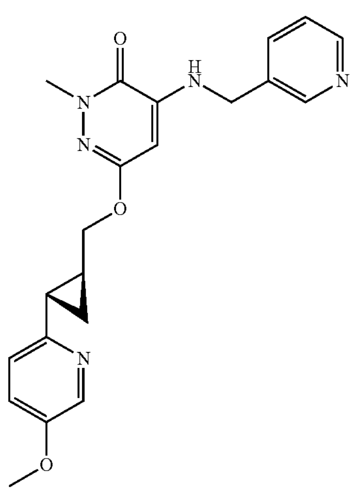 [SMILES: COc1ccc([C@H]2C[C@@H]2COc2cc(NCc3cccnc3)c(=O)n(C)n2)nc1] | 6-(((1S,2S)-2-(5-methoxy-pyridin-2-yl)cyclopropyl-)methoxy)-2-methyl-4-(pyridin-3-ylmethylamino-)pyridazin-3(2H)-one | 394.2 |

TABLE 10-continued
| Example | Structure | IUPAC Name | LCMS m/z [M + H] |
|---|---|---|---|
| 136 | 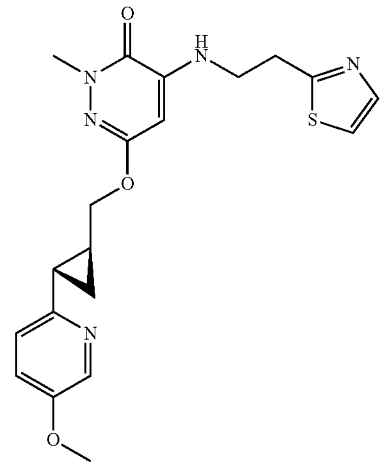 [SMILES: COc1ccc([C@H]2C[C@@H]2COc2cc(NCCc3nccs3)c(=O)n(C)n2)nc1] | 6-(((1S,2S)-2-(5-methoxy-pyridin-2-yl)cyclopropyl-)methoxy)-2-methyl-4-(2-(thiazol-2-yl)ethylamino-)pyridazin-3(2H)-one | 414.1 |
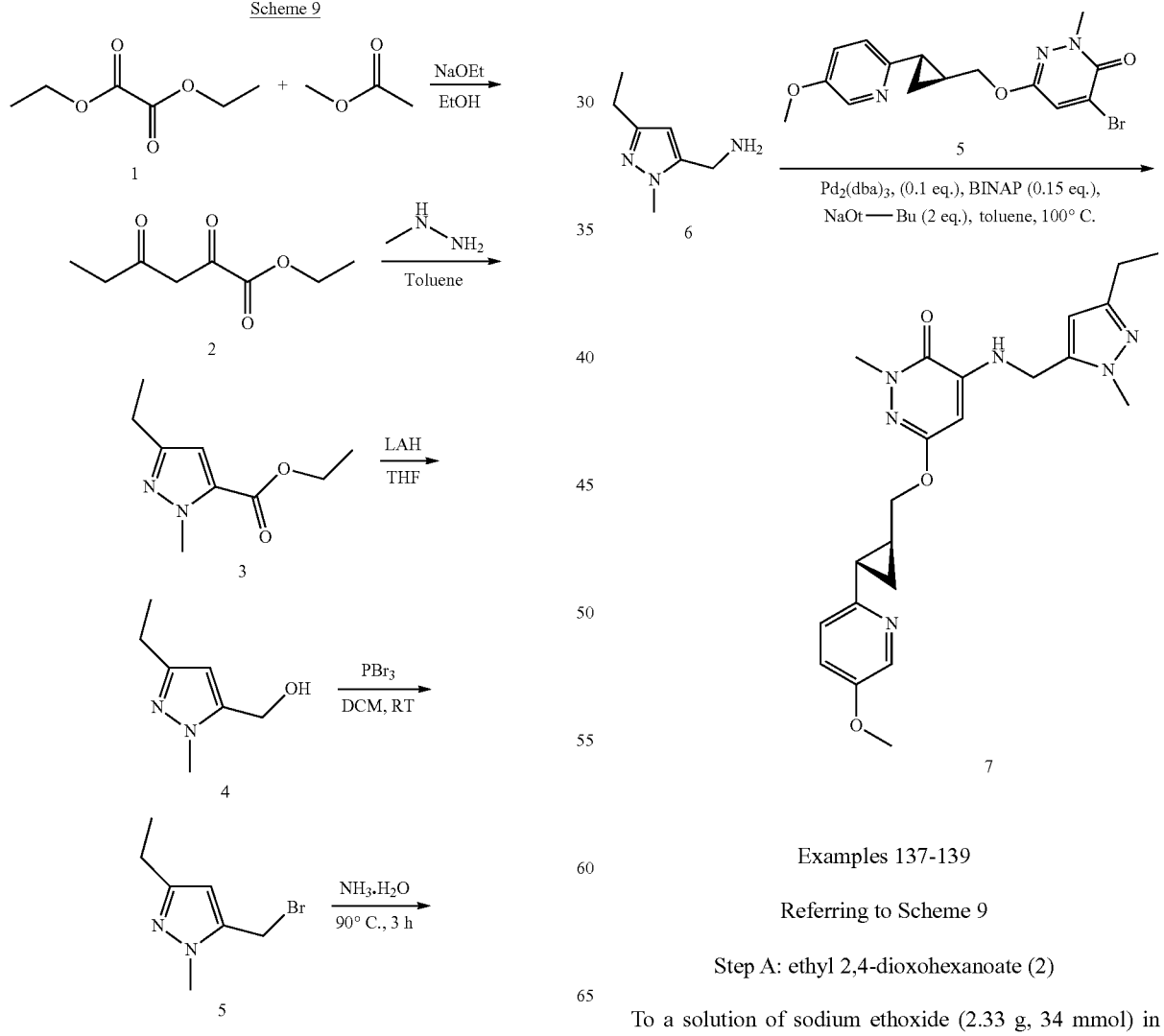
Examples 137-139
Referring to Scheme 9
Step A: ethyl 2,4-dioxohexanoate (2)
To a solution of sodium ethoxide (2.33 g, 34 mmol) in absolute alcohol (40 mL) was added a mixture of 2-butanone (2.45 g, 34 mmol) and diethyl oxalate (5 g, 34 mmol) dropwise at −5° C. The reaction mixture was stirred at −5° C. overnight and then concentrated. The resulting residue was partitioned between water (20 mL) and ethyl acetate (70 mL*3). The aqueous layer was acidified to pH 2 with dilute $H_2SO_4$ and then extracted with ethyl acetate (50 ml*3). The combined organic phase was dried over anhydrous $Na_2SO_4$, The organic solvent was evaporated in vacuo, and the residue was used directly in the next step without further purification.

Step B: ethyl 3-ethyl-1-methyl-1H-pyrazole-5-carboxylate (3)

To a solution of compound 2 (3.8 g, 22 mmol) in toluene (20 mL) was added methylhydrazine (1.8 g, 0.039 mol) cooled to −20° C. After completion of the reaction, the reaction liquid was washed with water and the solvent was removed by evaporation to obtain crude product, the crude product was purified by silica gel column chromatography (PE:EA=5:1) to give the desired product as a white oil.

Step C: (3-ethyl-1-methyl-1H-pyrazol-5-yl)methanol (4)

To a solution of compound 3 (2 g, 0.01 mol) in THF (20 mL) was added lithium aluminum hydride (0.63 g, 0.02 mol) at 0° C. and the mixture was stirred at room temperature for 30 min. Ethanol (10 mL) and saturated aqueous ammonium chloride solution (2.0 mL) were added to the reaction mixture. The precipitated insoluble material was filtered off, and the filtrate was concentrated under reduced pressure. The residue was subjected to silica gel chromatography (ethyl acetate:hexane=1:1) to give the title compound as a colorless oil.

Step D: 5-(bromomethyl)-3-ethyl-1-methyl-1H-pyrazole (5)

To a solution of compound 4 (500 mg, 3.57 mmol) in DCM (20 mL) was added $PBr_3$ (386 mg, 1.43 mmol) was stirred at ° C. for 2 h. The mixture was washed with water, dried over $Na_2SO_4$. The solvent was evaporated to give the crude compound which was used in the next step without further purification.

Step E: (3-ethyl-1-methyl-1H-pyrazol-5-yl)methanamine (6)

A solution of compound 5 (660 mg, 3.27 mmol) in $NH_3 \cdot H_2O$ (5 mL) was stirred at 90° C. for 3 h. The solvent was evaporated to give the crude product as a white solid which was used in the next step without further purification.

Step F: 4-((3-ethyl-1-methyl-1H-pyrazol-5-yl)methylamino)-6-(((1S,2S)-2-(5-methoxypyridin-2-yl)cyclopropyl)methoxy)-2-methylpyridazin-3(2H)-one (7)

To a solution of 4-bromo-6-(((1S,2S)-2-(5-methoxypyridin-2-yl)cyclopropyl)methoxy)-2-methylpyridazin-3(2H)-one (70 mg, 0.19 mmol) in toluene (5 mL) under $N_2$, ((3-ethyl-1-methyl-1H-pyrazol-5-yl)methanamine (32.2 mg, 0.23 mmol), $Pd_2(dba)_3$ (18 mg, 0.019 mmol), BINAP (35 mg, 0.06 mmol) and $NaO^tBu$ (27 mg, 0.285 mmol) were added. After the reaction mixture was stirred at 100° C. overnight, 15 mL water was added. The mixture was extracted with EtOAc (2×10 mL). The combined organics were dried over $MgSO_4$, filtered and concentrated in vacuo. The residue was purified by Prep-HPLC to give the title compound as oil. $^1$H NMR (400 MHz, $CDCl_3$) δ 8.43 (s, 1H), 7.73 (d, 1H), 7.21 (d, 1H), 6.14 (s, 1H), 5.75 (s, 1H), 4.45-4.28 (m, 3H), 4.00 (d, 4H), 3.89 (s, 3H), 3.67 (s, 3H), 2.66 (d, 2H), 2.53 (s, 1H), 1.88 (s, 1H), 1.41 (s, 2H), 1.22 (t, 3H).

The following Examples 137-139 were prepared using the procedure of Example 137, substituting the appropriate starting materials.

TABLE 11

| Example | Structure | IUPAC Name | LCMS m/z [M + H]+ |
|---|---|---|---|
| 137 | 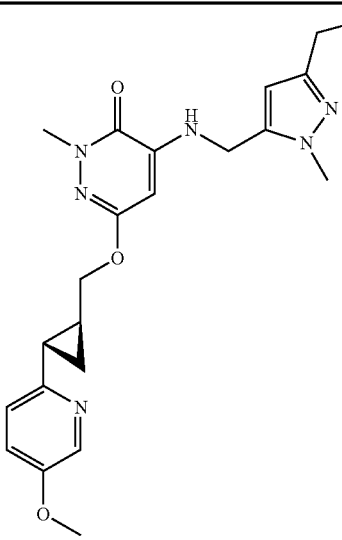 | 4-((3-ethyl-1-methyl-1H-pyrazol-5-yl)methylamino)-6-(((1S,2S)-2-(5-methoxypyridin-2-yl)cyclopropyl)methoxy)-2-methylpyridazin-3(2H)-one | 425.2 |

TABLE 11-continued
| Example | Structure | IUPAC Name | LCMS m/z [M + H]+ |
|---------|-----------|------------|-------------------|
| 138 | 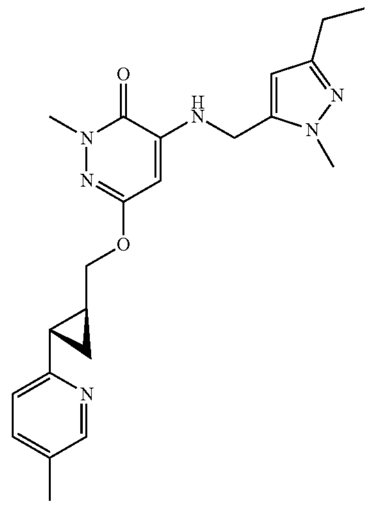 [SMILES: CCc1cc(CNc2cc(OC[C@H]3C[C@@H]3c3ccc(C)cn3)nn(C)c2=O)n(C)n1] | 4-((3-ethyl-1-methyl-1H-pyrazol-5-yl)methylamino)-2-methyl-6-((((1S,2S)-2-(5-methylpyridin-2-yl)cyclopropyl)methoxy)pyridazin-3(2H)-one | 409.2 |
| 139 | 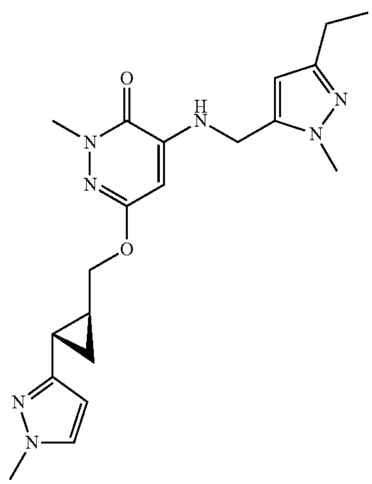 [SMILES: CCc1cc(CNc2cc(OC[C@H]3C[C@@H]3c3ccn(C)n3)nn(C)c2=O)n(C)n1] | 4-((3-ethyl-1-methyl-1H-pyrazol-5-yl)methylamino)-2-methyl-6-((((1S,2S)-2-(1-methyl-1H-pyrazol-3-yl)cyclopropyl)methoxy)pyridazin-3(2H)-one | 398.2 |
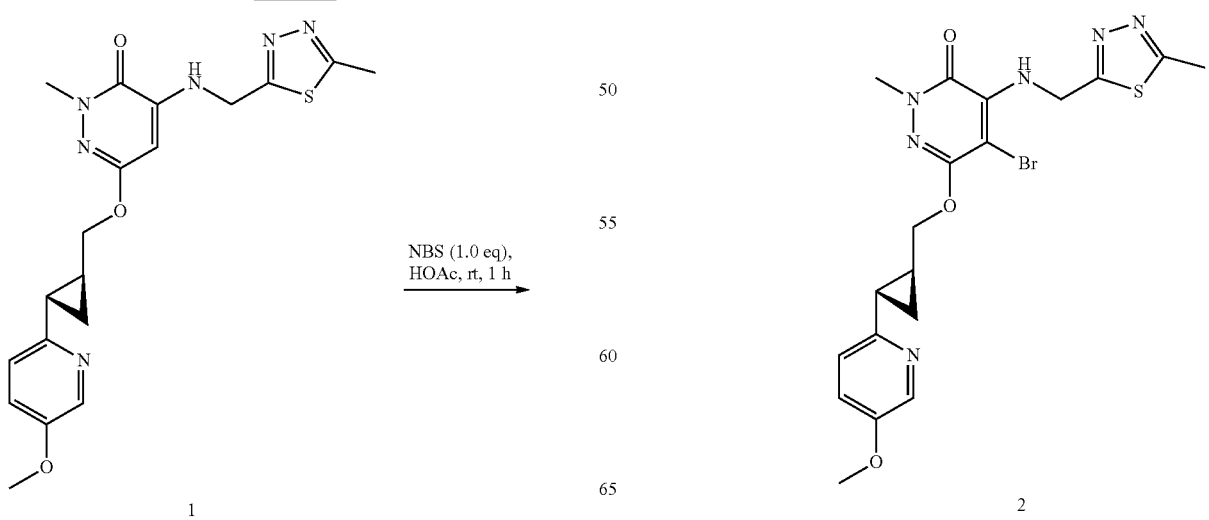
Scheme 10

Examples 140-141

Referring to Scheme 10

Step A: 5-bromo-6-(((1S,2S)-2-(5-methoxypyridin-2-yl)cyclopropyl)methoxy)-2-methyl-4-((5-methyl-1,3,4-thiadiazol-2-yl)methylamino)pyridazin-3(2H)-one (2)

To a solution of compound 1 (95 mg, 0.23 mmol) in HOAc (5 mL) was added NBS (41 mg, 0.23 mmol). After stirred at room temperature for 1 h, the reaction mixture was adjusted pH to 7-8 with saturated NaHCO$_3$ solution and extracted with EtOAc (20 mL*2). The organic phase was washed with H$_2$O (20 mL) and brine (20 mL), dried over Na$_2$SO$_4$ and concentrated. The residue was purified by Prep-HPLC to give compound 2 as a TFA salt. ESI-MS: 493.1 (M+H)$^+$. $^1$H NMR (400 MHz, MeOD) δ 8.28 (s, 1H), 7.95 (d, 1H), 7.56 (d, 1H), 5.34 (s, 2H), 4.34 (dd, 1H), 4.19 (dd, 1H), 3.98 (s, 3H), 3.61 (s, 3H), 2.76 (s, 3H), 2.37-2.35 (m, 1H), 1.99-1.97 (m, 1H), 1.46-1.41 (m, 2H).

The following Examples 140-141 were prepared using the procedure of Example 140, substituting the appropriate starting materials.

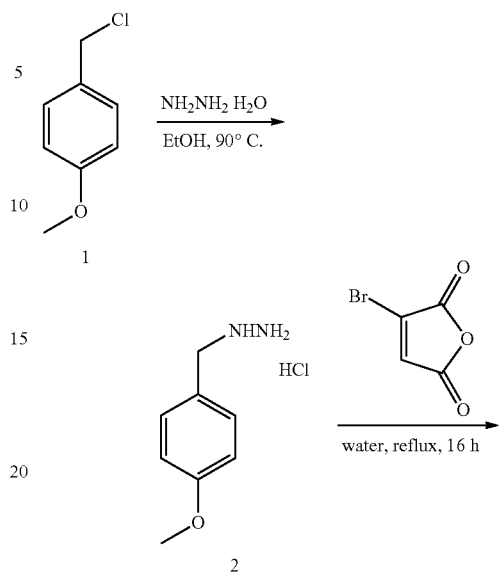

Scheme 11

TABLE 12

| Example | Structure | IUPAC Name | LCMS m/z [M + H]$^+$ |
|---|---|---|---|
| 140 | 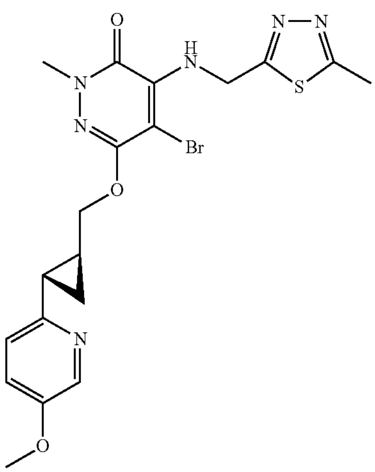 [SMILES: COc1ccc([C@H]2C[C@@H]2COc2nn(C)c(=O)c(NCc3nnc(C)s3)c2Br)nc1] | 5-bromo-6-(((1S,2S)-2-(5-methoxypyridin-2-yl)cyclopropyl)methoxy)-2-methyl-4-((5-methyl-1,3,4-thiadiazol-2-yl)methylamino)pyridazin-3(2H)-one | 493.1 |
| 141 | 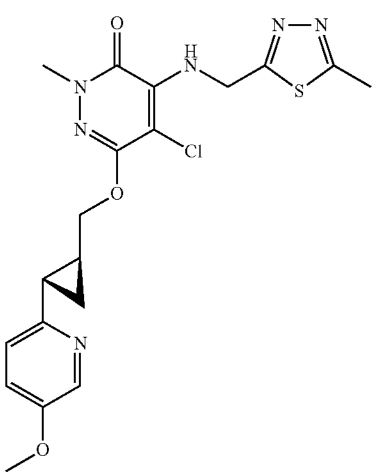 [SMILES: COc1ccc([C@H]2C[C@@H]2COc2nn(C)c(=O)c(NCc3nnc(C)s3)c2Cl)nc1] | 5-chloro-6-(((1S,2S)-2-(5-methoxypyridin-2-yl)cyclopropyl)methoxy)-2-methyl-4-((5-methyl-1,3,4-thiadiazol-2-yl)methylamino)pyridazin-3(2H)-one | 449.1 |

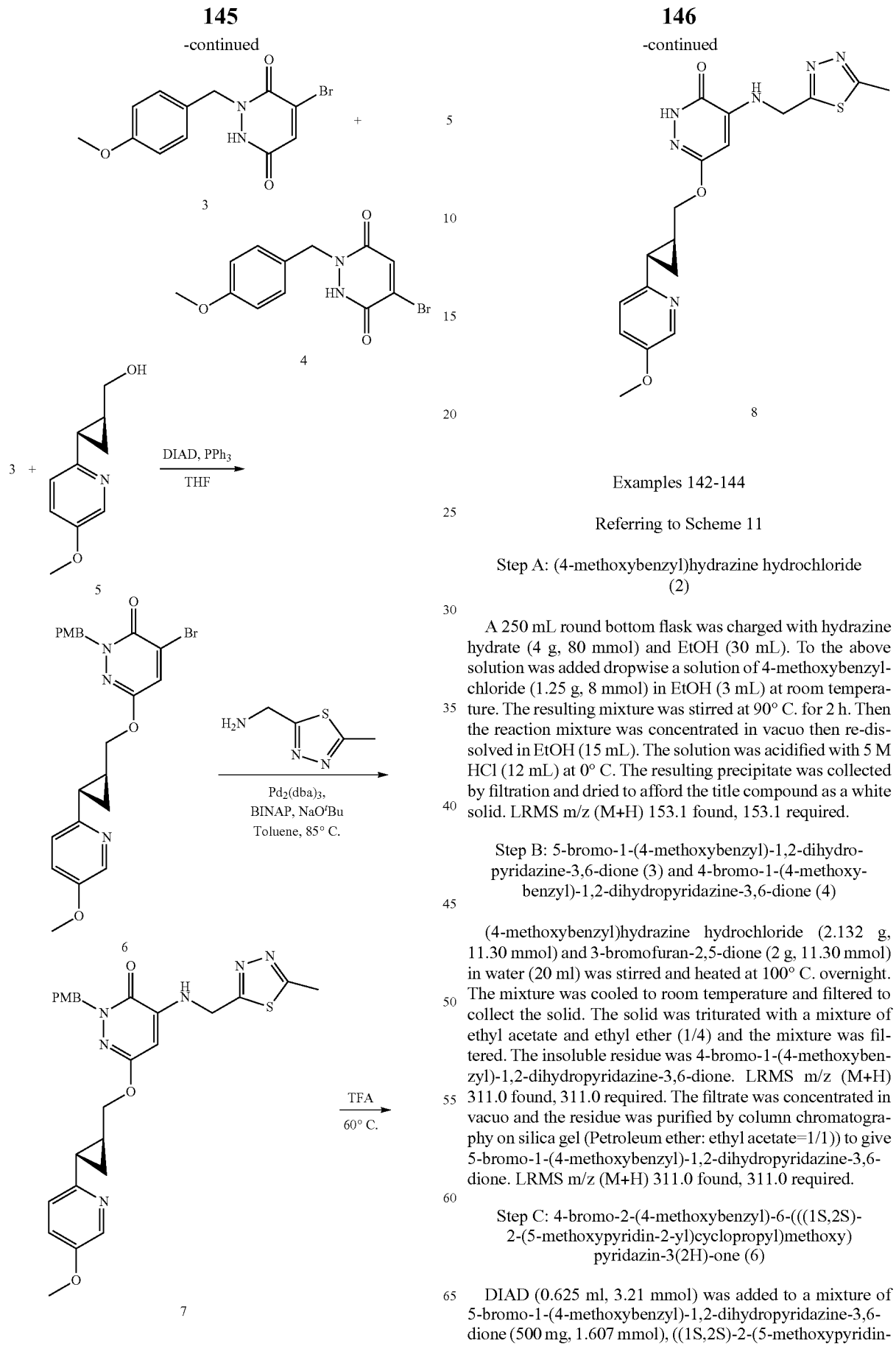

Examples 142-144

Referring to Scheme 11

Step A: (4-methoxybenzyl)hydrazine hydrochloride (2)

A 250 mL round bottom flask was charged with hydrazine hydrate (4 g, 80 mmol) and EtOH (30 mL). To the above solution was added dropwise a solution of 4-methoxybenzyl-chloride (1.25 g, 8 mmol) in EtOH (3 mL) at room temperature. The resulting mixture was stirred at 90° C. for 2 h. Then the reaction mixture was concentrated in vacuo then re-dissolved in EtOH (15 mL). The solution was acidified with 5 M HCl (12 mL) at 0° C. The resulting precipitate was collected by filtration and dried to afford the title compound as a white solid. LRMS m/z (M+H) 153.1 found, 153.1 required.

Step B: 5-bromo-1-(4-methoxybenzyl)-1,2-dihydro-pyridazine-3,6-dione (3) and 4-bromo-1-(4-methoxy-benzyl)-1,2-dihydropyridazine-3,6-dione (4)

(4-methoxybenzyl)hydrazine hydrochloride (2.132 g, 11.30 mmol) and 3-bromofuran-2,5-dione (2 g, 11.30 mmol) in water (20 ml) was stirred and heated at 100° C. overnight. The mixture was cooled to room temperature and filtered to collect the solid. The solid was triturated with a mixture of ethyl acetate and ethyl ether (1/4) and the mixture was filtered. The insoluble residue was 4-bromo-1-(4-methoxyben-zyl)-1,2-dihydropyridazine-3,6-dione. LRMS m/z (M+H) 311.0 found, 311.0 required. The filtrate was concentrated in vacuo and the residue was purified by column chromatography on silica gel (Petroleum ether: ethyl acetate=1/1)) to give 5-bromo-1-(4-methoxybenzyl)-1,2-dihydropyridazine-3,6-dione. LRMS m/z (M+H) 311.0 found, 311.0 required.

Step C: 4-bromo-2-(4-methoxybenzyl)-6-(((1S,2S)-2-(5-methoxypyridin-2-yl)cyclopropyl)methoxy)pyridazin-3(2H)-one (6)

DIAD (0.625 ml, 3.21 mmol) was added to a mixture of 5-bromo-1-(4-methoxybenzyl)-1,2-dihydropyridazine-3,6-dione (500 mg, 1.607 mmol), (((1S,2S)-2-(5-methoxypyridin- 2-yl)cyclopropyl)methanol (288 mg, 1.607 mmol) and PPh$_3$ (843 mg, 3.21 mmol) in THF (15 ml) at 0° C.

The mixture was stirred at room temperature for 1 h. The mixture was concentrated and purified by Prep-TLC (Petroleum ether: ethyl acetate=1:1) afforded title product. LRMS m/z (M+H) 471.1 found, 471.0 required.

Step D: 2-(4-methoxybenzyl)-6-(((1S,2S)-2-(5-methoxypyridin-2-yl)cyclopropyl)methoxy)-4-((5-methyl-1,3,4-thiadiazol-2-yl)methylamino)pyridazin-3(2H)-one (7)

A 25 mL vial was charged with 4-bromo-2-(4-methoxybenzyl)-6-(((1S,2S)-2-(5-methoxypyridin-2-yl)cyclopropyl)methoxy)pyridazin-3(2H)-one (112 mg, 0.237 mmol), (5-methyl-1,3,4-thiadiazol-2-yl)methanamine hydrochloride (43.2 mg, 0.261 mmol), Pd$_2$(dba)$_3$ (21.71 mg, 0.024 mmol), BINAP (22.15 (22.15 mg, 0.036 mmol) and NaO$^t$—Bu (57.0 mg, 0.593 mmol) in Toluene (4 ml). The reaction was purged with nitrogen and stirred at 85° C. for 4 h. Then the mixture was concentrated under vacuum to give a residue, which was purified by Prep-TLC (ethyl acetate, 100%) to afford 2-(4-methoxybenzyl)-6-(((1S,2S)-(((1S,2S)-2-(5-methoxypyridin-2-yl)cyclopropyl)methoxy)-4-(((5-methyl-1,3,4-thiadiazol-2-yl)methyl)amino)pyridazin-3(2H)-one LRMS m/z (M+H) 521.3 found, 521.3 required. $^1$H NMR (400 MHz, DMSO) δ 8.12 (d, 1H), 7.59 (t, 1H), 7.25 (dd, 3H), 7.18 (d, 1H), 6.86 (d, 2H), 5.87 (d 1H), 5.00 (s, 2H), 4.72 (d, 2H), 4.05 (m, 1H), 3.97 (m, 1H), 3.77 (s, 3H), 3.71 (s, 3H), 2.65 (s, 3H), 2.12 (m, 1H), 1.66 (m, 1H), 1.06 (m, 1H), 0.99 (m, 1H).

Step E: 6-((((1S,2S)-2-(5-methoxypyridin-2-yl)cyclopropyl)methoxy)-4-((5-methyl-1,3,4-thiadiazol-2-yl)methylamino)pyridazin-3(2H)-one (8)

2-(4-methoxybenzyl)-6-(((1S,2S)-2-(5-methoxypyridin-2-yl)cyclopropyl)methoxy)-4-(((5-methyl-1,3,4-thiadiazol-2-yl)methyl)amino)pyridazin-3(2H)-one (50 mg, 0.096 mmol) was dissolved in TFA (2 ml) and heated at 60° C. for 24 h. The mixture was cooled and the solvent was evaporated under reduced pressure. The crude was purified by Prep-HPLC to afford title product. LRMS m/z (M+H) 401.1 found, 401.1 required. $^1$H NMR (400 MHz, MeOD) δ 8.06 (d, 1H), 7.30 (dd, 1H), 7.17 (d, 1H), 5.94 (s, 1H), 4.81 (s, 2H), 4.15 (dd, 1H), 4.04 (dd, 1H), 3.85 (s, 3H), 2.75 (s, 3H), 2.11 (m, 1H), 1.72 (m, 1H), 1.21 (m, 1H), 1.07 (m, 1H).

The following Examples 142-144 were prepared using the procedure of Example 142, substituting the appropriate starting materials.

TABLE 13

| Example | Structure | IUPAC Name | LCMS m/z [M + H]$^+$ |
|---|---|---|---|
| 142 | 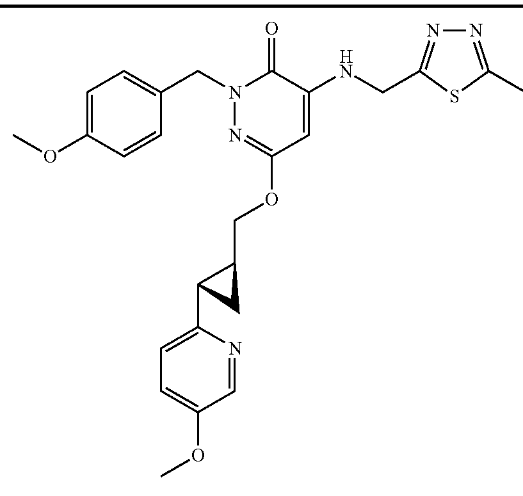 | 2-(4-methoxybenzyl)-6-(((1S,2S)-2-(5-methoxy-pyridin-2-yl)cyclopropyl-)methoxy)-4-((5-methyl-1,3,4-thiadiazol-2-yl)methyl-amino)pyridazin-3(2H)-one | 521.3 |
| 143 | 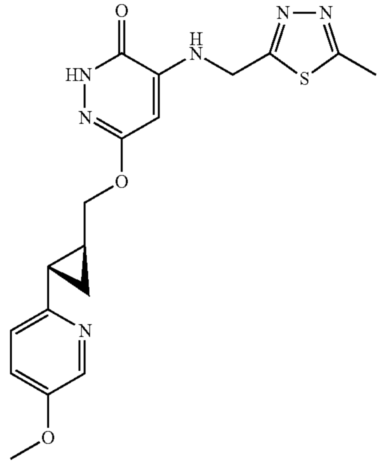 [SMILES: COc1ccc([C@H]2C[C@@H]2COc2cc(NCc3nnc(C)s3)c(=O)[nH]n2)nc1] | 6-(((1S,2S)-2-(5-methoxypyridin-2-yl)cyclopropyl)methoxy)-4-((5-methyl-1,3,4-thiadiazol-2-yl)methylamino)pyridazin-3(2H)-one | 401.1 |

TABLE 13-continued
| Example | Structure | IUPAC Name | LCMS m/z [M + H]+ |
|---|---|---|---|
| 144 | 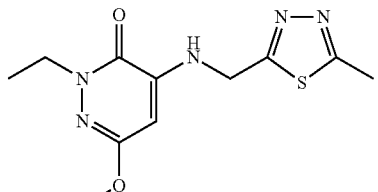 | 2-ethyl-6-(((1S,2S)-2-(5-methoxypyridin-2-yl)cyclopropyl)methoxy)-4-((5-methyl-1,3,4-thiadiazol-2-yl)methylamino)pyridazin-3(2H)-one | 429.1 |
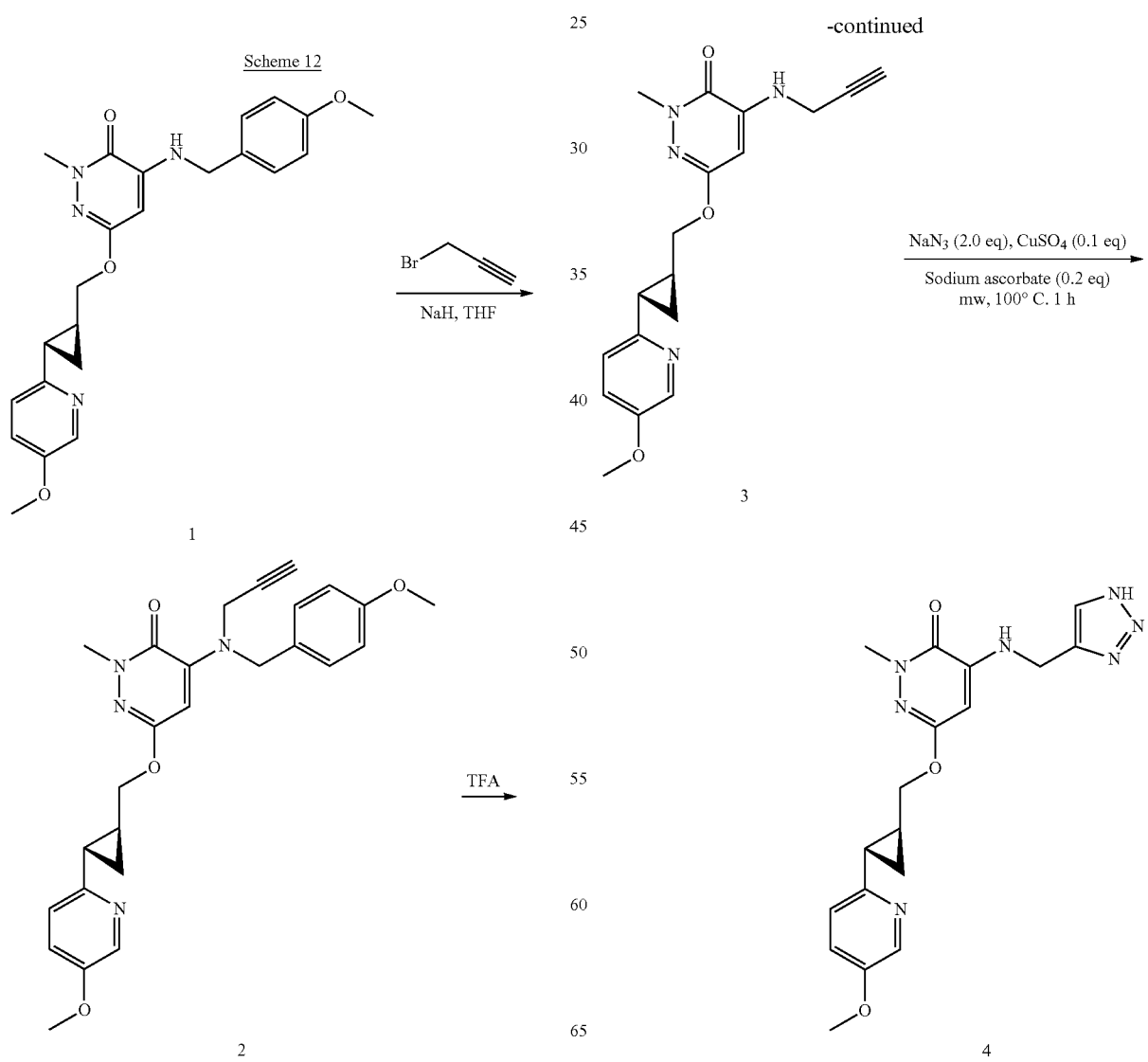

Examples 145-146

Referring to Scheme 12

Step A: 4-((4-methoxybenzyl)(prop-2-ynyl)amino)-6-(((1S,2S)-2-(5-methoxypyridin-2-yl)cyclopropyl)methoxy)-2-methylpyridazin-3(2H)-one (2)

To a solution of 4-(4-methoxybenzylamino)-6-(((1S,2S)-2-(5-methoxypyridin-2-yl)cyclopropyl)methoxy)-2-methylpyridazin-3(2H)-one (210 mg, 0.50 mmol) in THF (20 mL) was added NaH (30 mg, 0.75 mmol) at 0° C. After stirred for 10 min, 3-bromoprop-1-yne (118 mg, 1.00 mmol) was added. The mixture was stirred for 2 h at room temperature and then diluted with H$_2$O (20 mL) and EtOAc (50 mL). The organic phase was washed with H2O and brine, dried over Na$_2$SO$_4$, filtered and concentrated. The residue was purified by column chromatography on silica gel, eluting with PE/EA (4/1) to give the title compound as oil. ESI-MS: 461.2 (M+H)$^+$. $^1$H NMR (400 MHz, MeOD) δ 7.95 (d, 1H), 7.21-7.18 (m, 3H), 7.07 (d, 1H), 6.78 (d, 2H), 6.19 (s, 1H), 4.50 (s, 2H), 4.10-3.94 (m, 4H), 3.75 (s, 3H), 3.74 (s, 3H), 3.72 (s, 3H), 2.61 (s, 1H), 2.00-1.96 (m, 1H), 1.68-1.63 (m, 1H), 1.11-1.00 (m, 1H), 0.95-0.97 (m, 1H).

Step B: 6-(((1S,2S)-2-(5-methoxypyridin-2-yl)cyclopropyl)methoxy)-2-methyl-4-(prop-2-ynylamino)pyridazin-3(2H)-one (3)

A solution of compound 2 (180 mg, 0.39 mmol) in TFA (5 mL) was stirred at room temperature for 2 h, then pH was adjusted to 7-8 with saturated NaHCO$_3$ solution. Extracted with EtOAc (20 mL*3) and washed with H$_2$O and brine, the organic phase was concentrated to give the title compound. ESI-MS: 341.2 (M+H)$^+$.

Step C: 4-((1H-1,2,3-triazol-4-yl)methylamino)-6-(((1S,2S)-2-(5-methoxypyridin-2-yl)cyclopropyl)methoxy)-2-methylpyridazin-3(2H)-one (4)

A mixture of compound 3 (110 mg, 0.32 mmol), NaN$_3$ (42 mg, 0.64 mmol), CuSO$_4$ (6 mg, 0.03 mmol) and sodium ascorbate (12 mg, 0.06 mmol) in DMA (2 mL) was purged with nitrogen for 1 min, which was heated to 100° C. in microwave reactor for 1 h, then the mixture was diluted with water (10 mL), extracted with EtOAc (15×3 mL), dried over Na$_2$SO$_4$ and concentrated. The residue was purified by Prep-HPLC (CH$_3$CN in 0.05% TFA/H$_2$O 30-95% v/v as mobile phase) to give title compound as a TFA salt. ESI-MS: 384.2 (M+H)$^+$. $^1$H NMR (400 MHz, MeOD) δ 8.33 (s, 1H), 8.00 (dd, 1H), 7.79 (s, 1H), 7.59 (d, 1H), 5.88 (s, 1H), 4.50 (s, 2H), 4.30 (dd, 1H), 4.11 (dd, 1H), 3.98 (s, 3H), 3.63 (s, 3H), 2.36-2.32 (m, 1H), 2.03-1.97 (m, 1H), 1.41-1.41 (m, 2H).

TABLE 14

| Example | Structure | IUPAC Name | LCMS m/z [M + H]$^+$ |
|---|---|---|---|
| 145 | 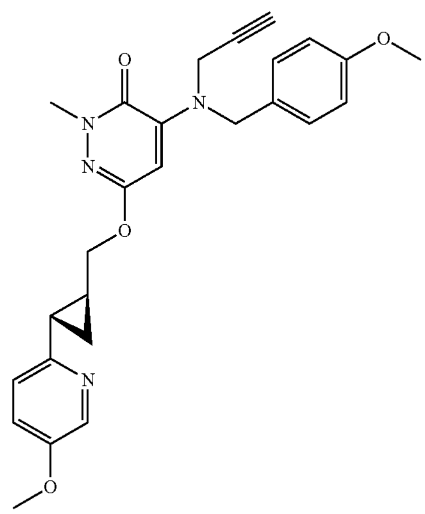 [SMILES: C#CCN(Cc1ccc(OC)cc1)c1cc(OC[C@H]2C[C@@H]2c2ccc(OC)cn2)nn(C)c1=O] | 4-((4-methoxybenzyl)(prop-2-ynyl)amino)-6-(((1S,2S)-2-(5-methoxypyridin-2-yl)cyclopropyl)methoxy)-2-methylpyridazin-3(2H)-one | 461.20 |
| 146 | 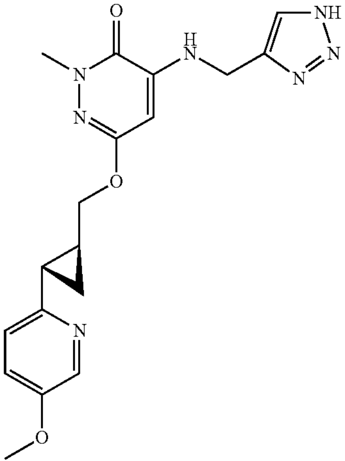 [SMILES: COc1ccc([C@H]2C[C@@H]2COc2cc(NCc3c[nH]nn3)c(=O)n(C)n2)nc1] | 4-((1H-1,2,3-triazol-4-yl)methylamino)-6-(((1S,2S)-2-(5-methoxypyridin-2-yl)cyclopropyl)methoxy)-2-methylpyridazin-3(2H)-one | 384.2 |

Scheme 13
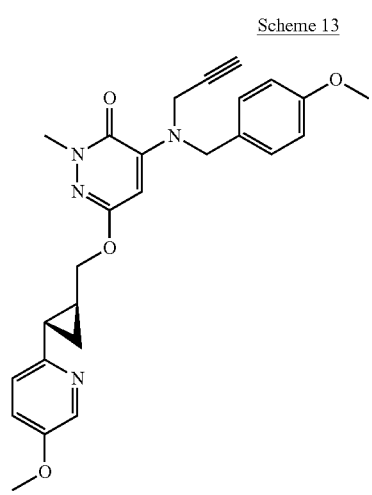
1
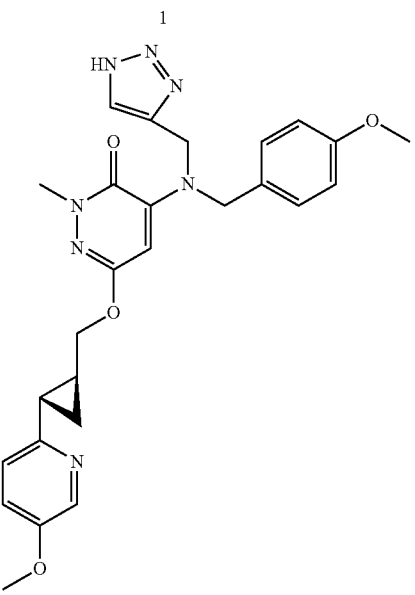
2
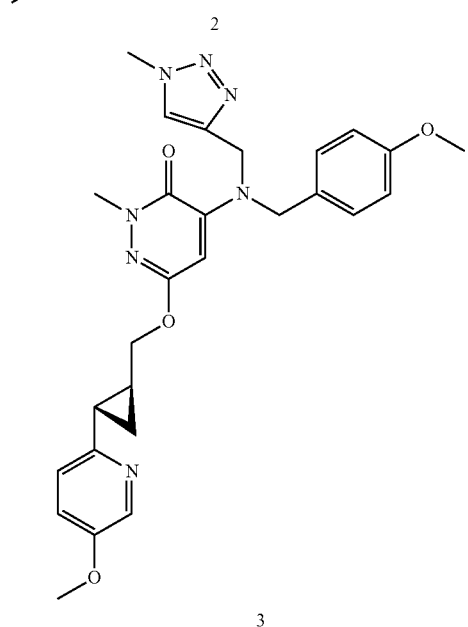
3
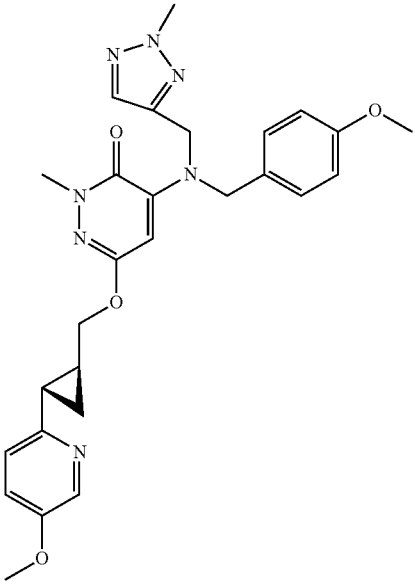
4
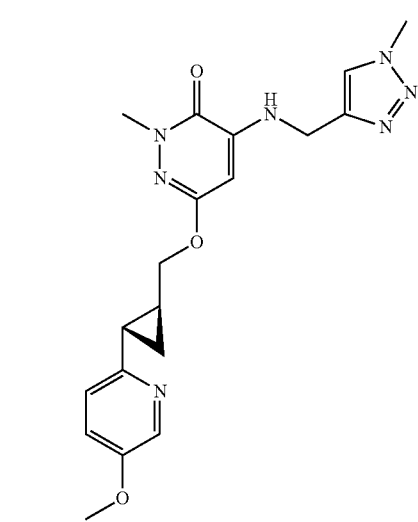
5
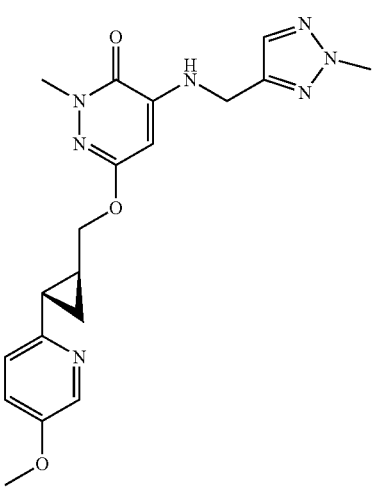
6

Examples 147-148

Referring to Scheme 13

Step A: 4-((((1H-1,2,3-triazol-4-yl)methyl)(4-methoxybenzyl)amino)-6-(((1S,2S)-2-(5-methoxypyridin-2-yl)cyclopropyl)methoxy)-2-methylpyridazin-3(2H)-one (2)

A mixture of compound 1 (180 mg, 0.39 mmol), NaN₃ (51 mg, 0.78 mmol), CuSO₄ (6 mg, 0.04 mmol) and sodium ascorbate (12 mg, 0.06 mmol) in DMA (2 mL) was purged with nitrogen for 1 min, which was heated to 100° C. in microwave reactor for 1 h, then the mixture was diluted residue was purified by prep-TLC using PE/EtOAc=3/1 to give title compound as a yellow solid. ESI-MS: 504.2 (M+H)⁺.

Step B: 4-((4-methoxybenzyl)((1-methyl-1H-1,2,3-triazol-4-yl)methyl)amino)-6-(((1S,2S)-2-(5-methoxypyridin-2-yl)cyclopropyl)methoxy)-2-methylpyridazin-3(2H)-one (3) and 4-((4-methoxybenzyl)((2-methyl-2H-1,2,3-triazol-4-yl)methyl)amino)-6-(((1S,2S)-2-(5-methoxypyridin-2-yl)cyclopropyl)methoxy)-2-methylpyridazin-3(2H-one (4)

To a solution of compound 2 (100 mg, 0.20 mmol) in THF (20 mL) was added NaH (12 mg, 0.30 mmol) at 0° C. After stirred for 10 min, MeI (57 mg, 0.40 mmol) was added. The mixture was stirred for 2 h at room temperature and then diluted with H₂O (20 mL) and EtOAc (50 mL). The organic phase was washed with H₂O and brine, dried over Na2SO4, filtered and concentrated. The residue was purified by prep-TLC using PE/EtOAc=4/1 to give 4-((4-methoxybenzyl)((1-methyl-1H-1,2,3-triazol-4-yl)methyl)amino)-6-(((1S,2S)-2-(5-methoxypyridin-2-yl)cyclopropyl)methoxy)-2-methylpyridazin-3(2H)-one (3) (55 mg, yield: 53%) as a yellow solid and 4-((4-methoxybenzyl)((2-methyl-2H-1,2,3-triazol-4-yl)methyl)amino)-6-(((1S,2S)-2-(5-methoxypyridin-2-yl)cyclopropyl)methoxy)-2-methylpyridazin-3(2H)-one (4). ESI-MS: 461.2 (M+H)⁺.

Step C: 6-(((1S,2S)-2-(5-methoxypyridin-2-yl)cyclopropyl)methoxy)-2-methyl-4-((1-methyl-1H-1,2,3-triazol-4-yl)methylamino)pyridazin-3(2H)-one (5)

A solution of 4-((4-methoxybenzyl)((1-methyl-1H-1,2,3-triazol-4-yl)methyl)amino)-6-(((1S,2S)-2-(5-methoxypyridin-2-yl)cyclopropyl)methoxy)-2-methylpyridazin-3(2H)-one (55 mg, 0.11 mmol) in TFA (2 mL) was stirred at room temperature for 2 h, then pH was adjusted to 7~8 with saturated NaHCO₃ solution. Extracted with EtOAc (20 mL*3), washed with H₂O and brine, and concentrated. The residue was purified by Prep-HPLC (CH₃CN in 0.05% TFA/H₂O 30-95% v/v as mobile phase) to give title compound as a TFA salt, the structure was confirmed by NOE. ESI-MS: 398.2 (M+H)⁺. ¹H NMR (400 MHz, MeOD) δ 8.34 (d, 1H), 8.03 (dd, 1H), 7.86 (s, 1H), 7.80 (d, 1H), 5.88 (s, 1H), 4.47 (s, 2H), 4.30 (dd, 1H), 4.11 (dd, 1H), 4.06 (s, 3H), 4.01 (s, 3H), 3.62 (s, 3H), 2.36-2.32 (m, 1H), 2.01-1.96 (m, 1H), 1.41-1.41 (m, 2H).

TABLE 15

| Example | Structure | IUPAC Name | LCMS m/z [M + H]⁺ |
|---|---|---|---|
| 147 | (structure) | 6-(((1S,2S)-2-(5-methoxy-pyridin-2-yl)-cyclopropyl-)methoxy)-2-methyl-4-((1-methyl-1H-1,2,3-triazol-4-yl)methylamino)pyridazin-3(2H)-one | 398.2 |

TABLE 15-continued

| Example | Structure | IUPAC Name | LCMS m/z [M + H]+ |
|---|---|---|---|
| 148 | 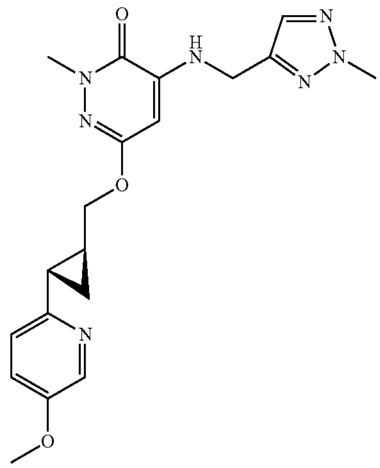 [SMILES: COc1ccc([C@H]2C[C@@H]2COc2cc(NCc3cnn(C)n3)c(=O)n(C)n2)nc1] | 6-(((1S,2S)-2-(5-methoxypyridin-2-yl)cyclopropyl)methoxy)-2-methyl-4-((2-methyl-2H-1,2,3-triazol-4-yl)methylamino)pyridazin-3(2H)-one | 398.2 |

The compounds of the following examples had activity in inhibiting the human PDE10 enzyme in the aforementioned assays with an Ki of about 0.001 nM to about 100 nM as indicated in Table 10 below.

The following table 16 shows representative data for the compounds of the Examples as PDE10 inhibitors as determined by the foregoing assays wherein the PDE10 Ki is a measure of the ability of the test compound to inhibit the action of the PDE10 enzyme. Representative compounds of the invention had the Ki values specified in parentheses immediately following the compound number in the above-described assay.

TABLE 16

| Compound/example | PDE10A Ki (nM) | Compound/example | PDE10A Ki (nM) |
|---|---|---|---|
| 1 | 0.013 | 21 | 0.044 |
| 2 | 0.089 | 22 | 0.175 |
| 3 | 0.001 | 23 | 0.478 |
| 4 | 0.015 | 24 | 0.473 |
| 5 | 0.157 | 25 | 0.0819 |
| 6 | 0.100 | 26 | 0.097 |
| 7 | 0.535 | 27 | 0.34 |
| 8 | 0.074 | 28 | 0.046 |
| 9 | 0.051 | 29 | 0.109 |
| 10 | 0.072 | 30 | 0.552 |
| 11 | 0.121 | 31 | 0.007 |
| 12 | 9.89 | 32 | 0.176 |
| 13 | 0.011 | 33 | 0.020 |
| 14 | 0.003 | 34 | 0.064 |
| 15 | 1.287 | 35 | 0.476 |
| 16 | 0.782 | 36 | 0.911 |
| 17 | 0.502 | 37 | 0.009 |
| 18 | 0.099 | 38 | 1.53 |
| 19 | 1.261 | 39 | 1.58 |
| 20 | 0.806 | 40 | 11.76 |
| 41 | | 73 | 32.3 |
| 42 | | 74 | 5.3 |
| 43 | | 75 | 1.3 |
| 44 | | 76 | 0.039 |
| 45 | | 77 | 5.7 |
| 46 | | 78 | |
| 47 | 8.21 | 79 | 1.1 |
| 48 | >100 | 80 | |
| 49 | 16.6 | 81 | |
| 50 | 0.003 | 82 | 75 |
| 51 | 0.023 | 83 | 42.6 |
| 52 | 0.007 | 84 | |
| 53 | 0.034 | 85 | |
| 54 | 0.019 | 86 | 9.4 |
| 55 | 0.021 | 87 | 0.01 |
| 56 | 0.002 | 88 | 2.8 |
| 57 | 0.004 | 89 | 0.008 |
| 58 | 0.028 | 90 | |
| 59 | 0.38 | 91 | 5.9 |
| 60 | | 92 | |
| 61 | 4.1 | 93 | |
| 62 | 0.122 | 94 | |
| 63 | 1.704 | 95 | 75 |
| 64 | 0.025 | 96 | 1.27 |
| 65 | 0.053 | 97 | 2.7 |
| 66 | 5.7 | 98 | 1.5 |
| 67 | 0.049 | 99 | 0.138 |
| 68 | 11.6 | 100 | 0.192 |
| 69 | 0.41 | 101 | 75 |
| 70 | 55.1 | 102 | 51.2 |
| 71 | 48.5 | 103 | 75 |
| 72 | 0.019 | 104 | 0.056 |
| 105 | 0.276 | 128 | 0.368 |
| 106 | 5.89 | 129 | 3.6 |
| 107 | 0.144 | 130 | 0.004 |
| 108 | 0.905 | 131 | 0.014 |
| 109 | 2.15 | 132 | 0.002 |
| 110 | 0.077 | 133 | 0.021 |
| 111 | 1.9 | 134 | 0.706 |
| 112 | 1.4 | 135 | 0.261 |
| 113 | 0.197 | 136 | 10.3 |
| 114 | 0.118 | 137 | 0.058 |
| 115 | 0.033 | 138 | 0.027 |
| 116 | 0.005 | 139 | 0.295 |
| 117 | 0.089 | 140 | 0.004 |
| 118 | 0.037 | 141 | 0.004 |
| 119 | 3.4 | 142 | 75 |
| 120 | 1.3 | 143 | |
| 121 | 0.001 | 144 | 0.032 |
| 122 | | 145 | 7.9 |
| 123 | 0.002 | 146 | 0.048 |
| 124 | 0.002 | 147 | 0.066 |
| 125 | 0.005 | 148 | 0.648 |
| 126 | 0.048 | | |
| 127 | 0.045 | | |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

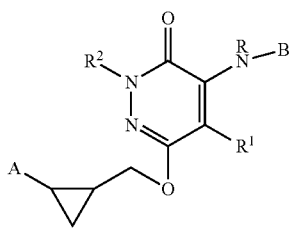

wherein:
R is hydrogen, $C_{1-6}$alkyl, $C_{2-4}$alkenyl, $C_{2-4}$alkynyl, or $(CH_2)_nC_{5-10}$ heteroaryl said heteroaryl optionally substituted with 1 to 3 groups of $R^a$;
$R^1$ is hydrogen, $C_{1-6}$alkyl or halogen, said alkyl optionally substituted with 1 to 3 groups of $R^a$;
$R^2$ is $C_{1-6}$alkyl, or $(CH_2)_nC_{6-10}$aryl, said aryl optionally substituted with 1 to 3 groups of $R^a$;
A is $C_{5-10}$heteroaryl optionally substituted with 1 to 3 groups of $R^a$;
B is $(CH_2)_nC_{6-10}$aryl, $(CH_2)_nC_{5-10}$heteroaryl, —C(O)(CH_2)_nC_{6-10}$aryl, or —C(O)(CH_2)_nC_{5-10}$heteroaryl, said aryl and heteroaryl optionally substituted with 1 to 3 groups of $R^a$;
$R^a$ selected from the group consisting of:
(1) $(CH_2)_nO_{0-1}C_{1-4}$ haloalkyl,
(2) halogen,
(3) $(CH_2)_nOR$,
(4) $C_{1-6}$alkyl,
(5) $(CH_2)_nC_{3-6}$cycloalkyl,
(6) $(CH_2)_nC_{6-10}$aryl, said aryl optionally substituted with one or more of OR, or $C_{1-6}$alkyl;
(7) —$(CH_2)_nCO_2R$,
(8) —$(CH_2)_nCN$,
(9) $S(O)_pR$,
(10) $C_{2-6}$ alkenyl,
(11) —$N(R)_2$,
n is 0, 1, 2, 3, or 4,
p is 0, 1, or 2,
or a pharmaceutically acceptable salt thereof.

2. The compound according to claim 1 wherein A is selected from the group consisting of pyridyl, quinolinyl, pyrazolyl, indazolyl, and cyclopentapyridinyl said of pyridyl, quinolinyl, pyrazolyl, indazolyl, and cyclopentapyridinyl optionally substituted with 1 to 3 groups of $R^a$.

3. The compound according to claim 2 wherein A is optionally substituted pyridyl or pyrazolyl.

4. The compound according to claim 1 wherein B is selected from the group consisting of $(CH_2)_nC_{6-10}$aryl and $(CH_2)_nC_{5-10}$ heteroaryl and the aryl or heteroaryl is isoxazolyl, pyrimidinyl, pyradizinyl, pyrazolopyridinyl, triazolyl thiazolyl, thiadiazolyl, phenyl, pyridyl, or pyrazolyl, said isoxazolyl, pyrimidinyl, pyradizinyl, pyrazolopyridinyl, triazolyl thiazolyl, thiadiazolyl, phenyl, pyridyl, and pyrazolyl are optionally substituted with 1 to 3 groups of $R^a$.

5. The compound according to claim 1 wherein B is selected from the group consisting of —C(O)C_{6-10}$aryl and —(CO)C_{5-10}$ heteroaryl and the aryl or heteroaryl is isoxazolyl, pyrimidinyl, pyradizinyl, pyrazolopyridinyl, triazolyl thiazolyl, thiadiazolyl, phenyl, pyridyl, or pyrazolyl, said isoxazolyl, pyrimidinyl, pyradizinyl, pyrazolopyridinyl, triazolyl thiazolyl, thiadiazolyl, phenyl, pyridyl, and pyrazolyl are optionally substituted with 1 to 3 groups of $R^a$.

6. The compound according to claim 3 wherein B is optionally substituted $CH_2$thiazolyl, $CH_2$pyridyl, or $CH_2$pyrazolyl.

7. The compound according to claim 4 wherein B is optionally substituted $CH_2$thiazolyl, $CH_2$pyridyl, or $CH_2$pyrazolyl.

8. The compound according to claim 1 wherein A is optionally substituted pyridyl and B is optionally substituted $CH_2$thiazoly, $CH_2$pyridyl, or $CH_2$pyrazolyl.

9. The compound according to claim 1 wherein A is optionally substituted pyrazolyl and B is optionally substituted $CH_2$thiazoly, $CH_2$pyridyl, or $CH_2$pyrazolyl.

10. The compound according to claim 1 wherein A is optionally substituted quinolinyl, pyridyl, pyrazolyl or indazolyl and B is selected from the group consisting of -optionally substituted $C(O)C_{6-10}$aryl and —$(CO)C_{5-10}$ heteroaryl and the aryl or heteroaryl is isoxazolyl, pyrimidinyl, pyradizinyl, pyrazolopyridinyl, triazolyl thiazolyl, thiadiazolyl, phenyl, pyridyl, or pyrazolyl.

11. The compound according to claim 1 which is represented by formula Ia, Iaa or Ib:

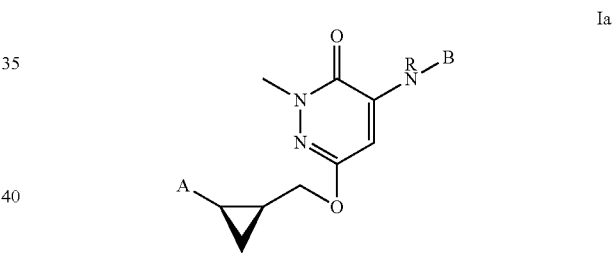

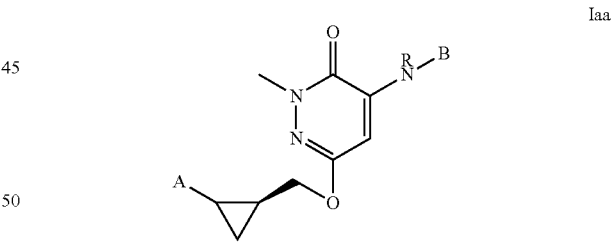

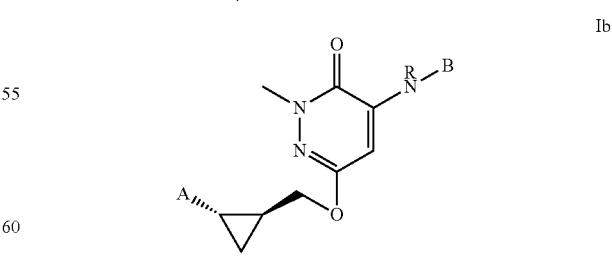

wherein R, A, and B are as defined herein; or a pharmaceutically acceptable salt thereof.

12. The compound according to claim 1 represented by structural formula Ic:

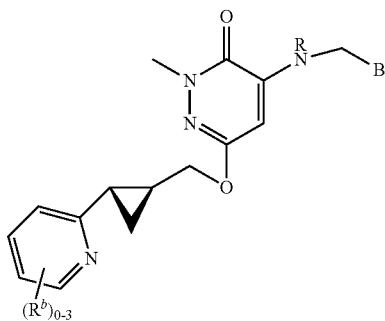

wherein R, and B are as defined herein and $R^b$ is $R^a$; or a pharmaceutically acceptable salt thereof.

13. The compound according to claim 1 represented by structural formula Id:

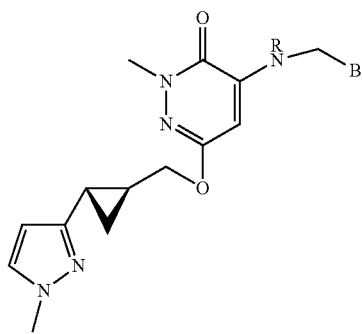

wherein R, and B are as defined herein, or a pharmaceutically acceptable salt thereof.

14. A compound which is:
2-methyl-4-((5-methyl-1,3,4-thiadiazol-2-yl)methylamino)-6-(((1S,2S)-2-(5-methyl pyridin-2-yl)cyclopropyl)methoxy)pyridazin-3(2H)-one,
2-methyl-6-(((1S,2S)-2-(1-methyl-1H-pyrazol-3-yl)cyclopropyl)methoxy)-4-(2-methylthiazol-5-yl)methylamino)pyridazin-3(2H)-one,
2-methyl-4-(5-methyl-1,3,4-thiadiazol-2-yl)methylamino)-6-(((1S,2S)-2-(quinolin-2-yl)cyclopropyl)methoxy)pyridazin-3(2H)-one,
6-(((1S,2S)-2-(5-methoxypyridin-2-yl)cyclopropyl)methoxy)-2-methyl-4-((5-methyl-1,3,4-thiadiazol-2-yl)methylamino)pyridazin-3(2H)-one,
6-(((1S,2S)-2-(5-(difluoromethoxy)pyridin-2-yl)cyclopropyl)methoxy)-2-methyl-4-((5-methyl-1,3,4-thiadiazol-2-yl)methylamino)pyridazin-3(2H)-one,
2-methyl-4-((5-methyl-1,3,4-thiadiazol-2-yl)-methylamino)-6-(((1S,2S)-2-(1-methyl-1H-pyrazol-3-yl)cyclopropyl)methoxy)pyridazin-3(2H)-one,
6-(((1S,2S)-2-(5-fluoropyridin-2-yl)cyclo-propyl)methoxy)-2-methyl-4-((5-methyl-1,3,4-thiadiazol-2-yl)methyl-amino)pyridazin-3(2H)one,
4-(4-methoxybenzylamino)-2-methyl-6-(((1S,2S)-2-(5-methylpyridin-2-yl)cyclopropyl)methoxy)pyridazin-3(2H)-one,
2-methyl-6-(((1S,2S)-2-(5-methylpyridin-2-yl)cyclopropyl)methoxy)-4-((5-methylpyridin-2-yl)methylamino)pyridazin-3(2H)-one,
2-methyl-4-((1-methyl-1H-pyrazol-4-yl)methylamino)-6-(((1S,2S)-2-(5-methylpyridin-2-yl)cyclopropyl)methoxy)pyridazin-3(2H)-one,
2-methyl-6-(((1S,2S)-2-(5-methylpyridin-2-yl)cyclopropyl)methoxy)-4-((6-methylpyridin-3-yl)methylamino)pyridazin-3(2H)-one,
2-methyl-6-(((1S,2S)-2-(5-methylpyridin-2-yl)cyclo-propyl)methoxy)-4-((4-methylthiazol-2-yl)methyl-amino)pyridazin-3(2H)one,
2-methyl-6-(((1S,2S)-2-(5-methylpyridin-2-yl)cyclopropyl)methoxy)-4-((2-methylthiazol-5-yl)methylamino)pyridazin-3(2H)-one,
4-((1,3-dimethyl-1H-pyrazol-5-yl)methylamino-)-2-methyl-6-(((1S,2S)-2-(5-methylpyridin-2-yl)cyclopropyl)methoxy)pyridazin-3(2H)-one,
6-(((1S,2S)-2-(5-fluoro-pyridin-2-yl)-cyclopropyl-)methoxy)-4-(4-methoxybenzylamino)-2-methyl-pyridazin-3(2H)-one,
6-(((1S,2S)-2-(5-fluoropyridin-2-yl)cyclopropyl)methoxy)-2-methyl-4-((5-methylpyridin-2-yl)methylamino)pyridazin-3(2H)-one,
4-(4-methoxybenzylamino)-2-methyl-6-(((1S,2S)-2-(1-methyl-1H-pyrazol-3-yl)cyclopropyl)methoxy)pyridazin-3(2H)-one,
4-(4-(((1S,2S)-2-(5-(difluoromethoxy)pyridin-2-yl)cyclopropyl)-methoxy)-2-methyl-pyrimidin-5-yl)-1-methylpyridin-2(1H)-one,
6-(((1S,2S)-2-(5-fluoropyridin-2-yl)cyclo-propyl)methoxy)-2-methyl-4-((1-methyl-1H-pyrazol-4-yl)methylamino-)pyridazin-3(2H)-one,
2-methyl-6-(((1S,2S)-2-(1-methyl-1H-pyrazol-3-yl)cyclopropyl)methoxy)-4-((6-methylpyridin-3-yl)methylamino)pyridazin-3(2H)-one,
4-((1,3-dimethyl-1H-pyrazol-5-yl)methylamino)-2-methyl-6-(((1S,2S)-2-(1-methyl-1H-pyrazol-3-yl)cyclopropyl)methoxy)pyridazin-3(2H)-one,
6-(((1S,2S)-2-(5-fluoropyridin-2-yl)cyclopropyl)methoxy)-2-methyl-4-((2-methylthiazol-5-yl)methylamino)pyridazin-3(2H)-one,
2-methyl-6-(((1S,2S)-2-(1-methyl-1H-pyrazol-3-yl)cyclopropyl)methoxy)-4-((1-methyl-1H-pyrazol-4-yl)methylamino)-pyridazin-3(2H)-one,
2-methyl-6-(((1S,2S)-2-(1-methyl-1H-pyrazol-3-yl)-cyclopropyl)methoxy)-4-((5-methylpyridin-2-yl)-methylamino)pyridazin-3(2H)-one,
6-(((1S,2S)-2-(5-chloropyridin-2-yl)cyclopropyl)methoxy)-2-methyl-4-((5-methyl-1,3,4-thiadiazol-2-yl)methylamino)pyridazin-3(2H)-one,
2-methyl-6-(((1S,2S)-2-(1-methyl-1H-pyrazol-3-yl)cyclopropyl)methoxy)-4-((5-methylthiazol-2-yl)methylamino)pyridazin-3(2H)-one,
6-(((1S,2S)-2-(5-chloro-pyridin-2-yl)cyclopropyl)-methoxy)-2-methyl-4-((1-methyl-1H-pyrazol-4-yl)methylamino)pyridazin-3(2H)-one,
6-(((1S,2S)-2-(5-(difluoro-methoxy)pyridin-2-yl)-cyclopropyl)-methoxy)-4-((1,3-dimethyl-1H-pyrazol-5-yl)methyl-amino)-2-methylpyridazin-3(2H)one,
6-(((1S,2S)-2-(5-(difluoromethoxy)pyridin-2-yl)cyclopropyl)-methoxy)-2-methyl-4-((2-methylthiazol-5-yl)methyl-amino)pyridazin-3(2H)one,
6-(((1S,2S)-2-(5-(difluoromethoxy)pyridin-2-yl)cyclopropyl)methoxy)-2-methyl-4-((1-methyl-1H-pyrazol-4-yl)methylamino)pyridazin-3(2H)-one,
2-methyl-6-(((1S,2S)-2-(5-methylpyridin-2-yl)cyclopropyl)methoxy)-4-((5-methylthiazol-2-yl)methylamino)pyridazin-3(2H)-one, 6-(((1S,2S)-2-(5-fluoropyridin-2-yl)cyclopropyl)methoxy)-2-methyl-4-((5-methylthiazol-2-yl)methylamino)pyridazin-3(2H)-one, 6-(((1S,2S)-2-(5-chloropyridin-2-yl)cyclopropyl)methoxy)-4-((1,3-dimethyl-1H-pyrazol-5-yl)methylamino)-2-methylpyridazin-3(2H)-one, 6-(((1S,2S)-2-(5-chloropyridin-2-yl)cyclopropyl)methoxy)-2-methyl-4-((2-methylthiazol-5-yl)methylamino)pyridazin-3(2H)-one, 4-((4-chloro-1,3-dimethyl-1H-pyrazol-5-yl)methylamino)-2-methyl-6-(((1S,2S)-2-(5-methylpyridin-2-yl)cyclopropyl)methoxy)pyridazin-3(2H)-one, 2-methyl-4-(methyl((5-methyl-1,3,4-thiadiazol-2-yl)methyl)amino)-6-(((1S,2S)-2-(quinolin-2-yl)cyclopropyl)methoxy)pyridazin-3(2H)-one, 4-((1,3-dimethyl-1H-pyrazol-4-yl)methylamino)-6-(((1S,2S)-2-(5-methoxypyridin-2-yl)cyclopropyl)methoxy)-2-methylpyridazin-3(2H)-one, 4-((5-chloro-1,3-dimethyl-1H-pyrazol-4-yl)methylamino)-2-methyl-6-(((1S,2S)-2-(5-methylpyridin-2-yl)cyclopropyl)methoxy)pyridazin-3(2H)-one, 4-((5-chloro-1,3-dimethyl-1H-pyrazol-4-yl)methylamino)-6-(((1S,2S)-2-(5-methoxypyridin-2-yl)cyclopropyl)methoxy)-2-methylpyridazin-3(2H)-one, 4-(((5-chloro-1,3-dimethyl-1H-pyrazol-4-yl)methyl)amino)-2-methyl-6-(((1S,2S)-2-(1-methyl-1H-pyrazol-3-yl)cyclopropyl)methoxy)pyridazin-3(2H)-one, 6-(((1S,2S)-2-(5-methoxypyridin-2-yl)cyclopropyl)methoxy)-2-methyl-4-(((1,3,5-trimethyl-1H-pyrazol-4-yl)methyl)amino)pyridazin-3(2H)-one, 2-methyl-6-(((1S,2S)-2-(1-methyl-1H-pyrazol-3-yl)cyclopropyl)methoxy)-4-(((1,3,5-trimethyl-1H-pyrazol-4-yl)methyl)amino)pyridazin-3(2H)-one, 2-methyl-6-(((1S,2S)-2-(5-methylpyridin-2-yl)-cyclopropyl)methoxy)-4-(((1,3,5-trimethyl-1H-pyrazol-4-yl)methyl)-amino)pyridazin-3(2H)one, 2-methyl-6-(((1S,2S)-2-(1-methyl-1H-pyrazol-3-yl)cyclopropyl)methoxy)-4-((thiazol-5-ylmethyl)-amino)pyridazin-3(2H)one, 2-methyl-6-(((1S,2S)-2-(5-methylpyridin-2-yl)cyclopropyl)methoxy)-4-((thiazol-5-ylmethyl)amino)pyridazin-3(2H)-one, 6-(((1S,2S)-2-(5-methoxypyridin-2-yl)cyclopropyl)methoxy)-2-methyl-4-((thiazol-5-ylmethyl)amino)pyridazin-3(2H)-one, 2-methyl-6-(((1S,2S)-2-(1-methyl-1H-pyrazol-3-yl)cyclopropyl)methoxy)-4-((thiazol-2-ylmethyl)amino)pyridazin-3(2H)-one, 2-methyl-6-(((1S,2S)-2-(1-methyl-1H-pyrazol-3-yl)cyclopropyl)methoxy)-4-(((2-methylthiazol-4-yl)methyl)amino)pyridazin-3(2H)-one, 6-(((1S,2S)-2-(5-methoxypyridin-2-yl)cyclopropyl)methoxy)-2-methyl-4-(((2-methylthiazol-4-yl)methyl)amino-)pyridazin-3(2H)-one, 4-(((2,6-dimethylpyridin-3-yl)methyl)amino)-6-(((1S,2S)-2-(5-methoxypyridin-2-yl)cyclopropyl)methoxy)-2-methylpyridazin-3(2H)-one, 4-(((2,6-dimethylpyridin-3-yl)methyl)amino)-2-methyl-6-(((1S,2S)-2-(1-methyl-1H-pyrazol-3-yl)cyclopropyl)methoxy)pyridazin-3(2H)-one, 4-(((2,6-dimethylpyridin-3-yl)methyl)amino)-2-methyl-6-(((1S,2S)-2-(5-methylpyridin-2-yl)cyclopropyl)methoxy)pyridazin-3(2H)-one, 4-(((2,6-dimethylpyridin-3-yl)methyl)amino)-6-(((1S,2S)-2-(5-fluoro-pyridin-2-yl)cyclopropyl-)methoxy)-2-methyl-pyridazin-3(2H)-one, 6-(((1S,2S)-2-(5-chloro-pyridin-2-yl)cyclopropyl-)methoxy)-4-(((2,6-dimethylpyridin-3-yl)methyl)amino)-2-methylpyridazin-3(2H)one, 4-(((2,6-dimethylpyridin-3-yl)methyl)amino)-2-methyl-6-(((1S,2S)-2-(pyridin-2-yl)cyclopropyl)methoxy)pyridazin-3(2H)-one, 6-(((1S,2S)-2-(6,7-dihydro-5H-cyclopenta[b]pyridin-2-yl)cyclopropyl)methoxy)-4-(((2,6-dimethylpyridin-3-yl)methyl)amino)-2-methylpyridazin-3(2H)-one, 4-(((2,6-dimethylpyridin-3-yl)methyl)amino)-2-methyl-6-(((1S,2S)-2-(quinolin-2-yl)cyclopropyl)methoxy)pyridazin-3(2H)-one, 6-(((1S,2S)-2-(5-(difluoromethoxy)pyridin-2-yl)cyclopropyl)methoxy)-4-(((2,6-dimethylpyridin-3-yl)methyl)amino)-2-methylpyridazin-3(2H)-one, 4-(((3,5-dimethylisoxazol-4-yl)methyl)amino)-6-(((1S,2S)-2-(5-methoxy-pyridin-2-yl)cyclopropyl-)methoxy)-2-methyl-pyridazin-3(2H)-one, 4-(((3,5-dimethylisoxazol-4-yl)methyl)amino)-2-methyl-6-(((1S,2S)-2-(5-methylpyridin-2-yl)cyclo-propyl)methoxy)pyridazin-3(2H)-one, 4-(((3,5-dimethylisoxazol-4-yl)methyl)amino)-2-methyl-6-(((1S,2S)-2-(1-methyl-1H-pyrazol-3-yl)cyclopropyl)methoxy)pyridazin-3(2H)-one, 6-(((1S,2S)-2-(5-methoxy-pyridin-2-yl)cyclopropyl-)methoxy)-2-methyl-4-(((2-methylpyridin-4-yl)methyl)amino)pyridazin-3(2H)-one, 6-(((1S,2S)-2-(5-methoxypyridin-2-yl)cyclopropyl)methoxy)-2-methyl-4-((pyrimidin-5-ylmethyl)amino)pyridazin-3(2H)-one, 6-(((1S,2S)-2-(5-methoxypyridin-2-yl)cyclopropyl)methoxy)-2-methyl-4-(((6-methylpyridin-3-yl)methyl)amino)pyridazin-3(2H)-one, 6-(((1S,2S)-2-(5-methoxypyridin-2-yl)cyclopropyl)methoxy)-2-methyl-4-(((2-methylpyridin-3-yl)methyl)amino)pyridazin-3(2H)-one, 6-(((1S,2S)-2-(5-methoxypyridin-2-yl)cyclopropyl)methoxy)-2-methyl-4-((pyrazin-2-ylmethyl)amino)pyridazin-3(2H)-one, 6-(((1S,2S)-2-(5-methoxypyridin-2-yl)cyclopropyl)methoxy)-2-methyl-4-(((5-methylpyridin-3-yl)methyl)amino)pyridazin-3(2H)-one, 6-(((1S,2S)-2-(5-methoxypyridin-2-yl)cyclopropyl)methoxy)-2-methyl-4-((pyridin-3-ylmethyl)amino)pyridazin-3(2H)-one, 4-(((5,6-dimethylpyridin-2-yl)methyl)amino)-6-(((1S,2S)-2-(5-methoxy-pyridin-2-yl)cyclopropyl-)methoxy)-2-methyl-pyridazin-3(2H)-one, 4-(((3-fluoro-6-methyl-pyridin-2-yl)methyl)-amino)-6-(((1S,2S)-2-(5-methoxy-pyridin-2-yl)-cyclopropyl)methoxy)-2-methylpyridazin-3(2H)one, 4-(((3,6-dimethylpyridin-2-yl)methyl)amino)-6-(((1S,2S)-2-(5-methoxy-pyridin-2-yl)cyclopropyl-)methoxy)-2-methylpyridazin-3(2H)one, 6-(((1S,2S)-2-(5-methoxy-pyridin-2-yl)cyclopropyl-)methoxy)-2-methyl-4-(((5-methylpyridin-2-yl)-methyl)amino)pyridazin-3(2H)-one, 6-(((1S,2S)-2-(5-methoxypyridin-2-yl)cyclopropyl)methoxy)-2-methyl-4-(((3-methyl-pyridin-2-yl)methyl)-amino)pyridazin-3(2H)one, 4-(((5-fluoro-6-methyl-pyridin2yl)methyl)amino)-6-(((1S,2S)-2-(5-methoxy-pyridin-2-yl)cyclopropyl-)methoxy)-2-methyl-pyridazin-3(2H)-one, 4-(((5-chloro-6-methyl-pyridin-2-yl)methyl)-amino)-6-(((1S,2S)-2-(5-methoxypyridin-2-yl)cyclopropyl)methoxy)2-methylpyridazin-3(2H)one, 6-(((1S,2S)-2-(5-methoxy-pyridin-2-yl)cyclopropyl-)methoxy)-2-methyl-4-(((6-methylpyridazin-3-yl)methyl)amino)pyridazin-3(2H)-one,
4-((1-(4-methoxybenzyl)-3-methyl-1H-pyrazol-4-yl)methylamino)-6-(((1S,2S)-2-(5-methoxy-pyridin-2-yl)cyclopropyl)-methoxy)-2-methyl-pyridazin-3(2H)-one,
6-(((1S,2S)-2-(5-methoxy-pyridin-2-yl)cyclopropyl-)methoxy)-2-methyl-4-((pyrazolo[1,5-a]pyridin-3-ylmethyl)amino)pyridazin-3(2H)-one,
2-methyl-6-(((1S,2S)-2-(5-methylpyridin-2-yl)cyclopropyl)methoxy)-4-((pyrazolo[1,5-a]pyridin-3-ylmethyl)amino)-pyridazin-3(2H)-one,
2-methyl-6-(((1S,2S)-2-(1-methyl-1H-pyrazol-3-yl)cyclopropyl)methoxy)-4-((pyrazolo[1,5-a]pyridin-3-ylmethyl)amino)-pyridazin-3(2H)-one,
4-(((5-(dimethylamino)-1-methyl-1H-pyrazol-4-yl)methyl)amino)-2-methyl-6-(((1S,2S)-2-(5-methylpyridin-2-yl)cyclopropyl)methoxy)pyridazin-3(2H)-one,
4-(((5-(dimethylamino)-1-methyl-1H-pyrazol-4-yl)methyl)amino)-2-methyl-6-(((1S,2S)-2-(1-methyl-1H-pyrazol-3-yl)cyclopropyl)methoxy)pyridazin-3(2H)-one,
4-(((5-(dimethylamino)-1-methyl-1H-pyrazol-4-yl)methyl)amino)-6-(((1S,2S)-2-(5-methoxypyridin-2-yl)cyclopropyl)methoxy)-2-methylpyridazin-3(2H)-one,
4-(((1,4-dimethyl-1H-pyrazol-5-yl)methyl)amino)-6-(((1S,2S)-2-(5-methoxypyridin-2-yl)cyclopropyl)methoxy)-2-methylpyridazin-3(2H)-one,
4-(((1,4-dimethyl-1H-pyrazol-5-yl)methyl)amino)-2-methyl-6-(((1S,2S)-2-(5-methylpyridin-2-yl)cyclopropyl)methoxy)pyridazin-3(2H)-one,
4-(((1,4-dimethyl-1H-pyrazol-5-yl)methyl)amino)-2-methyl-6-(((1S,2S)-2-(1-methyl-1H-pyrazol-3-yl)cyclopropyl)methoxy)pyridazin-3(2H)-one,
6-(((1S,2S)-2-(5-methoxypyridin-2-yl)cyclopropyl)methoxy)-2-methyl-4-(((5-methylisoxazol-3-yl)methyl)amino)pyridazin-3(2H)-one,
4-(((1,3-dimethyl-1H-1,2,4-triazol-5-yl)methyl)amino)-6-(((1S,2S)-2-(5-methoxypyridin-2-yl)cyclopropyl)methoxy)-2-methylpyridazin-3(2H)-one,
6-(((1S,2S)-2-(5-methoxypyridin-2-yl)cyclopropyl)methoxy)-2-methyl-4-(((3-methylisoxazol-5-yl)methyl)amino)pyridazin-3(2H)-one,
4-(((1,4-dimethyl-1H-pyrazol-3-yl)methyl)amino)-6-(((1S,2S)-2-(5-methoxypyridin-2-yl)cyclopropyl)methoxy)-2-methylpyridazin-3(2H)-one,
4-(bis((2,6-dimethylpyridin-3-yl)methyl)amino)-6-(((1S,2S)-2-(5-methoxypyridin-2-yl)cyclopropyl)methoxy)-2-methylpyridazin-3(2H)-one,
6-(((1S,2S)-2-(5-methoxypyridin-2-yl)cyclopropyl)methoxy)-2-methyl-4-(((1-methyl-1H-pyrazol-3-yl)methyl)-amino)pyridazin-3(2H)one,
2-methyl-4-(((1-methyl-1H-pyrazol-3-yl)methyl)-amino)-6-(((1S,2S)-2-(5-methylpyridin-2-yl)cyclopropyl)methoxy)pyridazin-3(2H)-one,
2-methyl-6-(((1S,2S)-2-(1-methyl-1H-pyrazol-3-yl)cyclopropyl)methoxy)-4-(((1-methyl-1H-pyrazol-3-yl)methyl)amino)-pyridazin-3(2H)-one,
5-chloro-N-(6-(((1S,2S)-2-(5-methoxypyridin-2-yl)-cyclopropyl)methoxy)-2-methyl-3-oxo-2,3-dihydro-pyridazin-4-yl)-1-methyl-1Hpyrazole-4carboxamide,
4-(((5-chloro-1-methyl-1H-pyrazol-4-yl)methyl)-amino)-6-(((1S,2S)-2-(5-methoxypyridin-2-yl)-cyclopropyl)methoxy)-2-methylpyridazin-3(2H)one,
6-(((1S,2S)-2-(5-methoxypyridin-2-yl)-cyclopropyl)methoxy)-2-methyl-4-(((6-methyl-pyridin-2-yl)methyl)-amino)pyridazin-3(2H)one,
2-methyl-6-(((1S,2S)-2-(1-methyl-1H-pyrazol-3-yl)cyclopropyl)methoxy)-4-(((1-methyl-1H-pyrazol-5-yl)methyl)amino)-pyridazin-3(2H)-one,
2-methyl-4-(((1-methyl-1H-pyrazol-5-yl)methyl-)amino)-6-(((1S,2S)-2-(5-methylpyridin-2-yl)cyclopropyl)methoxy)pyridazin-3(2H)-one,
6-(((1S,2S)-2-(5-methoxypyridin-2-yl)-cyclopropyl)methoxy)-2-methyl-4-(((1-methyl-1H-pyrazol-5-yl)methyl)-amino)pyridazin-3(2H)one,
N-(6-(((1S,2S)-2-(5-methoxypyridin-2-yl)-cyclopropyl)methoxy)-2-methyl-3-oxo-2,3-dihydropyridazin-4-yl)-1,3-dimethyl-1H-pyrazole-5-carboxamide,
1,3-dimethyl-N-(2-methyl-6-(((1S,2S)-2-(5-methyl-pyridin-2-yl)cyclopropyl-)methoxy)-3-oxo-2,3-dihydropyridazin-4-yl)-1H-pyrazole-5-carboxamide,
1,3-dimethyl-N-(2-methyl-6-(((1S,2S)-2-(1-methyl-1H-pyrazol-3-yl)cyclopropyl)methoxy)-3-oxo-2,3-dihydropyridazin-4-yl)-1H-pyrazole-5-carboxamide,
2-methyl-4-(((1-methyl-3-(trifluoromethyl)-1H-pyrazol-4-yl)methyl)amino)-6-(((1S,2S)-2-(5-methylpyridin-2-yl)cyclopropyl)methoxy)pyridazin-3(2H)-one,
6-(((1S,2S)-2-(5-methoxypyridin-2-yl)cyclopropyl)methoxy)-2-methyl-4-(((4-methylpyridin-2-yl)methyl)amino)pyridazin-3(2H)-one,
4-(((1-ethyl-1H-pyrazol-3-yl)methyl)amino)-6-(((1S,2S)-2-(5-methoxypyridin-2-yl)cyclopropyl)methoxy)-2-methylpyridazin-3(2H)-one,
4-((1-(difluoromethyl)-1H-pyrazol-4-yl)methylamino)-6-(((1S,2S)-2-(5-methoxypyridin-2-yl)cyclopropyl)methoxy)-2-methylpyridazin-3(2H)-one,
2-methyl-4-((5-methyl-1,3,4-thiadiazol-2-yl)-methylamino)-6-(((1S,2S)-2-(1-methyl-1H-indazol-3-yl)cyclopropyl)methoxy)pyridazin-3(2H)-one,
2-methyl-6-(((1S,2S)-2-(1-methyl-1H-indazol-3-yl)cyclopropyl)methoxy)-4-((2-methylthiazol-5-yl)methylamino)pyridazin-3(2H)-one,
2-methyl-6-(((1R,2R)-2-(1-methyl-1H-indazol-3-yl)cyclopropyl)methoxy)-4-((2-methylthiazol-5-yl)methylamino)pyridazin-3(2H)-one,
2-methyl-6-(((1S,2S)-2-(1-methyl-1H-indazol-3-yl)cyclopropyl)methoxy)-4-((1-methyl-1H-pyrazol-4-yl)methylamino)-pyridazin-3(2H)-one,
2-methyl-6-(((1S,2S)-2-(1-methyl-1H-indazol-3-yl)cyclopropyl)methoxy)-4-((5-methylthiazol-2-yl)methylamino)pyridazin-3(2H)-one,
2-methyl-6-(((1R,2R)-2-(1-methyl-1H-indazol-3-yl)cyclopropyl)methoxy)-4-((1-methyl-1H-pyrazol-4-yl)methylamino)pyridazin-3(2H)-one,
2-methyl-6-(((1R,2R)-2-(1-methyl-1H-indazol-3-yl)cyclopropyl)methoxy)-4-((5-methylthiazol-2-yl)methylamino)pyridazin-3(2H)-one,
2-methyl-4-((5-methyl-1,3,4-thiadiazol-2-yl)methylamino)-6-(((1S,2S)-2-(6-methylpyridin-2-yl)cyclopropyl)methoxy)pyridazin-3(2H)-one,
4-((1,3-dimethyl-1H-pyrazol-5-yl)methylamino)-2-methyl-6-(((1S,2S)-2-(6-methylpyridin-2-yl)cyclopropyl)methoxy)pyridazin-3(2H)-one,
2-methyl-4-((1-methyl-1H-pyrazol-4-yl)methyl-amino)-6-(((1S,2S)-2-(6-methylpyridin-2-yl)cyclopropyl)methoxy)pyridazin-3(2H)-one,
2-methyl-6-(((1S,2S)-2-(6-methylpyridin-2-yl)cyclo-propyl)methoxy)-4-((5-methylthiazol-2-yl)methyl-amino)pyridazin-3(2H)one,
2-methyl-6-(((1S,2S)-2-(6-methylpyridin-2-yl)cyclo-propyl)methoxy)-4-(pyridin-2-ylmethylamino-)pyridazin-3(2H)-one, 2-methyl-6-(((1S,2S)-2-(6-methylpyridin-2-yl)cyclo-propyl)methoxy)-4-(pyridin-3-ylmethylamino-)pyridazin-3(2H)-one,
6-(((1S,2S)-2-(6,7-dihydro-5H-cyclopenta-[b]pyridin-2-yl)cyclop-ropyl)methoxy)-4-((1,3-dimethyl-1H-pyrazol-5-yl)methylamino)-2-methylpyridazin-3(2H)one,
6-(((1S,2S)-2-(6,7-dihydro-5H-cyclopenta-[b]pyridin-2-yl)cyclo-propyl)-methoxy)-2-methyl-4-((2-methylthiazol-5-yl)methyl-amino)pyridazin-3(2H)one,
6-(((1S,2S)-2-(6,7-dihydro-5H-cyclopenta-[b]pyridin-2-yl)cyclo-propyl)methoxy)-2-methyl-4-((5-methyl-1,3,4-thia-diazol-2-yl)methylamino)-pyridazin-3(2H)-one,
6-(((1S,2S)-2-(6,7-dihydro-5H-cyclopenta[b]pyridin-2-yl)cyclopropyl)methoxy)-2-methyl-4-((5-methylthiazol-2-yl)methylamino)pyridazin-3(2H)-one,
6-(((1S,2S)-2-(6,7-dihydro-5H-cyclopenta[b]pyridin-2-yl)cyclopropyl)methoxy)-2-methyl-4-((1-methyl-1H-pyrazol-4-yl)methylamino)pyridazin-3(2H)-one,
4-((4,5-dimethylthiazol-2-yl)methylamino)-6-(((1S,2S)-2-(5-methoxy-pyridin-2-yl)cyclopropyl-)methoxy)-2-methyl-pyridazin-3(2H)-one,
4-((4,5-dimethylthiazol-2-yl)methylamino)-2-methyl-6-(((1S,2S)-2-(5-methyl-pyridin-2-yl)cyclopropyl-)methoxy)pyridazin-3(2H)-one,
4-((4,5-dimethylthiazol-2-yl)methylamino)-2-methyl-6-(((1S,2S)-2-(1-methyl-1H-pyrazol-3-yl)cyclop-ropyl)methoxy)pyridazin-3(2H)-one,
4-((1,5-dimethyl-1H-pyrazol-3-yl)methylamino)-2-methyl-6-(((1S,2S)-2-(1-methyl-1H-pyrazol-3-yl)cyclopropyl)methoxy)pyridazin-3(2H)-one,
6-(((1S,2S)-2-(5-methoxy-pyridin-2-yl)cyclopropyl-)methoxy)-2-methyl-4-((5-methylthiazol-2-yl)-methylamino-)pyridazin-3(2H)-one,
6-(((1S,2S)-2-(5-methoxy-pyridin-2-yl)cyclopropyl-)methoxy)-2-methyl-4-((1-methyl-1H-pyrazol-4-yl)methylamino)pyridazin-3(2H)-one,
4-((1,3-dimethyl-1H-pyrazol-5-yl)methyl-amino)-6-(((1S,2S)-2-(5-methoxypyridin-2-yl)-cyclopropyl)methoxy)-2-methylpyridazin-3(2H)one,
4-(4-methoxybenzyl-amino)-6-(((1S,2S)-2-(5-methoxy-pyridin-2-yl)-cyclopropyl)methoxy)-2-methylpyridazin-3(2H)one,
6-(((1S,2S)-2-(5-methoxy-pyridin-2-yl)-cyclopropyl-)methoxy)-2-methyl-4-(pyridin-2-yl-methyl-amino)pyridazin-3(2H)one,
6-(((1S,2S)-2-(5-methoxy-pyridin-2-yl)cyclopropyl-)methoxy)-2-methyl-4-(pyridin-3-ylmethylamino-)pyridazin-3(2H)-one,
6-(((1S,2S)-2-(5-methoxy-pyridin-2-yl)cyclopropyl-)methoxy)-2-methyl-4-(2-(thiazol-2-yl)ethylamino-)pyridazin-3(2H)-one,
4-((3-ethyl-1-methyl-1H-pyrazol-5-yl)methylamino)-6-(((1S,2S)-2-(5-methoxypyridin-2-yl)cyclopropyl)methoxy)-2-methylpyridazin-3(2H)-one,
4-((3-ethyl-1-methyl-1H-pyrazol-5-yl)methylamino)-2-methyl-6-(((1S,2S)-2-(5-methylpyridin-2-yl)cyclopropyl)methoxy)pyridazin-3(2H)-one,
4-((3-ethyl-1-methyl-1H-pyrazol-5-yl)methylamino)-2-methyl-6-(((1S,2S)-2-(1-methyl-1H-pyrazol-3-yl)cyclopropyl)methoxy)pyridazin-3(2H)-one,
5-bromo-6-(((1S,2S)-2-(5-methoxypyridin-2-yl)cyclopropyl)methoxy)-2-methyl-4-((5-methyl-1,3,4-thiadiazol-2-yl)methyl-amino)pyridazin-3(2H)-one,
5-chloro-6-(((1S,2S)-2-(5-methoxypyridin-2-yl)cyclopropyl)methoxy)-2-methyl-4-((5-methyl-1,3,4-thiadiazol-2-yl)methylamino)pyridazin-3(2H)-one,
2-(4-methoxybenzyl)-6-(((1S,2S)-2-(5-methoxy-pyridin-2-yl)cyclopropyl-)methoxy)-4-((5-methyl-1,3,4-thiadiazol-2-yl)methyl-amino)pyridazin-3(2H)-one,
6-(((1S,2S)-2-(5-methoxypyridin-2-yl)cyclopropyl)methoxy)-4-((5-methyl-1,3,4-thiadiazol-2-yl)methylamino)pyridazin-3(2H)-one,
2-ethyl-6-(((1S,2S)-2-(5-methoxypyridin-2-yl)cyclopropyl)methoxy)-4-((5-methyl-1,3,4-thiadiazol-2-yl)methylamino)pyridazin-3(2H)-one,
4-((4-methoxybenzyl)(prop-2-ynyl)amino)-6-(((1S,2S)-2-(5-methoxypyridin-2-yl)cyclopropyl)methoxy)-2-methylpyridazin-3(2H)-one,
4-((1H-1,2,3-triazol-4-yl)methylamino)-6-(((1S,2S)-2-(5-methoxypyridin-2-yl)cyclopropyl)methoxy)-2-methylpyridazin-3(2H)-one,
6-(((1S,2S)-2-(5-methoxy-pyridin-2-yl)-cyclopropyl-)methoxy)-2-methyl-4-((1-methyl-1H-1,2,3-triazol-4-yl)methylamino)pyridazin-3(2H)-one,
6-(((1S,2S)-2-(5-methoxypyridin-2-yl)cyclopropyl)methoxy)-2-methyl-4-((2-methyl-2H-1,2,3-triazol-4-yl)methylamino)pyridazin-3(2H)-one
or a pharmaceutically acceptable salt thereof.

15. A pharmaceutical composition which comprises a pharmaceutically acceptable carrier and a compound of claim 1 or a pharmaceutically acceptable salt thereof.

16. A method for treating schizophrenia in a human patient in need thereof which comprises administering to the patient a therapeutically effective amount of a compound of claim 1 or a pharmaceutically acceptable salt thereof.

\* \* \* \* \*